US012780936B2

(12) United States Patent
Lanfrancone et al.

(10) Patent No.: US 12,780,936 B2
(45) Date of Patent: Nov. 3, 2026

(54) ANTIBODIES AGAINST TUMOR-ASSOCIATED ANTIGENS AND METHOD FOR OBTAINING THEM

(71) Applicant: IEO—ISTITUTO EUROPEO DI ONCOLOGIA S.R.L., Milan (IT)

(72) Inventors: Luisa Lanfrancone, Milan (IT); Paul Edward Massa, Milan (IT); Massimiliano Mazza, Milan (IT); Pier Giuseppe Pelicci, Milan (IT)

(73) Assignee: IEO—ISTITUTO EUROPEO DI ONCOLOGIA S.R.L., Milan (IT)

( * ) Notice: Subject to any disclaimer, the term of this patent is extended or adjusted under 35 U.S.C. 154(b) by 881 days.

(21) Appl. No.: 17/252,864

(22) PCT Filed: Jun. 19, 2019

(86) PCT No.: PCT/EP2019/066217
§ 371 (c)(1),
(2) Date: Dec. 16, 2020

(87) PCT Pub. No.: WO2019/243428
PCT Pub. Date: Dec. 26, 2019

(65) Prior Publication Data

US 2021/0155709 A1 May 27, 2021

(30) Foreign Application Priority Data

Jun. 19, 2018 (EP) .................................... 18178526

(51) Int. Cl.

| | |
|---|---|
| ***C07K 16/30*** | (2006.01) |
| ***A61P 35/00*** | (2006.01) |
| ***A61P 35/02*** | (2006.01) |
| ***C07K 14/525*** | (2006.01) |
| ***C12N 15/10*** | (2006.01) |
| ***G01N 33/57505*** | (2026.01) |
| ***G01N 33/5751*** | (2026.01) |
| *A61K 39/00* | (2006.01) |

(52) U.S. Cl.
CPC .............. *C07K 16/30* (2013.01); *A61P 35/00* (2018.01); *A61P 35/02* (2018.01); *C07K 14/525* (2013.01); *C12N 15/1037* (2013.01); *G01N 33/57505* (2026.01); *G01N 33/5751* (2026.01); *A61K 2039/505* (2013.01); *C07K 2317/33* (2013.01); *C07K 2317/622* (2013.01); *C07K 2319/00* (2013.01)

(58) Field of Classification Search
None
See application file for complete search history.

(56) References Cited

U.S. PATENT DOCUMENTS 5,677,171 A * 10/1997 Hudziak ............ C07K 16/3015 530/387.7
2013/0216528 A1* 8/2013 Cheung .................. C07K 16/44 435/7.1
2017/0355750 A1 12/2017 Yang et al.
2018/0094054 A1* 4/2018 Gill .................. A61K 47/68031

FOREIGN PATENT DOCUMENTS

| | | | |
|---|---|---|---|
| WO | 2006017173 | A1 | 2/2006 |
| WO | 2007128563 | A1 | 11/2007 |
| WO | 2010028791 | A1 | 3/2010 |
| WO | 2016180715 | A1 | 11/2016 |
| WO | 2017175176 | A1 | 10/2017 |
| WO | 2018002952 | A2 | 1/2018 |
| WO | 2018087172 | A1 | 5/2018 |

OTHER PUBLICATIONS

Rudikoff et al. (Proceedings of the National Academy of Sciences USA, vol. 79, p. 1979-1983, 1982) (Year: 1982).*
Johnson and Wu (Methods in Molecular Biology, Antibody Engineering: Methods and Protocols, vol. 248, p. 11-25, 2004) (Year: 2004).*
Silacci (Proteomics, vol. 5, p. 2340-2350, 2005) (Year: 2005).*
Krag (Cancer Research, vol. 66, No. 15, p. 7724-7733, 2006) (Year: 2006).*
Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Fidler, Biological heterogeneity of cancer, 2012, Human Vaccines and Immunotherapeutics, 8(8): 1141-1142. (Year: 2012).*
Bauer, "Targeted bioactivity of membrane-anchored TNF by an antibody-derived TNF fusion protein", The Journal of Immunology, 2004, vol. 172, No. 6, pp. 3930-3939.
Spitaleri et al., "Phase I/II study of the tumour-targeting human monoclonal antibody-cytokine fusion protein L19-TNF in patients with advanced solid tumours", Journal of Cancer Research and Clinical Oncology, 2013, vol. 139, No. 3, pp. 447-455.

(Continued)

*Primary Examiner* — Nelson B Moseley, II
*Assistant Examiner* — James Ryland Melchior
(74) *Attorney, Agent, or Firm* — Lucas & Mercanti, LLP

(57) ABSTRACT

The present invention refers to a method for identifying an immunoglobulin, recombinant or synthetic antigen-binding fragments thereof that present in vivo tumor binding activity and do not significantly cross-react with normal cells and to antibodies thereby obtained and to medical uses thereof.

18 Claims, 13 Drawing Sheets

Figure 1:
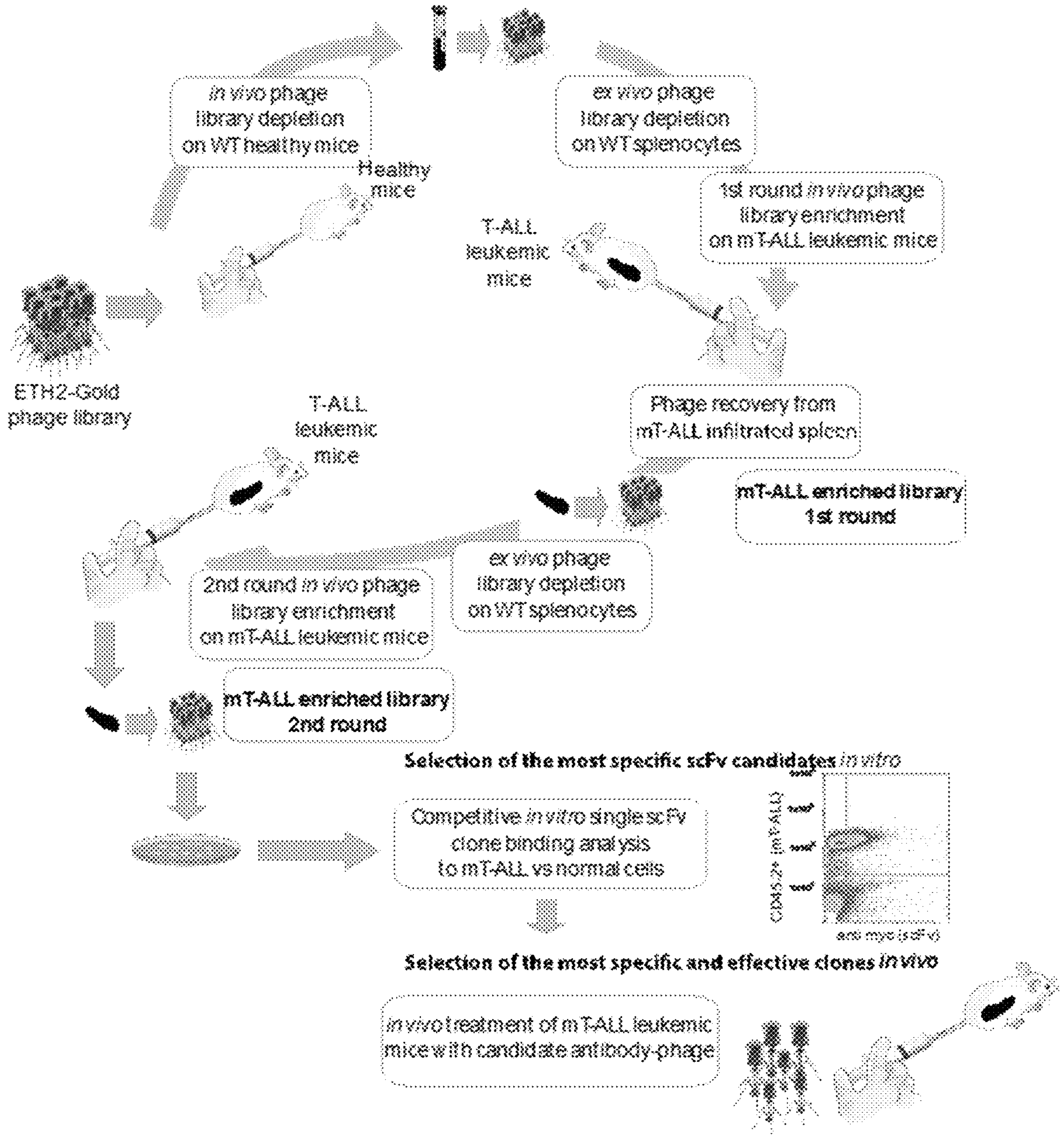

Specification includes a Sequence Listing.

(56) References Cited

OTHER PUBLICATIONS

Hoogenboom et al., "Construction and expression of antibody-tumor necrosis factor fusion proteins", Molecular Immunology, 1991, vol. 28, No. 9, pp. 1027-1037.
Fellermeier et al., " Advancing targeted co-stimulation with antibody-fusion proteins by introducing TNF superfamily members in a single-chain format", Oncoimmunology, 2016, vol. 5, No. 11, pp. e1238540-e1238540-11.
Sanchez-Martin et al., "Selection strategies for anticancer antibody discovery: searching off the beaten path", Trends in Biotechnology, 2015, vol. 33, No. 5, pp. 292-301.
Kurosawa et al., "Selection and analysis of anti-cancer antibodies for cancer therapy obtained from antibody phage library", Cancer Science, 2010, vol. 102, No. 1, pp. 175-181.
Alfaleh et al., "Strategies for Selecting Membrane Protein-Specific Antibodies using Phage Display with Cell-Based Panning", Antibodies, 2017, vol. 6, No. 10, pp. 1-19.
European Search Report for Corresponding European Application No. EP 18178526.2 (13 Pages) (Dec. 18, 2018).
International Search Report and Written Opinion for Corresponding International Application No. PCT/EP2019/066217 (14 Pages) ( Sep. 20, 2019).

* cited by examiner

SEQUENCE LISTING

```
<160> NUMBER OF SEQ ID NOS: 39

<210> SEQ ID NO 1
<211> LENGTH: 238
<212> TYPE: PRT
<213> ORGANISM: Artificial Sequence
<220> FEATURE:
<223> OTHER INFORMATION: scFv DP47-DPL16
<220> FEATURE:
<221> NAME/KEY: UNSURE
<222> LOCATION: (99)..(102)
<223> OTHER INFORMATION: Xaa can be any naturally occurring amino acid
<220> FEATURE:
<221> NAME/KEY: UNSURE
<222> LOCATION: (220)..(225)
<223> OTHER INFORMATION: Xaa can be any naturally occurring amino acid

<400> SEQUENCE: 1

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Xaa Xaa Xaa Xaa Asp Tyr Trp Gly Gln Gly Thr Leu Val Thr
100 105 110

Val Ser Ser Gly Gly Gly Gly Ser Gly Gly Gly Gly Ser Gly Gly Gly
115 120 125

Gly Ser Ser Glu Leu Thr Gln Asp Pro Ala Val Ser Val Ala Leu Gly
130 135 140

Gln Thr Val Arg Ile Thr Cys Gln Gly Asp Ser Leu Arg Ser Tyr Tyr
145 150 155 160

Ala Ser Trp Tyr Gln Gln Lys Pro Gly Gln Ala Pro Val Leu Val Ile
165 170 175

Tyr Gly Lys Asn Asn Arg Pro Ser Gly Ile Pro Tyr Arg Phe Ser Gly
180 185 190

Ser Ser Ser Gly Asn Thr Ala Ser Leu Thr Ile Thr Gly Ala Gln Ala
195 200 205

Glu Asp Glu Ala Asp Tyr Tyr Cys Asn Ser Ser Xaa Xaa Xaa Xaa Xaa
210 215 220

Xaa Val Val Phe Gly Gly Gly Thr Lys Leu Thr Val Leu Gly
225 230 235

<210> SEQ ID NO 2
<211> LENGTH: 239
<212> TYPE: PRT
<213> ORGANISM: Artificial Sequence
<220> FEATURE:
<223> OTHER INFORMATION: IEOmAB1 amino acid sequence

<400> SEQUENCE: 2

Glu Val Gln Leu Leu Glu Ser Gly Gly Gly Leu Ala Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Val Thr Arg Phe Asp Tyr Trp Gly Gln Gly Thr Leu Val
100 105 110

Thr Val Ser Ser Gly Gly Gly Gly Ser Gly Gly Gly Gly Ser Gly Gly
115 120 125

Gly Gly Ser Ser Glu Leu Thr Gln Asp Pro Ala Val Ser Val Ala Leu
130 135 140

```
Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Tyr Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Ser Arg Gly Leu Ala
    210                 215                 220

Arg Pro Val Val Val Gly Gly Gly Thr Lys Leu Thr Val Leu Gly
225                 230                 235


<210> SEQ ID NO 3
<211> LENGTH: 717
<212> TYPE: DNA
<213> ORGANISM: Artificial Sequence
<220> FEATURE:
<223> OTHER INFORMATION: IEOmAB1 DNA sequence

<400> SEQUENCE: 3

gaggtgcagc tgttggagtc tgggggaggc ttggcacagc ctggggggtc cctgagactc      60

tcctgtgcag cctctggatt cacctttagc agctatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcaaatga acagcctgag agccgaagac acggccgtat attactgtgc gaaatctgtt     300

actcgttttg actactgggg ccagggaacc ctggtcaccg tctcgagtgg tggaggcggt     360

tcaggcggag gtggctctgg cggtggcgga tcgtctgagc tgactcagga ccctgctgtg     420

tctgtggcct tgggacagac agtcaggatc acatgccaag gagacagtct cagaagctat     480

tatgcaagct ggtaccagca gaagccagga caggcccctg tacttgtcat ctatggtaaa     540

aacaaccggc cctcagggat cccataccga ttctctggct ccagctcagg aaacacagct     600

tccttgacca tcactggggc tcaggcggaa gatgaggctg actattactg taactcctct     660

agggggctgg cgcggcccgt ggtagtcggc ggagggacca agctgaccgt cctaggc        717


<210> SEQ ID NO 4
<211> LENGTH: 239
<212> TYPE: PRT
<213> ORGANISM: Artificial Sequence
<220> FEATURE:
<223> OTHER INFORMATION: IEOmAB2 amino acid sequence

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95

Ala Lys Thr Ala Ser Ile Leu Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Glu Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Tyr Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Ser Pro Trp His Arg
    210                 215                 220

Thr Ser Val Val Phe Gly Gly Gly Thr Lys Leu Thr Val Leu Gly
225                 230                 235


<210> SEQ ID NO 5
<211> LENGTH: 717
<212> TYPE: DNA
<213> ORGANISM: Artificial Sequence
<220> FEATURE:
<223> OTHER INFORMATION: IEOmAB2 DNA sequence

<400> SEQUENCE: 5

gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcaaatga acagcctgag agccgaagac acggccgtat attactgtgc gaaaacggct     300

tctattcttg actactgggg ccagggaacc ctggtcaccg tctcgagtgg tggaggcggt     360

tcaggcggag gtggctctgg cggtggcgga tcgtctgagc tgactcagga ccctgctgtg     420

tctgtggcct tgggacagac agtcaggatc acatgccaag gagacagtct cagaagctat     480

tatgcaagct ggtaccagca gaagccagga caggcccctg tacttgtcat ctatggtaaa     540

aacaaccggc cctcagggat cccataccga ttctctggct ccagctcagg aaacacagct     600

tccttgacca tcactggggc tcaggcggaa gatgaggctg actattactg taactcctct     660

ccctggcatc gtactagtgt ggtattcggc ggagggacca agctgaccgt cctaggc       717


<210> SEQ ID NO 6
<211> LENGTH: 241
<212> TYPE: PRT
<213> ORGANISM: Artificial Sequence
<220> FEATURE:
<223> OTHER INFORMATION: IEOmAB3 amino acid sequence

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Met Gly Arg Asn Ala Phe Asp Tyr Trp Gly Gln Gly Thr
            100                 105                 110

Leu Val Thr Ala Ser Ser Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Tyr Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Ser Pro Pro
    210                 215                 220

Thr Pro Asp Thr Val Val Phe Gly Gly Gly Thr Lys Leu Thr Val Leu
225                 230                 235                 240

Gly


<210> SEQ ID NO 7
<211> LENGTH: 723
<212> TYPE: DNA
<213> ORGANISM: Artificial Sequence
<220> FEATURE:
<223> OTHER INFORMATION: IEOmAB3 DNA sequence

<400> SEQUENCE: 7

gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcaaatga acagcctgag agccgaagac acggccgtat attactgtgc gaaagtgatg     300

ggtcggaatg cttttgacta ctggggccag ggaaccctgg tcaccgcctc gagtggtgga     360

ggcggttcag gcggaggtgg ctctggcggt ggcggatcgt ctgagctgac tcaggaccct     420

gctgtgtctg tggccttggg acagacagtc aggatcacat gccaaggaga cagtctcaga     480

agctattatg caagctggta ccagcagaag ccaggacagg cccctgtact tgtcatctat     540

ggtaaaaaca accggccctc agggatccca taccgattct ctggctccag ctcaggaaac     600

acagcttcct tgaccatcac tggggctcag gcggaagatg aggctgacta ttactgtaac     660

tcctctccgc ccactcctga tacggtggta ttcggcggag ggaccaagct gaccgtccta     720

ggc                                                                   723


<210> SEQ ID NO 8
```

<211> LENGTH: 477
<212> TYPE: DNA
<213> ORGANISM: Homo sapiens

<400> SEQUENCE: 8
atggtcagat catcttctcg aaccccgagt gacaagcctg tagcccatgt tgtagcaaac 60
cctcaagctg aggggcagct ccagtggctg aaccgccggg ccaatgccct cctggccaat 120
ggcgtggagc tgagagataa ccagctggtg gtgccatcag agggcctgta cctcatctac 180
tcccaggtcc tcttcaaggg ccaaggctgc ccctccaccc atgtgctcct cacccacacc 240
atcagccgca tcgccgtctc ctaccagacc aaggtcaacc tcctctctgc catcaagagc 300
ccctgccaga gggagacccc agagggggct gaggccaagc cctggtatga gcccatctat 360
ctgggagggg tcttccagct ggagaagggt gaccgactca gcgctgagat caatcggccc 420
gactatctcg actttgccga gtctgggcag gtctactttg ggatcattgc cctgtga 477

<210> SEQ ID NO 9
<211> LENGTH: 716
<212> TYPE: DNA
<213> ORGANISM: Artificial Sequence
<220> FEATURE:
<223> OTHER INFORMATION: hIgG1-Fc tag

<400> SEQUENCE: 9
atatcggcca tggttagatc tgacaaaact cacacatgcc caccgtgccc agcacctgaa 60
ctcctggggg gaccgtcagt cttcctcttc cccccaaaac ccaaggacac cctcatgatc 120
tcccggaccc ctgaggtcac atgcgtggtg gtggacgtga gccacgaaga ccctgaggtc 180
aagttcaact ggtacgtgga cggcgtggag gtgcataatg ccaagacaaa gccgcgggag 240
gagcagtaca acagcacgta ccgtgtggtc agcgtcctca ccgtcctgca ccaggactgg 300
ctgaatggca aggagtacaa gtgcaaggtc tccaacaaag ccctcccagc ccccatcgag 360
aaaaccatct ccaaagccaa agggcagccc cgagaaccac aggtgtacac cctgccccca 420
tcccgggatg agctgaccaa gaaccaggtc agcctgacct gcctggtcaa aggcttctat 480
cccagcgaca tcgccgtgga gtgggagagc aatgggcagc cggagaacaa ctacaagacc 540
acgcctcccg tgctggactc cgacggctcc ttcttcctct acagcaagct caccgtggac 600
aagagcaggt ggcagcaggg gaacgtcttc tcatgctccg tgatgcatga ggctctgcac 660
aaccactaca cgcagaagag cctctccctg tctccgggta aatgagtgct agctgg 716

<210> SEQ ID NO 10
<211> LENGTH: 475
<212> TYPE: PRT
<213> ORGANISM: Artificial Sequence
<220> FEATURE:
<223> OTHER INFORMATION: IEOmAB3-scFv-hIgG amino acid sequence

<400> SEQUENCE: 10

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr

-continued

```
65                  70                  75                  80

Leu Gln Met Asn Ser Leu Arg Ala Glu Asp Thr Ala Val Tyr Tyr Cys
                85                  90                  95

Ala Lys Val Met Gly Arg Asn Ala Phe Asp Tyr Trp Gly Gln Gly Thr
            100                 105                 110

Leu Val Thr Ala Ser Ser Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Tyr Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Ser Pro Pro
    210                 215                 220

Thr Pro Asp Thr Val Val Phe Gly Gly Gly Thr Lys Leu Thr Val Leu
225                 230                 235                 240

Gly Ile Ser Ala Met Val Arg Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 11
```

<211> LENGTH: 4
<212> TYPE: PRT
<213> ORGANISM: Artificial Sequence
<220> FEATURE:
<223> OTHER INFORMATION: CDRH3

<400> SEQUENCE: 11

Ser Val Thr Arg
1

<210> SEQ ID NO 12
<211> LENGTH: 5
<212> TYPE: PRT
<213> ORGANISM: Artificial Sequence
<220> FEATURE:
<223> OTHER INFORMATION: CDRH3

<400> SEQUENCE: 12

Thr Ala Ser Ile Leu
1 5

<210> SEQ ID NO 13
<211> LENGTH: 6
<212> TYPE: PRT
<213> ORGANISM: Artificial Sequence
<220> FEATURE:
<223> OTHER INFORMATION: CDRH3

<400> SEQUENCE: 13

Val Met Gly Arg Asn Ala
1 5

<210> SEQ ID NO 14
<211> LENGTH: 6
<212> TYPE: PRT
<213> ORGANISM: Artificial Sequence
<220> FEATURE:
<223> OTHER INFORMATION: CDRL3

<400> SEQUENCE: 14

Arg Gly Leu Ala Arg Pro
1 5

<210> SEQ ID NO 15
<211> LENGTH: 6
<212> TYPE: PRT
<213> ORGANISM: Artificial Sequence
<220> FEATURE:
<223> OTHER INFORMATION: CDRL3

<400> SEQUENCE: 15

Pro Trp His Arg Thr Ser
1 5

<210> SEQ ID NO 16
<211> LENGTH: 6
<212> TYPE: PRT
<213> ORGANISM: Artificial Sequence
<220> FEATURE:
<223> OTHER INFORMATION: CDRL3

<400> SEQUENCE: 16

Pro Pro Thr Pro Asp Thr
1 5

<210> SEQ ID NO 17
<211> LENGTH: 15

<212> TYPE: PRT
<213> ORGANISM: Artificial Sequence
<220> FEATURE:
<223> OTHER INFORMATION: CDRH2

<400> SEQUENCE: 17

Ser Gly Ser Gly Gly Ser Thr Tyr Tyr Ala Asp Ser Val Lys Gly
1 5 10 15

<210> SEQ ID NO 18
<211> LENGTH: 5
<212> TYPE: PRT
<213> ORGANISM: Artificial Sequence
<220> FEATURE:
<223> OTHER INFORMATION: CDRH1

<400> SEQUENCE: 18

Ser Tyr Ala Met Ser
1 5

<210> SEQ ID NO 19
<211> LENGTH: 7
<212> TYPE: PRT
<213> ORGANISM: Artificial Sequence
<220> FEATURE:
<223> OTHER INFORMATION: CDRL2

<400> SEQUENCE: 19

Gly Lys Asn Asn Arg Pro Ser
1 5

<210> SEQ ID NO 20
<211> LENGTH: 11
<212> TYPE: PRT
<213> ORGANISM: Artificial Sequence
<220> FEATURE:
<223> OTHER INFORMATION: CDRL1

<400> SEQUENCE: 20

Gln Gly Asp Ser Leu Arg Ser Tyr Tyr Ala Ser
1 5 10

<210> SEQ ID NO 21
<211> LENGTH: 116
<212> TYPE: PRT
<213> ORGANISM: Artificial Sequence
<220> FEATURE:
<223> OTHER INFORMATION: heavy chain variable region

<400> SEQUENCE: 21

Glu Val Gln Leu Leu Glu Ser Gly Gly Gly Leu Ala Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Val Thr Arg Phe Asp Tyr Trp Gly Gln Gly Thr Leu Val
100 105 110

Thr Val Ser Ser
        115

<210> SEQ ID NO 22
<211> LENGTH: 116
<212> TYPE: PRT
<213> ORGANISM: Artificial Sequence
<220> FEATURE:
<223> OTHER INFORMATION: heavy chain variable region

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ala Ser Ile Leu Asp Tyr Trp Gly Gln Gly Thr Leu Val
            100                 105                 110

Thr Val Ser Ser
        115

<210> SEQ ID NO 23
<211> LENGTH: 118
<212> TYPE: PRT
<213> ORGANISM: Artificial Sequence
<220> FEATURE:
<223> OTHER INFORMATION: heavy chain variable region

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Met Gly Arg Asn Ala Phe Asp Tyr Trp Gly Gln Gly Thr
            100                 105                 110

Leu Val Thr Ala Ser Ser
        115

<210> SEQ ID NO 24
<211> LENGTH: 109
<212> TYPE: PRT
<213> ORGANISM: Artificial Sequence
<220> FEATURE:
<223> OTHER INFORMATION: light chain variable region

<400> SEQUENCE: 24

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Tyr Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Ser Arg Gly Leu Ala Arg Pro
85 90 95

Val Val Val Gly Gly Gly Thr Lys Leu Thr Val Leu Gly
100 105

<210> SEQ ID NO 25
<211> LENGTH: 109
<212> TYPE: PRT
<213> ORGANISM: Artificial Sequence
<220> FEATURE:
<223> OTHER INFORMATION: light chain variable region

<400> SEQUENCE: 25

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Tyr Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Ser Pro Trp His Arg Thr Ser
85 90 95

Val Val Phe Gly Gly Gly Thr Lys Leu Thr Val Leu Gly
100 105

<210> SEQ ID NO 26
<211> LENGTH: 109
<212> TYPE: PRT
<213> ORGANISM: Artificial Sequence
<220> FEATURE:
<223> OTHER INFORMATION: light chain variable region

<400> SEQUENCE: 26

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Tyr Arg Phe Ser Gly Ser
50 55 60

Ser Ser Gly Asn Thr Ala Ser Leu Thr Ile Thr Gly Ala Gln Ala Glu
65 70 75 80

```
Asp Glu Ala Asp Tyr Tyr Cys Asn Ser Ser Pro Pro Thr Pro Asp Thr
                85                  90                  95

Val Val Phe Gly Gly Gly Thr Lys Leu Thr Val Leu Gly
            100                 105


<210> SEQ ID NO 27
<211> LENGTH: 14
<212> TYPE: PRT
<213> ORGANISM: Artificial Sequence
<220> FEATURE:
<223> OTHER INFORMATION: linker

<400> SEQUENCE: 27

Gly Gly Gly Gly Ser Gly Gly Gly Gly Ser Gly Gly Gly Gly
1               5                   10


<210> SEQ ID NO 28
<211> LENGTH: 15
<212> TYPE: PRT
<213> ORGANISM: Artificial Sequence
<220> FEATURE:
<223> OTHER INFORMATION: linker

<400> SEQUENCE: 28

Ser Ser Ser Ser Gly Ser Ser Ser Ser Gly Ser Ser Ser Ser Gly
1               5                   10                  15


<210> SEQ ID NO 29
<211> LENGTH: 158
<212> TYPE: PRT
<213> ORGANISM: Homo sapiens

<400> SEQUENCE: 29

Met Val Arg Ser Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155


<210> SEQ ID NO 30
<211> LENGTH: 234
<212> TYPE: PRT
<213> ORGANISM: Artificial Sequence
<220> FEATURE:
<223> OTHER INFORMATION: hIgG1-Fc tag amino acid sequence
```

<400> SEQUENCE: 30

Ile Ser Ala Met Val Arg Ser Asp Lys Thr His Thr Cys Pro Pro Cys
1 5 10 15

Pro Ala Pro Glu Leu Leu Gly Gly Pro Ser Val Phe Leu Phe Pro Pro
20 25 30

Lys Pro Lys Asp Thr Leu Met Ile Ser Arg Thr Pro Glu Val Thr Cys
35 40 45

Val Val Val Asp Val Ser His Glu Asp Pro Glu Val Lys Phe Asn Trp
50 55 60

Tyr Val Asp Gly Val Glu Val His Asn Ala Lys Thr Lys Pro Arg Glu
65 70 75 80

Glu Gln Tyr Asn Ser Thr Tyr Arg Val Val Ser Val Leu Thr Val Leu
85 90 95

His Gln Asp Trp Leu Asn Gly Lys Glu Tyr Lys Cys Lys Val Ser Asn
100 105 110

Lys Ala Leu Pro Ala Pro Ile Glu Lys Thr Ile Ser Lys Ala Lys Gly
115 120 125

Gln Pro Arg Glu Pro Gln Val Tyr Thr Leu Pro Pro Ser Arg Asp Glu
130 135 140

Leu Thr Lys Asn Gln Val Ser Leu Thr Cys Leu Val Lys Gly Phe Tyr
145 150 155 160

Pro Ser Asp Ile Ala Val Glu Trp Glu Ser Asn Gly Gln Pro Glu Asn
165 170 175

Asn Tyr Lys Thr Thr Pro Pro Val Leu Asp Ser Asp Gly Ser Phe Phe
180 185 190

Leu Tyr Ser Lys Leu Thr Val Asp Lys Ser Arg Trp Gln Gln Gly Asn
195 200 205

Val Phe Ser Cys Ser Val Met His Glu Ala Leu His Asn His Tyr Thr
210 215 220

Gln Lys Ser Leu Ser Leu Ser Pro Gly Lys
225 230

<210> SEQ ID NO 31
<211> LENGTH: 1239
<212> TYPE: DNA
<213> ORGANISM: Artificial Sequence
<220> FEATURE:
<223> OTHER INFORMATION: IEOmAB1-scFv-hTNFa DNA sequence

<400> SEQUENCE: 31
gaggtgcagc tgttggagtc tgggggaggc ttggcacagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaagac acggccgtat attactgtgc gaaatctgtt 300
actcgttttg actactgggg ccagggaacc ctggtcaccg tctcgagtgg tggaggcggt 360
tcaggcggag gtggctctgg cggtggcgga tcgtctgagc tgactcagga ccctgctgtg 420
tctgtggcct tgggacagac agtcaggatc acatgccaag gagacagtct cagaagctat 480
tatgcaagct ggtaccagca gaagccagga caggcccctg tacttgtcat ctatggtaaa 540
aacaaccggc cctcagggat cccataccga ttctctggct ccagctcagg aaacacagct 600
tccttgacca tcactggggc tcaggcggaa gatgaggctg actattactg taactcctct 660

-continued

```
aggggctgg cgcggcccgt ggtagtcggc ggagggacca agctgaccgt cctaggctct    720

tcgtcatcgg gatcttcgtc atccggatct tcgtcatccg ggatggtcag atcatcttct    780

cgaaccccga gtgacaagcc tgtagcccat gttgtagcaa accctcaagc tgaggggcag    840

ctccagtggc tgaaccgccg ggccaatgcc ctcctggcca atggcgtgga gctgagagat    900

aaccagctgg tggtgccatc agagggcctg tacctcatct actcccaggt cctcttcaag    960

ggccaaggct gcccctccac ccatgtgctc ctcacccaca ccatcagccg catcgccgtc   1020

tcctaccaga ccaaggtcaa cctcctctct gccatcaaga gcccctgcca gagggagacc   1080

ccagaggggg ctgaggccaa gccctggtat gagcccatct atctgggagg ggtcttccag   1140

ctggagaagg gtgaccgact cagcgctgag atcaatcggc ccgactatct cgactttgcc   1200

gagtctgggc aggtctactt tgggatcatt gccctgtga                          1239


<210> SEQ ID NO 32
<211> LENGTH: 412
<212> TYPE: PRT
<213> ORGANISM: Artificial Sequence
<220> FEATURE:
<223> OTHER INFORMATION: IEOmAB1-scFv-hTNFa amino acid sequence

<400> SEQUENCE: 32

Glu Val Gln Leu Leu Glu Ser Gly Gly Gly Leu Ala Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Val Thr Arg Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Glu Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Tyr Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Ser Arg Gly Leu Ala
    210                 215                 220

Arg Pro Val Val Val Gly Gly Gly Thr Lys Leu Thr Val Leu Gly Ser
225                 230                 235                 240

Ser Ser Ser Gly Ser Ser Ser Ser Gly Ser Ser Ser Ser Gly Met Val
                245                 250                 255

Arg Ser Ser Ser Arg Thr Pro Ser Asp Lys Pro Val Ala His Val Val
```

```
            260                 265                 270

Ala Asn Pro Gln Ala Glu Gly Gln Leu Gln Trp Leu Asn Arg Arg Ala
        275                 280                 285

Asn Ala Leu Leu Ala Asn Gly Val Glu Leu Arg Asp Asn Gln Leu Val
    290                 295                 300

Val Pro Ser Glu Gly Leu Tyr Leu Ile Tyr Ser Gln Val Leu Phe Lys
305                 310                 315                 320

Gly Gln Gly Cys Pro Ser Thr His Val Leu Leu Thr His Thr Ile Ser
                325                 330                 335

Arg Ile Ala Val Ser Tyr Gln Thr Lys Val Asn Leu Leu Ser Ala Ile
            340                 345                 350

Lys Ser Pro Cys Gln Arg Glu Thr Pro Glu Gly Ala Glu Ala Lys Pro
        355                 360                 365

Trp Tyr Glu Pro Ile Tyr Leu Gly Gly Val Phe Gln Leu Glu Lys Gly
    370                 375                 380

Asp Arg Leu Ser Ala Glu Ile Asn Arg Pro Asp Tyr Leu Asp Phe Ala
385                 390                 395                 400

Glu Ser Gly Gln Val Tyr Phe Gly Ile Ile Ala Leu
                405                 410


<210> SEQ ID NO 33
<211> LENGTH: 1941
<212> TYPE: DNA
<213> ORGANISM: Artificial Sequence
<220> FEATURE:
<223> OTHER INFORMATION: IEOmAB2-scFv-hIgG-hTNFa DNA sequence

<400> SEQUENCE: 33

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaagac acggccgtat attactgtgc gaaaacggct    300

tctattcttg actactgggg ccagggaacc ctggtcaccg tctcgagtgg tggaggcggt    360

tcaggcggag gtggctctgg cggtggcgga tcgtctgagc tgactcagga ccctgctgtg    420

tctgtggcct tgggacagac agtcaggatc acatgccaag gagacagtct cagaagctat    480

tatgcaagct ggtaccagca gaagccagga caggcccctg tacttgtcat ctatggtaaa    540

aacaaccggc cctcagggat cccataccga ttctctggct ccagctcagg aaacacagct    600

tccttgacca tcactggggc tcaggcggaa gatgaggctg actattactg taactcctct    660

ccctggcatc gtactagtgt ggtattcggc ggagggacca agctgaccgt cctaggcata    720

tcggccatgg ttagatctga caaaactcac acatgcccac cgtgcccagc acctgaactc    780

ctggggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gcagccccga gaaccacagg tgtacaccct gcccccatcc   1140

cgggatgagc tgaccaagaa ccaggtcagc ctgacctgcc tggtcaaagg cttctatccc   1200
```

-continued agcgacatcg ccgtggagtg ggagagcaat gggcagccgg agaacaacta caagaccacg 1260
cctcccgtgc tggactccga cggctccttc ttcctctaca gcaagctcac cgtggacaag 1320
agcaggtggc agcaggggaa cgtcttctca tgctccgtga tgcatgaggc tctgcacaac 1380
cactacacgc agaagagcct ctccctgtct ccgggtaaat cttcgtcatc gggatcttcg 1440
tcatccggat cttcgtcatc cgggatggtc agatcatctt ctcgaacccc gagtgacaag 1500
cctgtagccc atgttgtagc aaaccctcaa gctgaggggc agctccagtg gctgaaccgc 1560
cgggccaatg ccctcctggc caatggcgtg gagctgagag ataaccagct ggtggtgcca 1620
tcagagggcc tgtacctcat ctactcccag gtcctcttca agggccaagg ctgcccctcc 1680
acccatgtgc tcctcaccca caccatcagc cgcatcgccg tctcctacca gaccaaggtc 1740
aacctcctct ctgccatcaa gagcccctgc cagagggaga ccccagaggg ggctgaggcc 1800
aagccctggt atgagcccat ctatctggga ggggtcttcc agctggagaa gggtgaccga 1860
ctcagcgctg agatcaatcg gcccgactat ctcgactttg ccgagtctgg gcaggtctac 1920
tttgggatca ttgccctgtg a 1941

<210> SEQ ID NO 34
<211> LENGTH: 646
<212> TYPE: PRT
<213> ORGANISM: Artificial Sequence
<220> FEATURE:
<223> OTHER INFORMATION: IEOmAB2-scFv-hIgG-hTNFa amino acid sequence

<400> SEQUENCE: 34

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Thr Ala Ser Ile Leu Asp Tyr Trp Gly Gln Gly Thr Leu Val
100 105 110

Thr Val Ser Ser Gly Gly Gly Gly Ser Gly Gly Gly Gly Ser Gly Gly
115 120 125

Gly Gly Ser Ser Glu Leu Thr Gln Asp Pro Ala Val Ser Val Ala Leu
130 135 140

Gly Gln Thr Val Arg Ile Thr Cys Gln Gly Asp Ser Leu Arg Ser Tyr
145 150 155 160

Tyr Ala Ser Trp Tyr Gln Gln Lys Pro Gly Gln Ala Pro Val Leu Val
165 170 175

Ile Tyr Gly Lys Asn Asn Arg Pro Ser Gly Ile Pro Tyr Arg Phe Ser
180 185 190

Gly Ser Ser Ser Gly Asn Thr Ala Ser Leu Thr Ile Thr Gly Ala Gln
195 200 205

Ala Glu Asp Glu Ala Asp Tyr Tyr Cys Asn Ser Ser Pro Trp His Arg
210 215 220

Thr Ser Val Val Phe Gly Gly Gly Thr Lys Leu Thr Val Leu Gly Ile

-continued

```
225                 230                 235                 240

Ser Ala Met Val Arg Ser Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Ser Ser Ser Ser Gly Ser Ser
465                 470                 475                 480

Ser Ser Gly Ser Ser Ser Ser Gly Met Val Arg Ser Ser Ser Arg Thr
                485                 490                 495

Pro Ser Asp Lys Pro Val Ala His Val Val Ala Asn Pro Gln Ala Glu
            500                 505                 510

Gly Gln Leu Gln Trp Leu Asn Arg Arg Ala Asn Ala Leu Leu Ala Asn
        515                 520                 525

Gly Val Glu Leu Arg Asp Asn Gln Leu Val Val Pro Ser Glu Gly Leu
    530                 535                 540

Tyr Leu Ile Tyr Ser Gln Val Leu Phe Lys Gly Gln Gly Cys Pro Ser
545                 550                 555                 560

Thr His Val Leu Leu Thr His Thr Ile Ser Arg Ile Ala Val Ser Tyr
                565                 570                 575

Gln Thr Lys Val Asn Leu Leu Ser Ala Ile Lys Ser Pro Cys Gln Arg
            580                 585                 590

Glu Thr Pro Glu Gly Ala Glu Ala Lys Pro Trp Tyr Glu Pro Ile Tyr
        595                 600                 605

Leu Gly Gly Val Phe Gln Leu Glu Lys Gly Asp Arg Leu Ser Ala Glu
    610                 615                 620

Ile Asn Arg Pro Asp Tyr Leu Asp Phe Ala Glu Ser Gly Gln Val Tyr
625                 630                 635                 640

Phe Gly Ile Ile Ala Leu
                645
```

<210> SEQ ID NO 35
<211> LENGTH: 1947
<212> TYPE: DNA
<213> ORGANISM: Artificial Sequence
<220> FEATURE:
<223> OTHER INFORMATION: IEOmAB3-scFv-hIgG-hTNFa DNA sequence

<400> SEQUENCE: 35
gaggtgcagc tgttggagtc tggggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaagac acggccgtat attactgtgc gaaagtgatg 300
ggtcggaatg cttttgacta ctggggccag ggaaccctgg tcaccgcctc gagtggtgga 360
ggcggttcag gcggaggtgg ctctggcggt ggcggatcgt ctgagctgac tcaggaccct 420
gctgtgtctg tggccttggg acagacagtc aggatcacat gccaaggaga cagtctcaga 480
agctattatg caagctggta ccagcagaag ccaggacagg cccctgtact tgtcatctat 540
ggtaaaaaca accggccctc agggatccca taccgattct ctggctccag ctcaggaaac 600
acagcttcct tgaccatcac tggggctcag gcggaagatg aggctgacta ttactgtaac 660
tcctctccgc ccactcctga tacggtggta ttcggcggag ggaccaagct gaccgtccta 720
ggcatatcgg ccatggttag atctgacaaa actcacacat gcccaccgtg cccagcacct 780
gaactcctgg ggggaccgtc agtcttcctc ttccccccaa aacccaagga caccctcatg 840
atctcccgga cccctgaggt cacatgcgtg gtggtggacg tgagccacga agaccctgag 900
gtcaagttca actggtacgt ggacggcgtg gaggtgcata atgccaagac aaagccgcgg 960
gaggagcagt acaacagcac gtaccgtgtg gtcagcgtcc tcaccgtcct gcaccaggac 1020
tggctgaatg gcaaggagta caagtgcaag gtctccaaca aagccctccc agcccccatc 1080
gagaaaacca tctccaaagc caaagggcag ccccgagaac cacaggtgta caccctgccc 1140
ccatcccggg atgagctgac caagaaccag gtcagcctga cctgcctggt caaaggcttc 1200
tatcccagcg acatcgccgt ggagtgggag agcaatgggc agccggagaa caactacaag 1260
accacgcctc ccgtgctgga ctccgacggc tccttcttcc tctacagcaa gctcaccgtg 1320
gacaagagca ggtggcagca ggggaacgtc ttctcatgct ccgtgatgca tgaggctctg 1380
cacaaccact acacgcagaa gagcctctcc ctgtctccgg gtaaatcttc gtcatcggga 1440
tcttcgtcat ccggatcttc gtcatccggg atggtcagat catcttctcg aaccccgagt 1500
gacaagcctg tagcccatgt tgtagcaaac cctcaagctg aggggcagct ccagtggctg 1560
aaccgccggg ccaatgccct cctggccaat ggcgtggagc tgagagataa ccagctggtg 1620
gtgccatcag agggcctgta cctcatctac tcccaggtcc tcttcaaggg ccaaggctgc 1680 cctccaccc atgtgctcct cacccacacc atcagccgca tcgccgtctc ctaccagacc 1740
aaggtcaacc tcctctctgc catcaagagc ccctgccaga gggagacccc agagggggct 1800
gaggccaagc cctggtatga gcccatctat ctgggagggg tcttccagct ggagaagggt 1860
gaccgactca gcgctgagat caatcggccc gactatctcg actttgccga gtctgggcag 1920
gtctactttg ggatcattgc cctgtga 1947

<210> SEQ ID NO 36

-continued

<211> LENGTH: 648
<212> TYPE: PRT
<213> ORGANISM: Artificial Sequence
<220> FEATURE:
<223> OTHER INFORMATION: IEOmAB3-scFv-hIgG-hTNFa amino acid sequence

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Met Gly Arg Asn Ala Phe Asp Tyr Trp Gly Gln Gly Thr
            100                 105                 110

Leu Val Thr Ala Ser Ser Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Tyr Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Ser Pro Pro
    210                 215                 220

Thr Pro Asp Thr Val Val Phe Gly Gly Gly Thr Lys Leu Thr Val Leu
225                 230                 235                 240

Gly Ile Ser Ala Met Val Arg Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380
```

```
Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Ser Ser Ser Ser Gly
465                 470                 475                 480

Ser Ser Ser Ser Gly Ser Ser Ser Ser Gly Met Val Arg Ser Ser Ser
                485                 490                 495

Arg Thr Pro Ser Asp Lys Pro Val Ala His Val Val Ala Asn Pro Gln
            500                 505                 510

Ala Glu Gly Gln Leu Gln Trp Leu Asn Arg Arg Ala Asn Ala Leu Leu
        515                 520                 525

Ala Asn Gly Val Glu Leu Arg Asp Asn Gln Leu Val Val Pro Ser Glu
    530                 535                 540

Gly Leu Tyr Leu Ile Tyr Ser Gln Val Leu Phe Lys Gly Gln Gly Cys
545                 550                 555                 560

Pro Ser Thr His Val Leu Leu Thr His Thr Ile Ser Arg Ile Ala Val
                565                 570                 575

Ser Tyr Gln Thr Lys Val Asn Leu Leu Ser Ala Ile Lys Ser Pro Cys
            580                 585                 590

Gln Arg Glu Thr Pro Glu Gly Ala Glu Ala Lys Pro Trp Tyr Glu Pro
        595                 600                 605

Ile Tyr Leu Gly Gly Val Phe Gln Leu Glu Lys Gly Asp Arg Leu Ser
    610                 615                 620

Ala Glu Ile Asn Arg Pro Asp Tyr Leu Asp Phe Ala Glu Ser Gly Gln
625                 630                 635                 640

Val Tyr Phe Gly Ile Ile Ala Leu
                645
```

<210> SEQ ID NO 37
<211> LENGTH: 1422
<212> TYPE: DNA
<213> ORGANISM: Artificial Sequence
<220> FEATURE:
<223> OTHER INFORMATION: IEOmAB2-scFv-hIgG DNA sequence

<400> SEQUENCE: 37

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaagac acggccgtat attactgtgc gaaaacggct    300

tctattcttg actactgggg ccagggaacc ctggtcaccg tctcgagtgg tggaggcggt    360

tcaggcggag gtggctctgg cggtggcgga tcgtctgagc tgactcagga ccctgctgtg    420

tctgtggcct tgggacagac agtcaggatc acatgccaag gagacagtct cagaagctat    480

tatgcaagct ggtaccagca gaagccagga caggcccctg tacttgtcat ctatggtaaa    540
```

-continued

```
aacaaccggc cctcagggat cccataccga ttctctggct ccagctcagg aaacacagct    600

tccttgacca tcactggggc tcaggcggaa gatgaggctg actattactg taactcctct    660

ccctggcatc gtactagtgt ggtattcggc ggagggacca agctgaccgt cctaggcata    720

tcggccatgg ttagatctga caaaactcac acatgcccac cgtgcccagc acctgaactc    780

ctggggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gcagccccga gaaccacagg tgtacaccct gcccccatcc   1140

cgggatgagc tgaccaagaa ccaggtcagc ctgacctgcc tggtcaaagg cttctatccc   1200

agcgacatcg ccgtggagtg ggagagcaat gggcagccgg agaacaacta caagaccacg   1260

cctcccgtgc tggactccga cggctccttc ttcctctaca gcaagctcac cgtggacaag   1320

agcaggtggc agcaggggaa cgtcttctca tgctccgtga tgcatgaggc tctgcacaac   1380

cactacacgc agaagagcct ctccctgtct ccgggtaaat ga                       1422
```

<210> SEQ ID NO 38
<211> LENGTH: 473
<212> TYPE: PRT
<213> ORGANISM: Artificial Sequence
<220> FEATURE:
<223> OTHER INFORMATION: IEOmAB2-scFv-hIgG amino acid sequence

<400> SEQUENCE: 38

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ala Ser Ile Leu Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Glu Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Tyr Arg Phe Ser
            180                 185                 190

Gly Ser Ser Ser Gly Asn Thr Ala Ser Leu Thr Ile Thr Gly Ala Gln
        195                 200                 205
```

```
Ala Glu Asp Glu Ala Asp Tyr Tyr Cys Asn Ser Ser Pro Trp His Arg
    210                 215                 220

Thr Ser Val Val Phe Gly Gly Gly Thr Lys Leu Thr Val Leu Gly Ile
225                 230                 235                 240

Ser Ala Met Val Arg Ser Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

<210> SEQ ID NO 39
<211> LENGTH: 1428
<212> TYPE: DNA
<213> ORGANISM: Artificial Sequence
<220> FEATURE:
<223> OTHER INFORMATION: IEOmAB3-scFv-hIgG DNA sequence

<400> SEQUENCE: 39

```
gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaagac acggccgtat attactgtgc gaaagtgatg    300

ggtcggaatg cttttgacta ctggggccag ggaaccctgg tcaccgcctc gagtggtgga    360

ggcggttcag gcggaggtgg ctctggcggt ggcggatcgt ctgagctgac tcaggaccct    420

gctgtgtctg tggccttggg acagacagtc aggatcacat gccaaggaga cagtctcaga    480

agctattatg caagctggta ccagcagaag ccaggacagg cccctgtact tgtcatctat    540
```

-continued

```
ggtaaaaaca accggccctc agggatccca taccgattct ctggctccag ctcaggaaac    600

acagcttcct tgaccatcac tggggctcag gcggaagatg aggctgacta ttactgtaac    660

tcctctccgc ccactcctga tacggtggta ttcggcggag ggaccaagct gaccgtccta    720

ggcatatcgg ccatggttag atctgacaaa actcacacat gcccaccgtg cccagcacct    780

gaactcctgg ggggaccgtc agtcttcctc ttccccccaa aacccaagga caccctcatg    840

atctcccgga cccctgaggt cacatgcgtg gtggtggacg tgagccacga agaccctgag    900

gtcaagttca actggtacgt ggacggcgtg gaggtgcata atgccaagac aaagccgcgg    960

gaggagcagt acaacagcac gtaccgtgtg gtcagcgtcc tcaccgtcct gcaccaggac   1020

tggctgaatg gcaaggagta caagtgcaag gtctccaaca aagccctccc agcccccatc   1080

gagaaaacca tctccaaagc caaagggcag ccccgagaac cacaggtgta caccctgccc   1140

ccatcccggg atgagctgac caagaaccag gtcagcctga cctgcctggt caaaggcttc   1200

tatcccagcg acatcgccgt ggagtgggag agcaatgggc agccggagaa caactacaag   1260

accacgcctc ccgtgctgga ctccgacggc tccttcttcc tctacagcaa gctcaccgtg   1320

gacaagagca ggtggcagca ggggaacgtc ttctcatgct ccgtgatgca tgaggctctg   1380

cacaaccact acacgcagaa gagcctctcc ctgtctccgg gtaaatga                 1428
```

ANTIBODIES AGAINST TUMOR-ASSOCIATED ANTIGENS AND METHOD FOR OBTAINING THEM

CROSS-REFERENCE TO RELATED APPLICATIONS

This application is a 371 of PCT/EP2019/066217, filed Jun. 19, 2019, which claims the benefit of European Patent Application No. 18178526.2, filed Jun. 19, 2018.

FIELD OF THE INVENTION

The present invention relates to a method for identifying an immunoglobulin, recombinant or synthetic antigen-binding fragments thereof that present in vivo tumor binding activity and do not significantly cross-react with normal cells and to antibodies thereby obtained and uses thereof.

BACKGROUND OF THE INVENTION

Since the approval of rituximab 20 years ago, antibody-based immunotherapies have dramatically changed the natural history of several cancer types[1,2]. However, due to the difficulty in identifying tumor-associated antigens, only a few antibody-based drugs (21 at the end of 2017), targeting even fewer antigens (13 molecules), have entered into clinical use[3]. Furthermore, more than 50% of the available therapeutic antibodies target only five antigens (CD20, EGFR, HER2, PD-1 and PD-L1), and consequently no targeted immunotherapeutic option exists for the majority of cancer types[4]. Therefore, it has become of pivotal importance to design immunotherapies against novel tumor-associated antigens efficacious in halting currently untreatable tumors. The success of targeted immunotherapies lies in the balance between clinical efficacy, which strictly depends on in vivo accessibility of the target antigen, and toxicity, which instead depends on the preferential or tumor-restricted antigen expression. Indeed, immunotherapies raised against widely expressed antigens or promiscuous epitopes are at risk of high toxicity hindering their clinical efficacy. On the other hand, immunotherapies against highly cancer-specific antigens, which are poorly expressed or inaccessible, show diminished efficacy[5]. Currently available therapeutic-antibodies have been developed starting from fully characterized antigens, whose suitability as molecular targets was based upon in-depth knowledge of their function and their cancer cell-specificity/enrichment. Nowadays, the target-first approaches involve the discovery of tumor-specific antigens from high-throughput RNA- and DNA-sequencing data ([6], [7]), or protein-based methodologies,[8,9,10]. Such strategies allow optimal tumor-antigen specificity due to dataset analyses, however the accessibility of tumor antigens remains uncertain and cannot be easily predicted. Additionally, such approaches cannot accurately predict a variety of post-translational modifications, which can either generate novel tumor-associated epitopes or mask expected antigenicity. The paucity of viable, clinically relevant tumor antigens uncovered by these approaches underscores the difficulty of translating data mining into functional in vivo antigenicity[11]. Alternative to the target-first approach is the antibody-first line of action. This strategy uses unbiased, phenotypic screening to select antibodies against true tumor-associated antigens. In so doing, new antibodies can be selected against cancer cells without prior knowledge of target antigen, using high complexity antibody phage libraries[12]. This approach provides the advantage of immediately generating a viable antibody that can be directly tested in relevant species for specific diseases. Phenotypic screenings can be performed in vitro, with cultured cells, or in vivo, with growing tumors (or in combination). Screening strategies utilizing cultured cells, however, are limited as cells qualitatively and quantitatively change protein expression, especially of membrane proteins, due to their adaptation to in vitro culture conditions[13]. Currently, there are no examples of immunotherapies based on antibodies obtained from in vivo screenings, likely because of their intrinsic complexity. No such selected antibody has entered into clinical trials to gauge efficacy. However, a number of recombinant antibodies raised against purified antigen in vitro are currently under clinical evaluation[14] or in use[15]. In principle, however, antibody selection by in vivo tumor targeting allows for the creation and validation of immunotherapies against bona fide tumor antigens that are accessible in their relevant environmental context.

The International Patent Application WO2010028791 refers to synthetic antibody display library containing human germline antibody molecules with variation in VH CDR3 and VL CDR3 and at position 52 of VH CDR2, for screening and selection of antibody molecules specific for antigens of interest. Said International Patent Application also refers to a method of obtaining one or more antibody molecules able to bind an antigen, the method including bringing into contact a library of antibody molecules according to the invention and said antigen and selecting one or more antibody molecules of the library able to bind said antigen.

The International Patent Application WO2018002952 refers to a naïve antibody phage display library (APDL), a process for producing the same and a method of obtaining manufacturable antibodies as soluble Fabs from the antibody phage display library.

The US Patent Application US2017355750 refers to methods for high-throughput screening of a functional antibody fragment for an immunoconjugate that targets a protein antigen. The method therein described combines a phage-displayed synthetic antibody library and high-throughput cytotoxicity screening of non-covalently assembled immunotoxins or cytotoxic drug to identify highly functional synthetic antibody fragments for delivering toxin payloads.

The International Patent Application WO2017175176 refers to vectors for cloning and expressing genetic material including but not limiting to antibody gene or parts thereof, and methods of generating said vectors. Said vectors express the antibody genes in different formats such as Fab or scFv as a part of intertransfer system, intratransfer system or direct cloning and expression in individual display systems. In particular, phage display technology is therein used to clone and screen potential antibody genes in phagemid which is followed by the transfer of said genes to yeast vector for further screening and identification of lead molecules against antigens.

Bauer et al., The Journal of Immunology, vol. 172, no. 6, 2004.01.01, refer to human anti fibroblast activating protein (FAP) antibody TNF fusions targeting tumor stroma by binding to the FAP antigen and delivering membrane-anchored TNF-α bioactivity. The anti FAP antibody therein described binds tumor stroma cells and doesn't bind tumors cells directly.

Spitaleri et al., Journal of Cancer Research and Clinical Oncology, vol. 139, no. 3, 2013-03, refer to a human monoclonal antibody (L19) fused to TNF. L19 antibody binds to the extra domain B-fibronectin on tumor blood vessels and not directly to tumor cells. The antibody was found to be safe but did not result in objective tumor response.

Hoogenboom et al., Molecular Immunology, vol. 28, no. 9, 1991 Sep. 1, refer to antibody-TNF fusions. The antibody therein used binds to the transferrin receptor. However, said antibody is not specific for tumor cells since transferrin receptor may be present also on normal cells.

Fellermeier et al., Oncoimmunology, vol. 5, no. 11, 2016 Sep. 27, refer to antiEpCAM or FAP scFvs fused to extracellular domain of 4-1BBL, OX40L, GITRL or LIGHT, but not to TNF-α. The anti FAP antibody therein described binds tumor stroma cells and doesn't bind tumors cells directly. EpCAM is expressed on epithelial derived cells, thus an anti EpCAM antibody is not specific for tumor cells.

WO2007128563 refers to fusion protein comprising antibody having specific binding affinity to either extracellular domain of oncofetal fibronectin or to extracellular domains of oncofetal tenascin fused to IL-10, GM-CSF and IL-24, but not to TNF-α. The antibodies L19 and G11 therein used bind to the extra domain B-fibronectin on tumor blood vessels or tenascin around vascular structures in the tumor stroma. Therefore, the fusion protein therein disclosed does not bind directly to tumor cells.

Sanchez-Martin et al., Trends in Biotechnology, vol 33, no. 5, 2015 May 1, refer to methods for selecting anti-tumor antibodies. In particular, FIG. 2 represents a method to isolate tumor-homing antibodies, the method consisting of a step of pre-enrichment of the initial phage repertoire on cell suspensions from freshly excided tumors (ex vivo strategy) followed by injection of the resulting enriched library into tumor-bearing mice (in vivo strategy). Kurosawa G. et al., Cancer Science, vol. 102, no. 1, 2010 Oct. 12 refer to in vitro selection of anti-cancer antibodies from a phage library using human tumor cell lines. Alfaleh M. A. et al., Antibodies vol. 6, no. 3, 10, 2017 Aug. 5, refer to method of selecting membrane specific antibodies from phage display libraries with cell-based panning. WO2006017173 refers to methods of identification of anti-cancer antibodies comprising collecting the antiserum from patients immunized with a cancer cell and eliminating antibodies binding to human red and white blood cells. The international application also refers to a method comprising a phage displayed antibody library using cells collected from subjects immunized with cancer cells; removing members of the library that bind to human red blood cells to generate a sub-library and recovering from the sub-library members that display antibodies that bind to the cancer cell. WO2006017173 therefore only describes in vitro selection of phage antibodies. None of such documents disclose the combination of in vivo and ex vivo rounds of selection of phages from a library respectively in healthy mice and healthy cells to remove phages binding to healthy tissue in order to provide a phage library depleted of healthy tissue binding phages to be used in further in vivo and ex vivo rounds of phage selection in mice bearing tumors or in tumor cells. Moreover, it is therein not disclosed the further testing of in vivo anti-tumor efficacy (e.g. by testing specificity, localization, distribution, cytotoxicity, protection against pathology, . . . ).

Therefore, there is still the need for a rapid method to select antibodies that directly bind tumor cells in vivo that could be harnessed in the context of any neoplasia, thus providing antibodies able to selectively bind to tumor cells and not to normal cells and to efficiently treat tumors.

SUMMARY OF THE INVENTION

The generation of antibodies versus tumor-associated antigens constitutes a hurdle to the availability of immunotherapies against all cancers. Here, inventors describe an antibody-screening strategy against tumors growing in immune-competent mice, including steps to exclude healthy tissue antigens. In particular, the present method may be applied also to chemotherapy-resistant and/or relapsed T-cell acute lymphoblastic leukemia (T-ALL) and inventors herein show e.g. that the method can be successfully applied, in addition to untreated tumors, also to chemo-resistant and relapsed Patient derived xenografts (PDX). As a way of example, inventors found that the procedure yielded in vivo targeting binders cytotoxic against murine and human T-ALL when fused to TNFα. Strikingly, inventors found cross-reactivity to tumors of neuro-ectodermal origin among which inventors show in vivo efficacy versus patient derived xenografts of metastatic melanoma. Whilst antibody-TNFα immuno-cytokines directly killed T-ALL cells in vitro and in vivo, melanomas were successfully treated through the modulation of host inflammation. The workflow herein presented can be harnessed in the context of any neoplasia. The antibodies according to the invention have the advantage of directly binding the tumor. Therefore, the present antibodies may directly kill tumor cells by means of immune system activation and/or can also be effective by the bystander effect. Indeed, by binding tumor cells, the present antibodies may induce the death of stromal cells or other adjacent not bound cells.

DETAILED DESCRIPTION OF THE INVENTION

Inventors have adapted and streamlined an antibody-screening strategy against tumor cells growing in immune-competent animals, which incorporates in vivo and ex vivo library-depletion steps to counter-select antigens expressed on healthy tissues. Such workflow can be tailored and applied to virtually any tumor model and allows to identify novel immunotherapies through the in vivo selection of specificity and evaluation of tumoricidal efficacy. As such, the platform described herein provides a rational, high-throughput, rapid workflow to discover and pre-clinically validate treatment options for the benefit of patients. As a proof-of-principle, inventors in particular set out to isolate antibodies targeting T-cell acute lymphoblastic leukemia (T-ALL) including human relapsed and/or chemotherapy-resistant T-ALL. While chemotherapeutic treatment of T-ALL induces robust survival in ~90% of pediatric cases[16], overall survival is only 40% in adults[17] and 5% for refractory or relapsing patients due to the absence of efficacious second line treatments[18, 19]. Thus, novel immunotherapies against relapsed chemo-resistant T-ALL would provide an essential option to otherwise untreatable patients.

It is therefore an object of the present invention a method for identifying an immunoglobulin, recombinant or synthetic antigen-binding fragments thereof that present in vivo tumor binding activity and do not significantly cross-react with normal cells comprising the steps of:

(a) recovery of tumor cell bound phages from a sample isolated from a subject affected by a cancer wherein said subject has been administered with a depleted first phage library, wherein said depleted first phage library comprises a plurality of phage-displayed synthetic single-chain variable fragments (scFv) that do not bind significantly in vivo and ex vivo to antigens expressed on normal cells, thereby obtaining a first enriched phage library and/or (b) depletion from the obtained first enriched phage library of phages that bind ex vivo antigens expressed on normal cells thereby obtaining a depleted first enriched phage library and/or (c) recovery of tumor cell bound phages from a sample isolated from a subject affected by a cancer wherein said subject has been administered with the depleted first enriched phage library, thereby obtaining a second enriched phage library and/or (d) identification from the second enriched phage library of scFv having in vitro and in vivo tumor specificity. Said library is preferably human.

Preferably, the method according to the invention comprises the above steps (a), (b), (c) and (d). Any order of the above steps may be possible, however in a preferred embodiment, the steps (a), (b), (c) and (d) are sequentially performed.

Preferably, the identified immunoglobulin, recombinant or synthetic antigen-binding fragments thereof binds directly to tumor cell.

The depleted first phage library of step a) is preferably obtained by previously depleting it:

a) of phages that bind in vivo to cells of subjects not presenting tumors and b) of phages that bind ex vivo to normal cells.

Preferably, in the method of the invention said depleted first phage library is obtained by removing cell bound phages from a sample isolated from a subject not affected by a cancer wherein said subject has been administered with a first phage library to recover unbound phages and/or depletion from said unbound phages of phages that bind ex vivo antigens expressed on normal cells thereby obtaining a depleted first phage library.

Preferably, in the method of the invention said depleted first phage library is obtained by removing cell bound phages from a sample isolated from a subject not affected by a cancer wherein said subject has been administered with a first phage library to recover unbound phages and depletion from said unbound phages of phages that bind ex vivo antigens expressed on normal cells thereby obtaining a depleted first phage library.

The above “sample isolated from a subject affected by a cancer” may be e.g. any sample containing tumor cells as e.g. infiltrated spleen. The above “sample isolated from a subject not affected by a cancer” may be e.g. any sample comprising normal cells, preferably a heart blood sample.

In the context of the present invention, the term “do not significantly cross-react with normal cells” or “do not bind significantly in vivo and ex vivo to antigens expressed on normal cells” or “do not bind significantly to normal cells” indicates that the antibodies bind to tumor cells as opposed to normal cells preferably with at least 1.5, more preferably 2.5, fold greater mean fluorescence intensity or percent positivity as assessed by flow cytometry.

In a more preferred embodiment, the identified immunoglobulin, recombinant or synthetic antigen-binding fragments thereof bind at least 20% of the tumor cells and/or bind to tumor cells as opposed to normal cells with at least about 1.5, preferably at least about 2.5, fold greater affinity or avidity and/or bind to tumor cells as opposed to normal cells with at least about 1.5, preferably at least about 2.5, fold greater mean fluorescence intensity or percent positivity as assessed by flow cytometry.

In the context of the present invention a “normal cell” is a cell which is not a cancer cell. A “normal cell” may be a cell from any tissue, except for cells of thymus.

Preferably, the unbound phages and/or phages of the first depleted phage library and/or of the depleted first enriched phage library and/or of the first and/or second enriched phage library are amplified in bacterial host cells after recovery. In particular, the unbound phages isolated after in vivo phage library depletion on healthy subjects and the bound phages isolated after phage recovery from the subject sample are amplified in bacteria.

Preferably, the step d) comprises a competitive in vitro single scFv clone binding analysis to tumor versus normal cells, preferably by flow cytometry, to select in vitro tumor specific immunoglobulin, recombinant or synthetic antigen-binding fragments thereof.

Preferably, the step d) comprises a selection of specific and/or effective clones in vivo. The scFv-phage clones are e.g. selected for in vivo localization and/or efficacy in a subject affected by a cancer wherein said subject has been administered with scFv-phage clones.

Preferably, the selected phages were used to carry out phage infection. Then phage clones were picked and grown to mid-log phase and scFv production was induced, e.g. in the presence of IPTG. In a preferred embodiment of the method as above defined the subject is an animal, preferably a mouse. When the subject is affected by a cancer the subject is preferably a syngeneic murine T-ALL disease model (mT-ALL) or a murine model of other tumors. However, in principle any tumor animal model may be used, e.g. models of different leukemia, of subcutaneous solid tumors such as melanoma, breast or lung carcinoma.

Another object of the invention is an immunoglobulin, recombinant or synthetic antigen-binding fragments thereof that presents in vivo tumor binding activity and does not significantly cross-react with normal cells obtainable by the method as above defined. Preferably said immunoglobulin, recombinant or synthetic antigen-binding fragments thereof binds directly to tumor cell. Preferably, the immunoglobulin, recombinant or synthetic antigen-binding fragments thereof as above defined comprises at least one heavy chain complementary determining region (CDRH3) amino acid sequence having at least 80% identity to an amino acid sequence selected from the group consisting of: SEQ ID NO:11 (SVTR), SEQ ID NO:12 (TASIL) and SEQ ID NO: 13 (VMGRNA) and/or at least one light complementary determining region (CDRL3) amino acid sequence having at least 80% identity to an amino acid sequence selected from the group consisting of: SEQ ID NO: 14 (RGLARP), SEQ ID NO: 15 (PWHRTS) and SEQ ID NO: 16 (PPTPDT). Another object of the invention is an immunoglobulin, recombinant or synthetic antigen-binding fragments thereof that presents in vivo tumor binding activity and does not significantly cross-react with normal cells comprising at least one heavy chain complementary determining region (CDRH3) amino acid sequence having at least 80% identity to an amino acid sequence selected from the group consisting of: SEQ ID NO:11 (SVTR), SEQ ID NO:12 (TASIL) and SEQ ID NO: 13 (VMGRNA) and/or comprising at least one light complementary determining region (CDRL3) amino acid sequence having at least 80% identity to an amino acid sequence selected from the group consisting of: SEQ ID NO: 14 (RGLARP), SEQ ID NO: 15 (PWHRTS) and SEQ ID NO: 16 (PPTPDT).

Preferably said CDRH3 comprises the sequence aa. 99-102 of SEQ. ID NO: 2 (SVTR) or aa. 99-103 of SEQ. ID NO: 4 (TASIL) or and aa. 99-104 of SEQ ID NO: 6 (VMGRNA).

Preferably said CDRL3 comprises the sequence aa. 221-226 of SEQ. ID NO: 2 (RGLARP) or aa. 221-226 of SEQ. ID NO: 4 (PWHRTS) or aa. 223-228 of SEQ ID NO: 6 (PPTPDT).

The immunoglobulin, recombinant or synthetic antigen-binding fragments thereof according to the invention preferably comprise: a) a CDRH3 amino acid sequence having at least 80% identity to an amino acid sequence of SEQ. ID NO: 11 (SVTR) and a CDRL3 amino acid sequence having at least 80% identity to an amino acid sequence of SEQ ID NO: 14 (RGLARP) or b) a CDRH3 amino acid sequence having at least 80% identity to an amino acid sequence of SEQ. ID NO: 12 (TASIL) and a CDRL3 amino acid sequence having at least 80% identity to an amino acid sequence of SEQ ID NO: 15 (PWHRTS) or c) a CDRH3 amino acid sequence having at least 80% identity to an amino acid sequence of SEQ ID NO: 13 (VMGRNA) and a CDRL3 amino acid sequence having at least 80% identity to an amino acid sequence of SEQ ID NO: 16 (PPTPDT).

Preferably, the immunoglobulin, recombinant or synthetic antigen-binding fragments thereof according to the invention further comprise a heavy chain complementary determining region (CDRH2) amino acid sequence having at least 80% identity to SEQ ID NO: 17 (SGSGGSTYYADSVKG) and/or a heavy chain complementary determining region (CDRH1) amino acid sequence having at least 80% identity to SEQ ID NO: 18 (SYAMS) and/or a light chain complementary determining region (CDRL2) amino acid sequence having at least 80% identity to SEQ ID NO: 19 (GKNNRPS) and/or a light chain complementary determining region (CDRL1) amino acid sequence having at least 80% identity to SEQ ID NO: 20 (QGDSLRSYYAS). Preferably, the immunoglobulin, recombinant or synthetic antigen-binding fragments thereof according to the invention comprise the complementarity determining regions (CDRs) amino acid sequence having at least 80% identity to SEQ ID NO: SEQ ID NOs: 11, 14, 17-20, or to SEQ ID NOs: 12, 15, 17-20 or to SEQ ID NOs: 13, 16, 17-20.

More preferably, the immunoglobulin, recombinant or synthetic antigen-binding fragments thereof according to the invention comprise the complementarity determining regions (CDRs) set forth in SEQ ID NOs: 11, 14, 17-20, or the complementarity determining regions (CDRs) set forth in SEQ ID NOs: 12, 15, 17-20 or the complementarity determining regions (CDRs) set forth in SEQ ID NOs: 13, 16, 17-20.

More preferably, the immunoglobulin, recombinant or synthetic antigen-binding fragments thereof according to the invention comprise a heavy chain variable region (VH) amino acid sequence having at least 80% identity to the amino acid sequence selected from the group consisting

```
                                    SEQ ID NO: 21
(EVQLLESGGGLAQPGGSLRLSCAASGFTFSSYAMSWVRQAPGKGLEWVSA

ISGSGGSTYYADSVKGRFTISRDNSKNTLYLQMNSLRAEDTAVYYCAKSVT

RFDYWGQGTLVTVSS),

                                    SEQ ID NO: 22
(EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKTAS

ILDYWGQGTLVTVSS),
```

-continued

```
                                    SEQ ID NO: 23
(EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKVMG

RNAFDYWGQGTLVTASS)
```

or fragments thereof and/or a light chain variable region (VL) amino acid sequence having at least 80% identity to the amino acid sequence selected from the group consisting of:

```
                                    SEQ ID NO: 24
(SSELTQDPAVSVALGQTVRITCQGDSLRSYYASWYQQKPGQAPVLVIYGK

NNRPSGIPYRFSGSSSGNTASLTITGAQAEDEADYYCNSSRGLARPVVVGG

GTKLTVLG),

                                    SEQ ID NO: 25
(SSELTQDPAVSVALGQTVRITCQGDSLRSYYASWYQQKPGQAPVLVIYGK

NNRPSGIPYRFSGSSSGNTASLTITGAQAEDEADYYCNSSPWHRTSVVFGG

GTKLTVLG),

                                    SEQ ID NO: 26
(SSELTQDPAVSVALGQTVRITCQGDSLRSYYASWYQQKPGQAPVLVIYGK

NNRPSGIPYRFSGSSSGNTASLTITGAQAEDEADYYCNSSPPTPDTVVFGG

GTKLTVLG)
```

or fragments thereof.

In a preferred embodiment, the immunoglobulin, recombinant or synthetic antigen-binding fragments thereof comprise a heavy chain variable region amino acid sequence having at least 80% identity to SEQ ID NO: 21 and a light chain variable region amino acid sequence having at least 80% identity to SEQ ID NO: 24 or a heavy chain variable region amino acid sequence having at least 80% identity to SEQ ID NO: 22 and a light chain variable region amino acid sequence having at least 80% identity to SEQ ID NO: 25 or a heavy chain variable region amino acid sequence having at least 80% identity to SEQ ID NO: 23 and a light chain variable region amino acid sequence having at least 80% identity to SEQ ID NO: 26.

Preferably, the VH and the VL of said immunoglobulin, recombinant or synthetic antigen-binding fragments are linked by an amino acid linker, said linker preferably consisting of a sequence of from 15 aa to 19 aa which is not subjected to intracellular cleavage by proteases, more preferably the linker comprises or consists of the sequence set forth in SEQ ID NO: 27 (GGGGSGGGGSGGGG). Preferably the VH is linked by its C-terminus to the N-terminus of the VL.

In a preferred embodiment, the immunoglobulin, recombinant or synthetic antigen-binding fragments thereof as above defined further comprise an IgG-Fc tag, preferably a human IgG1-Fc tag, more preferably comprising or consisting of a sequence having at least 80% identity to SEQ ID NO: 30.

The term "Fc tag" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

In a preferred embodiment of the invention, the immunoglobulin, recombinant or synthetic antigen-binding fragments thereof comprise or consist of a sequence having at least 80% identity to SEQ ID NO:2, SEQ ID NO:4, SEQ ID NO:6, SEQ ID NO: 38 or SEQ ID NO:10, more preferably of a sequence selected from the group consisting of: SEQ ID NO:2, SEQ ID NO:4, SEQ ID NO:6, SEQ ID NO: 38 and SEQ ID NO:10, In a preferred embodiment, the immunoglobulin, recombinant or synthetic antigen-binding fragments thereof as above defined bind directly to tumor cell.

Preferably the immunoglobulin, recombinant or synthetic antigen-binding fragments thereof according to the invention is fused to at least one molecule selected from the group consisting of: pro-inflammatory cytokine, preferably of the TNF family, more preferably TNF, and TNF related molecules (es. TRAIL), IFNs (alfa, beta or gamma), interleukins and functional fragments and derivatives thereof and/or radionuclides or domains able to recruit radio/chemotherapy compounds, bacterial and fungine toxins, chemotherapeutic agents, enzymes, other domains mediating the attachment of the antibody to the plasma membrane or to vesicles derived from a cell or artificial source, fluorophores, markers.

More preferably the TNF is human TNF$\alpha$, even more preferably comprising a sequence encoded by SEQ ID NO: 8 or comprising a sequence having at least 80% identity to SEQ ID NO:29, ore preferably comprising or consisting of the sequence set forth in SEQ ID NO:29, or functional fragments or derivatives thereof.

In a preferred embodiment of the invention, the molecule as above defined is linked to the VH or the IgG-Fc tag of the immunoglobulin recombinant or synthetic antigen-binding fragments, preferably to the C-terminus of the VH or of the IgG-Fc tag, by an amino acid linker, said linker preferably consisting of a sequence of from 15 aa to 19 aa which is not subjected to intracellular cleavage by proteases, more preferably the linker comprises or consists of the sequence set forth in in SEQ ID NO: 28 (SSSSGSSSSGSSSSG)

In a preferred embodiment, the immunoglobulin, recombinant or synthetic antigen-binding fragments thereof as above defined is fused to human TNF-$\alpha$.

In a preferred embodiment, the immunoglobulin, recombinant or synthetic antigen-binding fragments thereof as above defined bind to at least 20% of murine T-ALL blasts (FITC+) and/or to at least 50% of a human T-ALL cell line and/or exhibit at least 2.5-fold stronger signal on tumor than normal cells.

Preferably, the immunoglobulin, recombinant or synthetic antigen-binding fragments thereof as above defined comprises the complementarity determining regions (CDRs) set forth in SEQ ID NOs: 11, 14, 17-20.

More preferably, the immunoglobulin, recombinant or synthetic antigen-binding fragments thereof comprise a VH amino acid sequence having at least 80% identity to SEQ ID NO: 21 and a VL amino acid sequence having at least 80% identity to SEQ ID NO: 24, even more preferably the immunoglobulin, recombinant or synthetic antigen-binding fragments thereof comprise a VH amino acid sequence set forth in SEQ ID NO: 21 and a VL amino acid sequence set forth in SEQ ID NO: 24.

Preferably, the immunoglobulin, recombinant or synthetic antigen-binding fragments thereof comprise the complementarity determining regions (CDRs) set forth in SEQ ID NOs: 12, 15, 17-20. More preferably, said immunoglobulin, recombinant or synthetic antigen-binding fragments thereof comprise a VH amino acid sequence having at least 80% identity to SEQ ID NO: 22 and a VL amino acid sequence having at least 80% identity to SEQ ID NO: 25, even more preferably said immunoglobulin, recombinant or synthetic antigen-binding fragments thereof comprise a VH amino acid sequence set forth in SEQ ID NO: 22 and a VL amino acid sequence set forth in SEQ ID NO: 25.

Preferably, the immunoglobulin, recombinant or synthetic antigen-binding fragments thereof comprise the complementarity determining regions (CDRs) set forth in SEQ ID NOs: 13, 16, 17-20. More preferably, said immunoglobulin, recombinant or synthetic antigen-binding fragments thereof comprise a VH amino acid sequence having at least 80% identity to SEQ ID NO: 23 and a VL amino acid sequence having at least 80% identity to SEQ ID NO: 26, even more preferably said immunoglobulin, recombinant or synthetic antigen-binding fragments thereof comprise a VH amino acid sequence set forth in SEQ ID NO: 23 and a VL amino acid sequence set forth in SEQ ID NO: 26.

More preferably, the immunoglobulin, recombinant or synthetic antigen-binding fragments thereof according to the invention comprise a sequence having a % of identity of at least 80% with a sequence selected from the group consisting of: SEQ ID NO:32, 34 and 36.

A further object of the invention is an immunoglobulin, recombinant or synthetic antigen-binding fragments thereof with in vivo tumor binding activity, and which do not bind normal cells, preferably as above defined.

The immunoglobulin, recombinant or synthetic antigen-binding fragments as above defined are preferably for medical use, more preferably for use in the prevention and/or treatment of cancer, wherein said cancer is preferably selected from the group consisting of:

T-cell acute lymphoblastic leukemia (T-ALL), preferably chemotherapy-resistant and/or relapsed and/or refractory tumors, tumors of embryonic/neuroectodermal origin, preferably melanomas, including metastatic melanoma, brain tumor, Ewing's sarcomas, glioblastoma, testicular carcinoma, embryonal carcinomas, embryonal ovarian carcinoma, primitive neuroectodermal tumors, neuroblastoma, retinoblastoma, osteosarcoma, astrocytoma, glioma, medulloblastoma.

The present immunoglobulin, recombinant or synthetic antigen-binding fragments are also for use in a method of delivering a molecule as defined above, preferably TNF-$\alpha$, to tumor cells in a patient. The immunoglobulin, recombinant or synthetic antigen-binding fragments according to the invention is preferably systemically or locally administered, preferably by intravenous injection. Another object of the invention is an in vitro or ex-vivo method for diagnosing and/or assessing the risk of developing and/or prognosing and/or for monitoring the progression and/or for monitoring the efficacy of a therapeutic treatment and/or for the screening of a therapeutic treatment of a tumor or metastasis in a subject and/or for selecting patients to be subjected to a specific treatment and/or for target identification and/or target validation comprising the steps of:

a) detecting a tumor cell in a sample isolated from the subject with the immunoglobulin, recombinant or synthetic antigen-binding fragments thereof as defined above,
b) comparing with respect to a proper control and/or reference.

Further object of the invention is a pharmaceutical composition comprising at least one immunoglobulin, recombinant or synthetic antigen-binding fragments thereof as above defined and at least one pharmaceutically acceptable excipient.

Other objects of the invention are a nucleic acid molecule encoding the immunoglobulin, recombinant or synthetic antigen-binding fragments thereof as above defined, or hybridizing with said nucleic acid, or a degenerate sequence thereof; an expression vector comprising the nucleic acid as above defined; a host cell that produces the immunoglobulin, recombinant or synthetic antigen-binding fragments thereof as above defined or comprising said vector; a method for producing the immunoglobulin, recombinant or synthetic antigen-binding fragments thereof as above defined comprising culturing said host cell under conditions for expression of the immunoglobulin, recombinant or synthetic antigen-binding fragments thereof and optionally recovering the immunoglobulin, recombinant or synthetic antigen-binding fragments thereof from the cell culture. Preferably the above defined nucleic acid molecule has or comprises the nucleotide sequence set forth in SEQ ID NO: 3, 5, 7, 31, 33, 35, 37 or 39.

A further object of the invention is a kit comprising at least one immunoglobulin, recombinant or synthetic antigen-binding fragments thereof as defined above and optionally detecting means, wherein said kit is preferably for the diagnosis of tumors and/or metastases, preferably said tumors being chemotherapy-resistant and/or relapsed and/or refractory tumors.

Another object of the invention is a method of treating and/or preventing a cancer or metastasis comprising administering a therapeutically effective amount of the immunoglobulin, recombinant or synthetic antigen-binding fragments thereof as defined above or the pharmaceutical composition as above defined above or the host cells as defined above or the nucleic acid as above defined or the vector as above defined.

Other type of binding library may be used in the present method, e.g. a DNA or RNA aptamers library.

The step d) of the method according to the invention may also comprise selecting antibody with tumor specificity in vivo by in vivo treatment of animal presenting tumor with candidate antibody phage, preferably by phage accumulation assay.

In the context of the present invention a "normal cell" is intended as a cell which is not affected by cancer and is not a tumor cell (herein also defined as a healthy cell). Said "normal cell" is not a thymus cell.

While the present invention focuses on the above antibodies, as an exemplification of the present invention, one of ordinary skill in the art will appreciate that, once given the present disclosure, other similar antibodies, and antibody fragments thereof, as well as antibody fragments of these similar antibodies may be produced and used within the scope of the present invention. Such similar antibodies may be produced by a reasonable amount of experimentation by those skilled in the art. The present method may allow patient stratification e.g. by IHC or tumor detection by in vivo imaging. The present antibodies can also be used for diagnostic and/or target identification and/or target validation uses. In an object of the present invention the diagnostic use can be applied as non-exclusive example to diagnostic imaging in vivo in patients. The term immunoglobulin also includes phage antibody clone. In a particular embodiment of the invention, all the antibodies were initially tested in flow cytometry reactions containing 50% murine TALL blasts and 50% normal healthy murine blood nucleated cells. The scFv selected according to the present method preferably binds to at least about 20% of the mT-ALL tumor, with preferably at least about 2.5-fold greater positivity or fluorescence signal as compared to the healthy cells. More preferably, said scFv preferably binds to at least about 50% of a human T-ALL cell line when tested singularly by flow cytometry.

When tested against normal mouse tissues, the antibodies of the invention preferably do not significantly cross-react with healthy cells. The antigen of the antibodies of the invention is therefore predominantly or preferentially expressed upon the surface of tumor cells. Alternatively, the antibodies of the invention bind to healthy tissues that are not essential for survival.

The immunoglobulin, recombinant or synthetic antigen-binding fragments thereof or the phage antibody clone according to the invention is preferably specific for T-cell acute lymphoblastic leukemia (T-ALL), preferably chemotherapy-resistant and/or relapsed and/or refractory tumors, tumors of embryonic/neuroectodermal origin, preferably melanomas, including metastatic melanoma, brain tumor, Ewing's sarcomas, and malignant embryonal carcinoma.

In the present invention the term "immunoglobulin, recombinant or synthetic antigen-biding fragments thereof" also includes bivalent small immune proteins, dia-tria-tetrabodies, bispecific scFvs with a second scFv (es. anti-CD3), CAR-T of any kind (any generation and any configuration, es. tandem, conditional, split, inducible etc.).

The antibodies according to the invention may also be fused or conjugated with immunoglobulins or immunoglobin regions (IgG vs IgM vs IgA vs IgD vs IgE, rat versus human versus murine, etc, hIgG1 vs hIgG3 vs hIgG4 etc), radionuclides or domains able to recruit radio/chemotherapy compounds, bacterial and fungine toxins, chemotherapeutic agents, enzymes, other domains mediating the attachment of the antibody to the plasma membrane or to vesicles derived from a cell or artificial source, fluorophores, markers (e.g. that can be used in the diagnosis of tumors, as e.g. gadolinium, iron or manganese particles in MRI, or markers for heat induced tumoricidal therapy (as gold or iron) that can be excited in a reactive way to treat the tumour).

Other objects of the invention are an expression vector encoding the immunoglobulin, recombinant or synthetic antigen-binding fragments thereof as above defined, an isolated host cell comprising the nucleic acid as above defined, preferably producing the immunoglobulin, recombinant or synthetic antigen-binding fragments thereof as above defined.

A nucleic acid molecule that codes for the antibody according to the invention or its fragments, derivatives or conjugates according to the present invention can be generated using technologies that are known in the art, such as gene synthesis or PCR amplification. The nucleic acid molecule can be cloned into an expression vector, with the recombinant DNA techniques that are known in the art. A vector for the expression of the antibodies or their derivatives or conjugates according to the present invention can be inserted into host cell lines, for example by transfection. Methods of transfection are known and kits for transfection can be purchased from commercial sources (e.g., Stratagene, La Jolla, CA). Transfectants that stably express the antibodies or their derivatives or conjugates according to the present invention can be selected according to techniques known in the art. Different clones of these transfectants can then be isolated and cultured, and the expression levels of each clone (amount of antibody or derivative secreted in the supernatant) can be quantified according to techniques known in the art. One example is the competitive binding to cells that express the antigen, in the presence of known amounts of fluorophore-labelled antibody or derivative; the fluorescent signal measured for example by flow cytometry according to techniques known in the art is inversely proportional to the amount of antibody or derivative produced by the clone in question. In this way a person skilled in the art can obtain cell lines that stably produce the antibodies or their derivatives in sufficient quantities for subsequent use, for example the production of a drug, and can validate quantitatively the production capacity of such cell line.

Cells that produce the antibodies or their derivatives or conjugates according to the present invention can be grown in media and culture conditions known in the art so as to maximize production. The antibodies or their derivatives or conjugates according to the present invention can be purified by one skilled in the art using known processes, for example binding to protein A or to new synthetic materials, which can be arranged in a column or on a membrane, said purification being in batch or continuous. Production, purification and subsequent analytical control can also take place according to "Good Manufacturing Practices" GMP, known in the art, in accordance with the requirements that must be satisfied during the development, production and control of medicines for use in humans.

In the context of the present invention the molecules defined as "hIgG-IEOmAb-hTNFα" correspond to the molecules defined as "hIgG-IEOmAB-scFv-hTNFα" or "IEOmAB-hIgG-scFv-hTNFα". Therefore, e.g., the expression "hIgG-IEOmAb2-hTNFα" and "hIgG-IEOmAB2-scFv-hTNFa" or "IEOmAB2-hIgG-scFv-hTNFα" are herein exchangeable. The order of the term "hIgG", "scFv", "IEOmAB" in the definition of the molecules of the invention may be changed without affecting the nature of the molecule.

Moreover, in the definition of the herein described molecule, the term "scFv" may be present or not without any effect on the nature of molecule, e.g. in the context of the present invention the molecule defined as "IEOmAB1-scFv-hTNFα" is the same as "IEOmAB1-hTNFα", the molecule defined as "IEOmAB-scFv" correspond to the molecule defined as "IEOmAB", e.g., the molecule "IEOmAB1-scFv" corresponds to the molecule "IEOmAB1".

Also the term "hT-ALL binding immune-cytokine" corresponds to the term "immune-cytokine". Derivatives of antibodies according to the present invention, such as functional fragments, or conjugates with biologically active molecules (eg toxins), or with radioisotopes, fluorescent dyes, enzymes that can be detected by chemiluminescence, can be obtained using chemical or genetic engineering procedures known in the art.

The antibodies and their derivatives or conjugates according to the present invention, in particular conjugates with radioactive isotopes or fluorescent or chemiluminescent tracers, can be used in imaging diagnostics of patients using technologies and procedures known in the art. The signal generated by the conjugated antibodies that bind the target in vivo is a specific indicator of antigen localization and can be revealed and quantified by tomographic instruments that are known in the art. The process for the preparation of the antibody of the invention is within the skills of the man skilled in the art and comprises cultivating host cells that have been transfected with a vector for the expression of the antibody and isolating the antibody according to standard procedures.

As far as the industrial aspects of the present invention are concerned, the antibody herein disclosed shall be suitably formulated in pharmaceutical compositions as normally done in this technical field. The antibodies of the present invention may comprise at least one CDRH as defined above that contains one or more amino acid substitutions, deletions or insertions of no more than 4 amino acids, preferably of no more than 2 amino acids. The antibodies of the present invention may further comprise at least one CDRL as defined above that contains one or more amino acid substitutions, deletions or insertions of no more than 4 amino acids, preferably of no more than 2 amino acids.

The immunoglobulin, recombinant or synthetic antigen-binding fragments or the nucleic acid molecule or the expression vector or the host cell according to the invention are for medical use. The definition of fragment, derivative or conjugate of an antibody according to the invention, includes a scFv, a Fv fragment, a Fab fragment, a F(ab)2 fragment, a bifunctional hybrid antibody, a multimeric antibody, a derivative that contains biologically active molecules, including a member of the avidin family or a growth factor that can stimulate immunological effectors, or a pharmacologically active molecule, including a toxin, a cytokine, or any other molecule that is able to increase the therapeutic effect, an immunoconjugate, for example with radioactive isotopes, fluorescent tracers, enzymes for chemiluminescence, cytokines or toxins, including enzymatically active toxins of bacterial, fungal, vegetal or animal origin and fragments thereof.

Preferably, the immunoglobulin according to the invention is selected from the group consisting of an intact immunoglobulin, a Fv, a scFv (single chain Fv fragment), a Fab, a F(ab')2, an "antibody-like" domain, an "antibody-mimetic domain", a single antibody domain (VH domain or VL domains). The antibody like domain comprises binding proteins structurally related to antibodies such as Tcell receptors.

The term "antibody mimetics" refers to those organic compounds that are not antibody derivatives but that can bind specifically an antigen like antibodies do. They include anticalins, DARPins, affibodies, affilins, affimers, affitins, alphabodies, avimers, fynomers, monobodies and others. The single antibody domain is also called Nanobody (VH domain or VL domains).

Further object of the invention is an isolated nucleic acid molecule encoding the immunoglobulin, recombinant or synthetic antigen-binding fragments thereof as defined above or hybridizing with said nucleic acid, or a degenerate sequence thereof. Preferably, said nucleic acid molecule has sequence having at least 80% identity to the nucleotide sequence of SEQ ID NOs: 3, 5, 7, 31, 33, 35, 37 or 39 or fragments thereof.

The present invention also provides antibodies, or derivatives thereof, with high affinity and directed against distinct portions or specific forms of post-translational modification of the target, such antibodies comprising heavy chain and light chain variable regions as above defined, combined with sequences of human immunoglobulins (IgM, IgD, IgG, IgA, IgE) coding for peptides that do not induce immune response in human.

In a preferred aspect of the invention the variable regions of the heavy chains and light chains have been joined to a gamma-1 (G1) heavy chain constant region of human immunoglobulins (Ig) (preferably represented by an aa. sequence encoded by SEQ ID NO:9 or comprising or consisting of SEQ ID NO:30 or derivatives or fragments thererof), for the production of a chimeric antibody. Other objects of the invention are an isolated nucleic acid molecule encoding the immunoglobulin, recombinant or synthetic antigen-binding fragments thereof as above defined, or hybridizing with said nucleic acid, or a degenerate sequence thereof, an expression vector encoding the immunoglobulin, recombinant or synthetic antigen-binding fragments thereof as above defined, an isolated host cell comprising the nucleic acid as above defined, said cell preferably producing the immunoglobulin, recombinant or synthetic antigen-binding fragments thereof as above defined. Another object of the invention is the immunoglobulin, recombinant or synthetic antigen-binding fragments of the invention or the nucleic acid molecule of the invention or the expression vector of the invention or the host cell of the invention for medical use. The herein mentioned or reported polynucleotide and polypeptide also includes derivatives and functional fragments thereof. The molecules herein mentioned also includes corresponding orthologous or homologous genes, isoforms, variants, allelic variants, functional derivatives, functional fragments thereof. The herein mentioned protein or polypeptide include also the corresponding protein encoded from a corresponding orthologous or homologous genes, functional mutants, functional derivatives, functional fragments or analogues, isoforms thereof. The term "analogue" as used herein referring to a protein means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. A "derivative" may be a nucleic acid molecule, as a DNA molecule, coding the polynucleotide as above defined, or a nucleic acid molecule comprising the polynucleotide as above defined, or a polynucleotide of complementary sequence. In the context of the present invention the term "derivatives" also refers to longer or shorter polynucleotides and/or polypeptides having e.g. a percentage of identity of at least 41%, 50%, 60%, 65%, 70% or 75%, more preferably of at least 85%, as an example of at least 90%, and even more preferably of at least 95% or 100% with the sequences herein mentioned or with their complementary sequence or with their DNA or RNA corresponding sequence. The term "derivatives" and the term "polynucleotide" also include modified synthetic oligonucleotides. The modified synthetic oligonucleotide are preferably LNA (Locked Nucleic Acid), phosphoro-thiolated oligos or methylated oligos, morpholinos, 2'-O-methyl, 2'-O-methoxyethyl oligonucleotides and cholesterol-conjugated 2'-O-methyl modified oligonucleotides (antagomirs). The term "derivative" may also include nucleotide analogues, i.e. a naturally occurring ribonucleotide or deoxyribonucleotide substituted by a non-naturally occurring nucleotide. The term "derivatives" also includes nucleic acids or polypeptides that may be generated by mutating one or more nucleotide or amino acid in their sequences, equivalents or precursor sequences. The term "derivatives" also includes at least one functional fragment of the polynucleotide. In the context of the present invention "functional" is intended for example as "maintaining their activity", e.g. a TNF-α functional fragment or derivative is able to either: i) mediate direct TNFα-dependent cell cytotoxicity or; ii) act as a chemoattractant molecule to favor the invasion of tumors by inflammatory immune cells or; iii) to favor pro-inflammatory signaling within a tumor in order to create a microenvironment unfavorable for tumor growth conditions by stimulating tumor vasculature, tumor-resident immune cells, tumor-resident stromal cells or the self-same tumor cells. In the context of the present invention, the term "cancer" or "tumor" includes e.g. leukemia, glioblastoma, lymphomas, blood cell cancers, tumors of embrionic/neuroectodermal origin, preferably brain tumor, melanoma, Ewing's sarcomas, and malignant embryonal carcinoma, more preferably metastatic melanoma, breast cancer, colon cancer, pancreatic cancer, preferably T-cell acute lymphoblastic leukemia (T-ALL), more preferably chemotherapy-resistant and/or relapsed and/or refractory tumors. The "tumors" are preferably chemotherapy-resistant and/or relapsed and/or refractory tumors. Another object of the invention is a method of producing the immunoglobulin as above defined comprising culturing the cell that produces the immunoglobulin of the invention and recovering the immunoglobulin, recombinant or synthetic antigen-binding fragments thereof from the cell culture. Another object of the invention is a pharmaceutical composition comprising at least one immunoglobulin, recombinant or synthetic antigen-biding fragments thereof or nucleic acid molecule according to the invention and pharmaceutically acceptable excipients. Preferably, said composition is for use as systemic and local treatment, preferably for intravenous, intratumoral, intraperitoneal, intramuscular, topic and intranasal administration. Systemic is by far the most relevant route, especially when hematological or metastatic cancers are treated. However, protocols using local treatments (e.g. radiotherapy) are also known to elicit a systemic immunological response (Abscopal effect). Intraperitoneal and intravenous administration are e.g. preferred for the immunocytokine format of the present antibodies, as the other routes provided slower uptake and would have had more deleterious, local effects. Unconjugated antibodies can be given by any of the above administration routes. In the context of the present invention local treatment comprises also the use on single metastasis of e.g. melanoma. In the herein described screening procedure to select the antibodies according to the invention, the production of phage from bacteria and their use ex vivo is preferably carried out by intravenous or intra-tumor administration. In the case of nucleic acid molecule, the administration may be by gene therapy by ex vivo genetic modification of cells or by direct infection of tissue cells in the organism, using viral vectors or other gene delivery methods.

In the present invention, the above-mentioned linker preferably consists of a sequence of from 15aa to 19aa which is not subjected to intracellular cleavage by proteases. Preferably the linker between the VH and the VL has a sequence of SEQ ID NO: 27 (GGGGSGGGGSGGGG) (G4SG4SG4). Preferably the linker between VL and TNF-α or between hIgG-Fc tag and TNF-α has a sequence of SEQ ID NO: 28 (SSSSGSSSSGSSSSG) (S4GS4GS4G). All the variants in nucleotide sequence (according to genetic code) that produce the same protein sequences will work equally as linker. It is also an object of the invention a method of treating and/or preventing a cancer or metastasis comprising administering a therapeutically effective amount of the immunoglobulin or fragment or derivative or conjugate thereof or cellular composition or viral particle or host cells or nucleic acids as above defined. The method for treating or preventing a cancer or metastasis, comprises administering to a patient in need thereof an effective amount of at least one immunoglobulin, fragments or derivatives or conjugates thereof or cellular composition or viral particle or host cells or nucleic acids as described above. In some aspects, the invention comprises a method for treating or preventing tumors and/or metastasis in a subject, the method comprising administering to a subject in need thereof an effective amount of at least one immunoglobulin, fragments or derivatives or conjugates thereof or cellular composition or viral particle or host cells or nucleic acids of the invention simultaneously or sequentially with an anti-cancer agent. Preferably, the above tumor is a chemotherapy-resistant and/or relapsed and/or a refractory tumor.

Nucleic acids encoding immunoglobulins may be obtained from libraries encoding a multiplicity of such molecules. For example, phage display libraries of immunoglobulin molecules are known and may be used in this process. Advantageously, the library encodes a repertoire of immunoglobulin molecules. A "repertoire" refers to a set of molecules generated by random, semi-random or directed variation of one or more template molecules, at the nucleic acid level, in order to provide a multiplicity of binding specificities. Methods for generating repertoires are well characterized in the art. It is another object of the invention a pharmaceutical composition comprising at least one immunoglobulin, antibody, recombinant or synthetic antigen-binding fragments thereof as described above and pharmaceutically acceptable excipients, preferably for use in systemic, local, intraperitoneal, intramuscular or intranasal administration.

The composition comprises an effective amount of the immunoglobulin, antibody, recombinant or synthetic antigen-binding fragments thereof. Pharmaceutical compositions are conventional in this field and can be made by the person skilled in the art just based on the common general knowledge. For sake of brevity, the preferred antibody according to the present invention shall be identified with the name IEOmAB1 (comprising SEQ ID NO: 2), IEOmAB2 (comprising SEQ ID NO:4) and IEOmAB3 (comprising SEQ ID NO:6).

Still preferably, the antibody, immunoglobulin, recombinant or synthetic antigen-biding fragments thereof is a scFv, Fv fragment, a Fab fragment, a F(ab)2 fragment, a multimeric antibody, a peptide or a proteolytic fragment containing the epitope binding region.

It is a further object of the present invention a nucleic acid encoding the immunoglobulin, recombinant or synthetic antigen-biding fragments thereof, the antibody or functional derivatives thereof of the invention (e.g. effector domains for protein degradation, imaging, catalysis and also genetic tags, binding switches, localization peptides) or hybridizing with the above nucleic acid or consisting of a degenerated sequence thereof.

The process for the preparation of the antibody is within the skills of the man skilled in the art and comprises cultivating host cell and isolating the antibody according to standard procedures.

The antibodies of the present invention may comprise at least one of the sequence as herein defined that contains one or more amino acid substitutions, deletions or insertions, preferably of no more than 16 amino acids, more preferably of no more than 8 amino acids. Said antibodies must retain the ability to bind to their epitope.

The antibodies of the invention may be for medical use. Preferably, they are for use in the treatment of cancer. The present antibodies can also be used for diagnostic and/or target identification and/or target validation uses.

The terms "antibody" and "immunoglobulin" can be herein used interchangeably and are used in the broadest sense and encompass various antibodies and antibody mimetics structures, including but not limited to monoclonal antibodies, polyclonal antibodies, multispecific antibodies (e.g., bispecific antibodies), chimeric antibodies, nanobodies, antibody derivatives, antibody fragments, anticalins, DARPins, affibodies, affilins, affimers, affitins, alphabodies, avimers, fynomers, monobodies and other binding domains or antibody fragments or derivatives, so long as they exhibit the desired antigen-binding activity.

The term immunoglobulin also includes "conjugate" thereof. In the context of the present invention "conjugate" in relation to the antibody of the invention includes antibodies (or fragments thereof) conjugated with a substance (a compound, etc.) having a therapeutic activity, e.g. antitumor activity and/or cell-killing activity or a cytotoxic agents such as various A chain toxins, ribosomes inactivating proteins, and ribonucleases; bispecific antibodies designed to induce cellular mechanisms for killing tumors (see, for example, U.S. Pat. Nos. 4,676,980 and 4,954,617).

The conjugate may be formed by previously preparing each of the aforementioned antibody molecule and the aforementioned substance having anti-tumor activity and/or cell-killing activity, separately, and then combining them (immunoconjugate) or by ligating a protein toxin used as such a substance having anti-tumor activity and/or cell-killing activity to an antibody gene on a gene according to a genetic recombination technique, so as to allow it to express as a single protein (a fusion protein) (immunotoxin).

An "antibody fragment" refers to a molecule other than an intact antibody that comprises a portion of an intact antibody that binds the antigen to which the intact antibody binds. Said fragments are preferably functional.

Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. VH or VL Fvs are also called "Nanobodies".

The term "antibody mimetics" refers to those organic compounds or binding domains that are not antibody derivatives but that can bind specifically an antigen like antibodies do. They include anticalins, DARPins, affibodies, affilins, affimers, affitins, alphabodies, avimers, fynomers, monobodies and others.

The term "chimeric" antibody refers to an antibody in which a portion of the heavy and/or light chain is derived from a particular source or species, while the remainder of the heavy and/or light chain is derived from a different source or species.

The terms "full length antibody," "intact antibody," and "whole antibody" are used herein interchangeably to refer to an antibody having a structure substantially similar to a native antibody structure or having heavy chains that contain an Fc region.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Percent (%) of amino acid sequence identity" or "% identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical composition" refers to a preparation which is in such form as to permit the biological activity of an active ingredient contained therein to be effective, and which contains no additional components which are unacceptably toxic to a subject to which the formulation would be administered. The pharmaceutical composition of the present invention can be administered in the form of a dosage unit, for example tablets or capsules, or a solution.

In the present invention the term "effective amount" shall mean an amount which achieves a desired effect or therapeutic effect as such effect is understood by those of ordinary skill in the art. In the present invention, the antibody may be administered simultaneously or sequentially with another therapeutic treatment, that may be a chemotherapy or radiotherapy.

The invention provides formulations comprising a therapeutically effective amount of an antibody as disclosed herein, and preferably a buffer maintaining the pH in the range from about 4.5 to about 8.5, and, optionally, a surfactant.

The formulations are typically for an antibody as disclosed herein, recombinant or synthetic antigen-binding fragments thereof of the invention as active principle concentration from about 0.01 mg/ml to about 100 mg/ml or from about 1-100 mg/kg body weight for nude antibodies and from about 0.05-50 mg/kg body weight for conjugated antibodies. In certain embodiments, the antibody, recombinant or synthetic antigen-binding fragments thereof concentration is from about 0.1 mg/ml to 1 mg/ml; preferably from 1 mg/ml to 10 mg/ml, preferably from 10 to 100 mg/ml. Therapeutic formulations of the antibody/antibodies can be prepared by mixing the antibody having the desired degree of purity with optional physiologically acceptable carriers, excipients or stabilizers (Remington's Pharmaceutical Sciences 16th edition, Osol, A. Ed., 1980), in the form of lyophilized formulations or aqueous solutions.

Pharmaceutical compositions containing the antibody or immunoglobulin, recombinant or synthetic antigen-biding fragments thereof of the present invention may be manufactured by processes well known in the art, e.g., using a variety of well-known mixing, dissolving, granulating, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen. Parenteral routes are preferred in many aspects of the invention.

For injection, including, without limitation, intravenous, intramuscular and subcutaneous injection, the compounds of the invention may be formulated in aqueous solutions, preferably in physiologically compatible buffers such as physiological saline buffer or polar solvents including, without limitation, a pyrrolidone or dimethylsulfoxide.

Formulations for injection may be presented in unit dosage form, e.g. in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water-soluble form, such as, without limitation, a salt of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxyl ethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl-methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

For administration by inhalation, the antibody of the present invention can conveniently be delivered in the form of an aerosol spray using a pressurized pack or a nebulizer and a suitable propellant. The antibody may also be formulated in rectal compositions such as suppositories or retention enemas, using, e.g., conventional suppository bases such as cocoa butter or other glycerides.

In addition to the formulations described previously, the antibody or immunoglobulin, recombinant or synthetic antigen-biding fragments thereof may also be formulated as depot preparations. Such long acting formulations may be administered by implantation (for example, subcutaneously or intramuscularly) or by intramuscular injection. The compounds of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Additionally, the antibody may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed.

Other delivery systems such as liposomes and emulsions can also be used.

A therapeutically effective amount refers to an amount of compound effective to prevent, alleviate or ameliorate cancer or cancer recurrence symptoms. Determination of a therapeutically effective amount is well within the capability of those skilled in the art, especially in light of the disclosure herein.

For any antibody or immunoglobulin, recombinant or synthetic antigen-biding fragments thereof used in the methods of the invention, the therapeutically effective amount can be estimated initially from in vitro assays. Then, the dosage can be formulated for use in animal models so as to achieve a circulating concentration range that includes the effective dosage. Such information can then be used to more accurately determine dosages useful in patients.

The amount of the composition that is administered will depend upon the parent molecule included therein. Generally, the amount used in the treatment methods is that amount which effectively achieves the desired therapeutic result in mammals. Naturally, the dosages of the various compounds can vary somewhat depending upon the compound, rate of in vivo hydrolysis, etc. In addition, the dosage, of course, can vary depending upon the dosage form and route of administration.

The range set forth above is illustrative and those skilled in the art will determine the optimal dosing of the compound selected based on clinical experience and the treatment indication. Moreover, the exact formulation, route of administration and dosage can be selected by the individual physician in view of the patient's condition and of the most effective route of administration (e.g., intravenous, subcutaneous, intradermal). Additionally, toxicity and therapeutic efficacy of the antibody and other therapeutic agent described herein can be determined by standard pharmaceutical procedures in cell cultures or experimental animals using methods well-known in the art.

It is contemplated that the treatment will be given for one or more cycles until the desired clinical and biological result is obtained. The exact amount, frequency and period of administration of the compound of the present invention will vary, of course, depending upon the sex, age and medical condition of the patient as well as the severity and type of the disease as determined by the attending clinician.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". The vector for use according to the invention is preferably a nanoparticle, a liposome, an exosome, or a viral vector, preferably an adenoviral vector, a herpetoviral vector, a lentiviral vector, a gammaretroviral vector, an adeno-associated vector (AAV), or a vector with a naked DNA plasmid. Preferably said vector is for use in the gene therapy.

The invention also provides a host cell as described above transformed with a vector as described above. The invention further provides a cellular composition comprising at least 50% of the cells as defined above, a viral particle for medical use, preferably for use in the treatment and/or prevention of a cancer, comprising the immunoglobulin, recombinant or synthetic antigen-biding fragments thereof or the vector as described above. The invention further provides the immunoglobulin, recombinant or synthetic antigen-binding fragments thereof, the nucleic acid, the vector, the host cell, the cellular composition or the viral particle as defined above in combination with at least one therapeutic treatment.

Different immunoglobulin, recombinant or synthetic antigen-binding fragments thereof as above defined may also be used in combination.

Preferably the therapeutic treatment is selected from the group consisting of radiotherapy or chemotherapy. The immunoglobulin, the nucleic acid, the vector, the host cell, the cellular composition or the viral particle for use as defined above may also be used in combination with the anti-angiogenic agent or anti-viral agent. The invention further provides a pharmaceutical composition comprising the vector as described above or the host cell as described above or the viral particle as described above or the cellular composition as described above and at least one pharmaceutically acceptable excipient, preferably for medical use, more preferably in the treatment and/or prevention of a cancer. Preferably the pharmaceutical composition further comprises at least one therapeutic agent, as e.g. cancer drugs (such as 5-fluorouracil (5-FU), 6-mercaptopurine (6-MP), Capecitabine (Xeloda®), Cytarabine (Ara-C®), Floxuridine, Fludarabine, Gemcitabine (Gemzar®), Hydroxyurea, Methotrexate, Pemetrexed (Alimta®), Taxanes: paclitaxel (Taxol®) and docetaxel (Taxotere®), Epothilones: ixabepilone (Ixempra®), Vinca alkaloids: vinblastine (Velban®), vincristine (Oncovin®), and vinorelbine (Navelbine®), Estramustine (Emcyt®), Prednisone, Methylprednisolone (Solumedrol®), Dexamethasone (Decadron®), Monoclonal antibody therapy, such as rituximab (Rituxan®) and alemtuzumab (Campath®), Non-specific immunotherapies and adjuvants (other substances or cells that boost the immune response), such as BCG, interleukin-2 (IL-2), and interferon-alfa, Immunomodulating drugs, such as thalidomide and lenalidomide (Revlimid®)). Preferably, in the vector as described above, the polynucleotide is under the control of a promoter capable of efficiently expressing said polynucleotide or polypeptide.

The vector according to the invention can comprise, in the 3'UTR of the transgene, miRNA-responsive modules which destabilise the resulting mRNA in undesirable cell types, for example in order to obtain a selective expression in the tumour stem cell compartment.

In the vector, the polynucleotide sequence, preferably a DNA sequence, is operatively tied to an appropriate sequence of control of the expression (promoter) for directing the synthesis of mRNA. As examples of promoters inventors can mention the immediate promoter of the early genes of cytomegalovirus (CMV), HSV thymidine kinase, early and late SV40 and retroviral LTRs. The vectors can also contain one or more selectable gene markers.

The cells of the invention also comprise "genetically engineered host cells" which are host cells that have been transduced, transformed or transfected with the polynucleotide or with the vector as described above. As examples of appropriate host cells, it can be mentioned bacterial cells, fungal and yeast cells, insect cells, plant cells and animal cells, preferably cancer cells, or cells derived from biopsies. The introduction of the previously described nucleotide molecules or vector into the host cell can be achieved using methods known to the person skilled in the art, such as, for example, calcium phosphate transfection, DEAE-dextran mediated transfection, electroporation, lipofection, microinjection, viral infection, thermal shock, cell fusion . . . the previously described polynucleotide or vector can be introduced into the cancer cells of the patient using exosomes from engineered autologous cells or artificial nanoparticles or self-complementary adenoassociated viruses.

Suitable routes of administration of the pharmaceutical composition of the invention include, for example, oral, intranasal and parenteral administration. . . . Other methods of administration include injection, viral transfer, the use of liposomes, artificial nanoparticles, exosomes from engineered autologous cells and oral intake. The exosomes from engineered autologous cells or artificial nanoparticles or self-complementary adenoassociated viruses can be functionalised if necessary in order to pass through the blood-brain barrier following intravenous administration.

In another aspect, the antibody or derivatives thereof comprises a heavy chain variable domain (VH) sequence (or a VL sequence) having at least 80%, 85%, 90%, 91%, 92%, 93%, 94%, 95%, 96%, 97%, 98%, 99%, or 100% sequence identity to an amino acid sequence selected from the group of: of SEQ ID No: 21-26. In certain embodiments, the VH sequence (or the VL sequence) having at least 80%, 85%, 90%, 91%, 92%, 93%, 94%, 95%, 96%, 97%, 98%, or 99% identity to the above-mentioned sequences contains substitutions (e.g., conservative substitutions), insertions, or deletions relative to the reference sequence, but the antibody comprising that sequence retains the ability to bind the tumor cells.

In the present invention, "at least 80% sequence identity" means that the identity may be at least 80% or at least 85% or 90% or 91% or 92% or 93% or 94% or 95% or 96% or 97% or 98% or 99% or 100% sequence identity to referred sequences.

The term "immunoglobulin" refers to any moiety capable of binding a target, in particular a member of the immunoglobulin superfamily, including T-cell receptors and antibodies. It includes any fragment of a natural immunoglobulin which is capable of binding to a target molecule, for example antibody fragments such as Fv (also called "Nanobodies") and scFv. The term "target" includes antigens, which may be targets for antibodies, T-cell receptors, or other immunoglobulin.

The term "immunoglobulin" or "antibody", in this document, also refers to antibody mimetic molecules, which even if structurally unrelated to immunoglobulins, are able to exert binding of a desired target upon artificial generation of antibody mimetic libraries. They include anticalins, DARPins, affibodies, affilins, affimers, affitins, alphabodies, avimers, fynomers, monobodies and others.

Preferably, the immunoglobulin is an antibody and the target is an antigen. "Antibody" explicitly includes antibody fragments.

Antibodies, as used herein, refer to complete antibodies or antibody fragments capable of binding to a selected target, and including Fv, ScFv, Fab' and F(ab')2, monoclonal and polyclonal antibodies, engineered antibodies including chimeric, CDR-grafted and humanized antibodies, and artificially selected antibodies produced using phage display or alternative techniques. Small fragments, such as Fv and ScFv, possess advantageous properties for diagnostic and therapeutic applications on account of their small size and consequent superior tissue distribution. Preferably, the antibody is a single chain antibody or scFv.

The antibodies according to the invention are especially indicated for diagnostic and therapeutic applications, target validation studies. Accordingly, they may be altered antibodies comprising an effector protein such as a toxin or a label, or an enzyme. Especially preferred are labels which allow the imaging of the distribution of the antibody in vivo. Effector groups may be added prior to the selection of the antibodies by the method of the present invention, or afterwards. Recombinant DNA technology may be used to improve the antibodies of the invention.

The term "antibody library" refers to a collection of antibodies and/or antibody fragments displayed for screening and/or combination into full antibodies. The antibodies and/or antibody fragments may be displayed on a ribosome; on a phage; or on a cell surface, in particular a yeast cell surface.

As used herein, the term "single-chain variable fragment" or "scFv" is a fusion protein comprising the variable regions of the heavy (VH) and light chains (VL) of an immunoglobulin, in which the VH and VL are covalently linked to form a VH:VL heterodimer. The VH and VL are either joined directly or joined by a peptide-encoding linker, which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL-encoding sequences.

The method for diagnosis of tumor according to the present invention is characterized in that it comprises allowing the aforementioned antibodies of the present invention to react with a sample collected from a living body (hereinafter referred to as a biological sample), and detecting a signal(s) of the reacted antibody.

The antibody of the present invention is allowed to react with a biological sample, and a signal of the reacted antibody is then detected, so as to detect a tumor. The obtained antibody signal can be used as an indicator of the amount of an antigen in the biological sample. In detection of a tumor using the antibody of the present invention, first, a biological sample collected as an analyte from a subject, such as a tissue section or blood used as a test target, is allowed to bind to the antibody of the present invention by an antigen-antibody reaction. Subsequently, based on the measurement results of the amount of the bound antibody, the amount of an antigen of interest contained in the biological sample is measured. This measurement may be carried out in accordance with known immunoassay methods. For example, an immunoprecipitation method, an immunoagglutination method, radioimmunoassay, immunonephelometry, a Western blot method, flow cytometry and the like can be used. In radioimmunoassay, a labeled antibody is used, and thus an antibody signal is expressed as the amount of the labeled antibody that is directly detected. Otherwise, an antibody whose concentration or antibody titer has been known may be used as a standard solution, and thus a signal of the target antibody may be expressed as a relative value. That is, both the standard solution and the analyte may be measured using a measurement device, and an antibody signal in a biological sample may be expressed as a value relative to the value of the standard solution used as a criterion. Examples of such radioimmunoassay include the ELISA method, the EI method, the RIA method, fluorescence immunoassay (FIA), and luminescence immunoassay. Of these, the ELISA method is particularly preferable in that it is simple and highly sensitive.

In the present invention, the state of a tumor can be evaluated or diagnosed, using the detection result obtained by the aforementioned detection method as an indicator. For example, when the detection result exceeds a proper control or reference, the state of a tumor is defined as tumor positive, and when the detection result is less than the proper control or reference, it is defined as tumor negative. The term "the state of a tumor" is used herein to mean the presence or absence of the development of a tumor, or the progression degree thereof. Thus, specific examples of the state of a tumor include the presence or absence of the development of a tumor, the progression degree thereof, the degree of malignancy, the presence or absence of metastasis, and the presence or absence of recurrence.

In the aforementioned evaluation, as a state of a tumor to be evaluated, only one state may be selected from the aforementioned examples, or multiple examples may be combined and selected. The presence or absence of a tumor can be evaluated by determining whether or not the tumor has been developed, with reference to the predetermined standard value used as a boundary, based on the obtained detection result. The degree of malignancy is used as an indicator that indicates the progression degree of a cancer. Based on the detection result, the target tumor can be classified into a certain disease stage and it can be evaluated. Otherwise, an early cancer and an advanced cancer can be distinguished from each other, and then they can be evaluated. For example, it is also possible to determine the target tumor as an early cancer or an advanced cancer, using the detection result as an indicator. The metastasis of tumor can be evaluated by determining whether or not neoplasm has appeared at a site apart from the position of the initial lesion, using the detection result as an indicator. The recurrence can be evaluated by determining whether or not the detection result has exceeded the predetermined standard value again after interval stage or remission.

The antibody of the present invention can be provided in the form of a kit for detecting or diagnosing a tumor. The kit of the present invention may comprise a labeling substance, a solid-phase reagent on which the antibody or the labeled antibody has been immobilized, etc., as well as the aforementioned antibody. A labeling substance that labels the antibody means a substance labeled with an enzyme, a radioisotope, a fluorescent compound, a chemiluminescent compound, etc. The kit of the present invention may also comprise other reagents used for carrying out the detection of the present invention, in addition to the aforementioned constitutional elements. For example, when such a labeling substance is an enzyme labeling substance, the kit of the present invention may comprise an enzyme substrate (a chromogenic substrate, etc.), an enzyme substrate-solving solution, an enzyme reaction stop solution, a diluent used for analytes, etc. Moreover, the present kit may further comprise various types of buffers, sterilized water, various types of cell culture vessels, various types of reactors (an Eppendorf tube, etc.), a blocking agent (a serum component such as bovine serum albumin (BSA), skim milk, or goat serum), a washing agent, a surfactant, various types of plates, an antiseptic such as sodium azide, an experimental operation manual (instruction), etc. The kit of the present invention can be effectively used to carry out the aforementioned detection method of the present invention. The kit of the invention optionally comprises control means that can be used to compare the amount or the increase of amount of the antibody as above defined to a value from a control sample. The value may be obtained for example, with reference to known standard, either from a normal subject or from normal population.

The term "sample" with respect to a patient or subject encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like.

The "detecting means" as above defined are preferably at least one antibody, functional analogous or derivatives thereof, or an enzyme substrate. Said antibody, functional analogous or derivatives thereof are specific for said antibody.

In a preferred embodiment, the kit of the invention comprises:

a solid phase adhered antibody specific for said antibody;

detection means of the ligand specific-antibody complex.

The kits according to the invention can further comprise customary auxiliaries, such as buffers, carriers, markers, etc. and/or instructions for use.

The antibodies taught by the present invention or their derivatives can be fused to sequences, single residues or synthetic molecules (tags) that allow antibody purification by affinity chromatography. The tags utilized can be used as detection molecules or indicators (e.g., radioisotopic or fluorescent tags) or enzymatic tags able to catalyze a detectable substrate modification, both for diagnostic use in the lab and for imaging. The diagnostic techniques that can be utilized are for example optical, confocal, multiple foton and electronic microscopy, ELISA, Western blotting, immunoprecipitation, radioimmunological techniques and similar others.

The antibodies defined in the present invention can be used for the preparation of compositions for the detection of neoplasias, including in vivo tumor imaging. The antibodies can be linked to radioactive isotopes or fluorescent tracers, e.g. quantum dots or organic chromophores or enzymes which can be detected by chemiluminescence. The signal originated by labelled antibodies is detectable by scanners or tomography instrumentation, according to the principles of currently used advanced equipment such as TAC/PET.

The present antibodies are therefore useful as an indication of a tumor status.

The present invention will be described by means of non-limiting examples referring to the following figures:

FIG. 1 Schematic representation of scFv-phage selection and screening platform A detailed description is given in the material and methods section.

FIG. 2 Candidate T-ALL binding scFv cross-react with human samples and therapeutically delay tumor progression in vivo. a Flow cytometric determination of cross-reactivity of *E. coli*-produced candidate scFv clones and a naïve negative control scFv versus human T-ALL cell lines (CEM (American Type Cell Culture Collection (ATCC), CCL-119), DND41 (DSMZ, ACC525), Jurkat (ATCC, TIB-152) and TALL-1 (DSMZ, ACC-521)) via detection of the in-frame myc epitope tag; b Flow cytometric determination of cross-reactivity of 293T-produced scFv candidates versus hT-ALL PDX cells as detected by in-frame myc epitope tag (IEOmAB1) or hIgG1-domain (T2D3, IEOmAB2, naïve).; c, d & e: 24 hours post-intravenous injection of $10^{11}$ of the indicated phage clones into mT-ALL bearing mice with palpable splenomegaly c) gross spleen weight; d) splenic-resident mT-ALL blasts (CD4/CD8-double positive as judged by flow cytometry; e) spleen-cell bound/localized phage clones obtained from 1000 counted spleen cells, via infection of TG1-*E. Coli*; f & g: therapeutic efficacy of IEOmAB1-phage against mT-ALL. Mice (n=4 per group) were injected intravenously twice per week with 1011 naïve or IEOmAB1 phage from 2 days post-transplant to day 50 (12 injections total). f) Flow cytometric determination of human CD45+ cells in peripheral blood mononuclear cell fractions 30 days post-transplant; g) Kaplan-Meier survival curve analysis of the same. Each symbol in c, d & f represents an individual mouse, with horizontal lines indicating mean values with error bars displaying +/−s.d. and significance calculated by two-tailed Mann-Whitney tests. Significance of Kaplan Meier curve in g judged by two-tailed log-rank Mantel-Cox tests.

FIG. 3 IEOmAB1-hTNFa immune-cytokine protein delays growth of hT-ALL in vivo and increases time-to-sacrifice a. Flow cytometric analysis of human CD45 positive cells present in the spleens of NSG mice bearing full-blown #03008 hT-ALL PDX, 24 hours post-injection with either negative control (naïve)-hTNFα or IEOmAB1-hTNFα protein (n=3 mice/group). b &c Therapeutic treatment of NSG mice bearing #03008 hT-ALL PDX tumors from 2 days post-transplant, with PBS (n=4), naïve-hTNFα (n=7) or IEOmAB1-hTNFa (n=6) every 2 days intravenously; b) Flow cytometrically determined percentage of human CD45-positive cells in the peripheral blood mononuclear cell fraction 33 days post transplant; c) Kaplan-Meier survival curve analysis of the same mice, receiving 12 intravenous injections of the indicated proteins; d & e: Therapeutic treatment of NSG mice bearing #03008 hT-ALL PDX tumors from 12 days post-transplant after detection of circulating human blasts, with PBS (n=4), naïve-hTNFα (n=6) or IEOmAB1-hTNFα (n=6) every 2 days intravenously; d Flow cytometrically determined percentage of human CD45-positive cells in the peripheral blood mononuclear cell fraction 38 days post transplant; e Kaplan-Meier survival curve analysis of the same mice, receiving 12 intravenous injections of the indicated proteins; f, g & h in vitro binding-dependent hT-ALL cell killing for f CEM hT-ALL cell line and g #03008 hT-ALL PDX, co-incubating cells with increasing equimolar amounts of the indicated proteins; h CEM cells incubated with intact hIgG-IEOmAB2-hTNFα immune-cytokine, or hIgG-IEOmAB2 protein+recombinant hTNFα, hIgG-IEOmAB2 protein alone or recombinant hTNFα alone. Viability measured by automated cell imaging of Trypan blue positivity of cells 4 days post co-incubation with the indicated proteins. Each symbol in a, b & d represents an individual mouse, with horizontal lines indicating mean values with error bars displaying +/−s.d. and significance calculated by two-tailed Mann-Whitney tests. Significance of Kaplan Meier in c & e judged by two-tailed log-rank Mantel-Cox tests. Trend lines plotted in f, g & h represent mean values with error bars displaying +/−s.d. derived from duplicate data points. X's along x-axis indicate injection schedule FIG. 4 T-ALL reactive immuno-cytokine proteins achieve therapeutically relevant delay in human melanoma PDX growth a-d. Daily intratumoral injection of indicated immune-cytokine proteins at equimolar concentration or equivolumetric quantities of PBS into NSG mice bearing subcutaneous ≈30 $mm^2$ MM27 PDX tumors. a & c. tumor area as measured by calipers daily normalized versus area at time of first injection, trend lines represent mean of treated group with error bars indicating +/−s.d. (a n=6 mice/group, c n=5mice/group), p-values calculated by two-tailed Mann-Whitney tests, **p<0.01. b & d. Kaplan-Meier survival curve analysis, mice were sacrificed once gross tumor area exceeded 120 mm2, significance calculated by two-tailed log-rank Mantel-Cox tests. e & f Thrice weekly intravenous injection of indicated equimolar immune-cytokine proteins 10 days post-transplant of MM27 PDX cells, when tumors were palpable. e tumor area as measured by calipers daily, trend lines represent mean of treated group with error bars indicating +/−s.d. (IEOmAB1-hTNFα and naïve-hTNFα n=6 mice/group, PBS n=5mice/group). f Kaplan-Meier survival curve analysis, mice were sacrificed once gross tumor area exceeded 120 mm2, significance calculated by two-tailed log-rank Mantel-Cox tests. g & h in vitro binding-dependent hT-ALL cell killing for g A375 human melanoma cell line and g MM27 human melanoma PDX, co-incubating cells with increasing equimolar amounts of the indicated proteins; Viability measured by automated cell imaging of Trypan blue positivity of cells 4 days post co-incubation with the indicated proteins. Trend lines plotted in g & h represent mean values with error bars displaying +/−s.d. derived from duplicate data points. X's along x-axis indicate injection schedule.

FIG. 5. Immuno-cytokine proteins delay human melanoma xenograft growth by inducing an inflammatory intratumoral microenvironment a & b Representative tissue immunofluorescence images of MM27 tumors injected intratumorally with a single, equimolar bolus of the indicated immune-cytokine protein, or PBS alone. Mice were sacrificed and tumors dissected 48 hours post-injection. Images were merged and false colored using ImageJ software (Blue=DAPI, green=anti human TNFα mAb-FITC, red=anti mouse CD11b-AF647) (a=60×-oil-immersion, b=40× objective). c. Flow cytometric analysis of digested tumor cell homogenates treated as indicated for parts a & b and staining myeloid cell for CD11b. Each symbol in c represents an individual mouse, with horizontal lines indicating mean values with error bars displaying +/−s.d. and significance calculated by two-tailed Mann-Whitney tests. d. QPCR of cDNAs derived from analysis of unfractionated tumor cell homogenates using 1 mouse per group treated as indicated and sacrificed after 48 hours. ΔΔCt values were calculated for each mouse specific primer pair amplified in triplicate and normalized against sample CT-values obtained using GAPDH-specific primers and then expressed relative to the ΔCt values for the PBS-injected tumor sample. Error bars represent +/−s.d. and significance was calculated using paired student T-tests.

Figure 6:
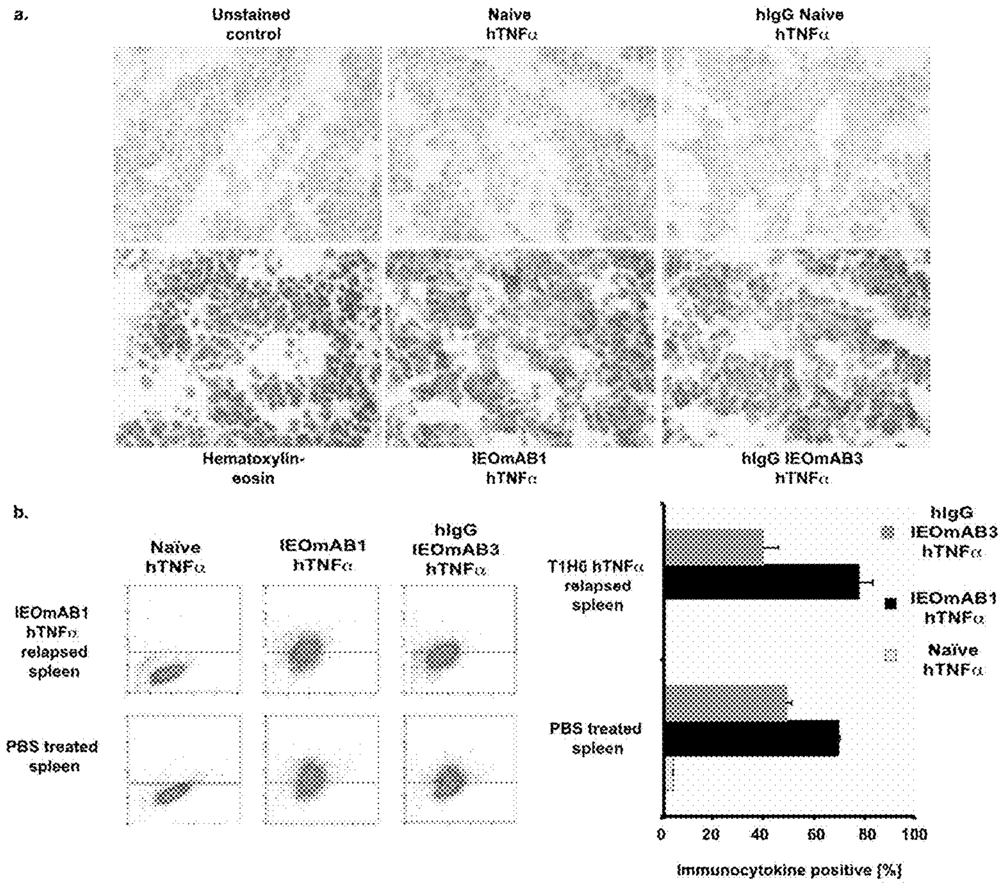

FIG. 6 IEOmAB1-hTNFα treated hT-ALL PDX does not counter-select targeted antigen during the course of therapy a. Immunohistochemical analyses of #03008 infiltrated NSG spleen from a mouse that had been treated intravenously with IEOmAB1-hTNFα immune-cytokine for 30 days (thrice weekly). The mouse was sacrificed 45 days post-therapy cessation for morbidity and 5-micron sections of the OCT-embedded spleen was stained with Hematoxylin/Eosin with or without the indicated Immuno-cytokine protein as detection antibody. Images are representative of at least 5 separate sections per primary antibody. b. Flow cytometric examination of spleen-resident cells harvested from mice relapsed post IEOmAB1-hTNFα therapy-cessation or from mice treated with PBS alone. Live cells were incubated with the indicated proteins and percent positivity was acquired. Left panels representative scatter plots, right panel mean of three flow cytometry reactions per sample, error bars displaying+/−s.d.

Figure 7:
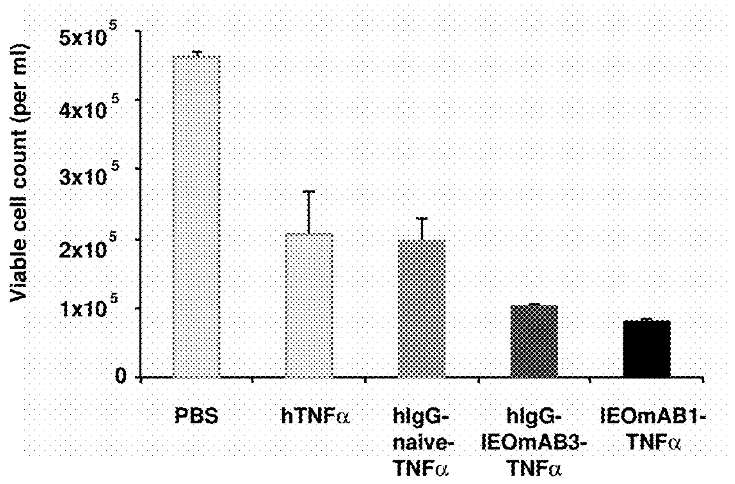

FIG. 7 TNFα-conjugated to scFv candidates is functionally cytotoxic Viability cell count of CEM hT-ALL cells co-incubated continuously for 4 days in culture with 190 nM of the indicated proteins. Viability calculated as trypan blue excluding cells as visualized by automated cell counting, with error bars indicating s.d. calculated from 3 separate biological replicates.

Figure 8:
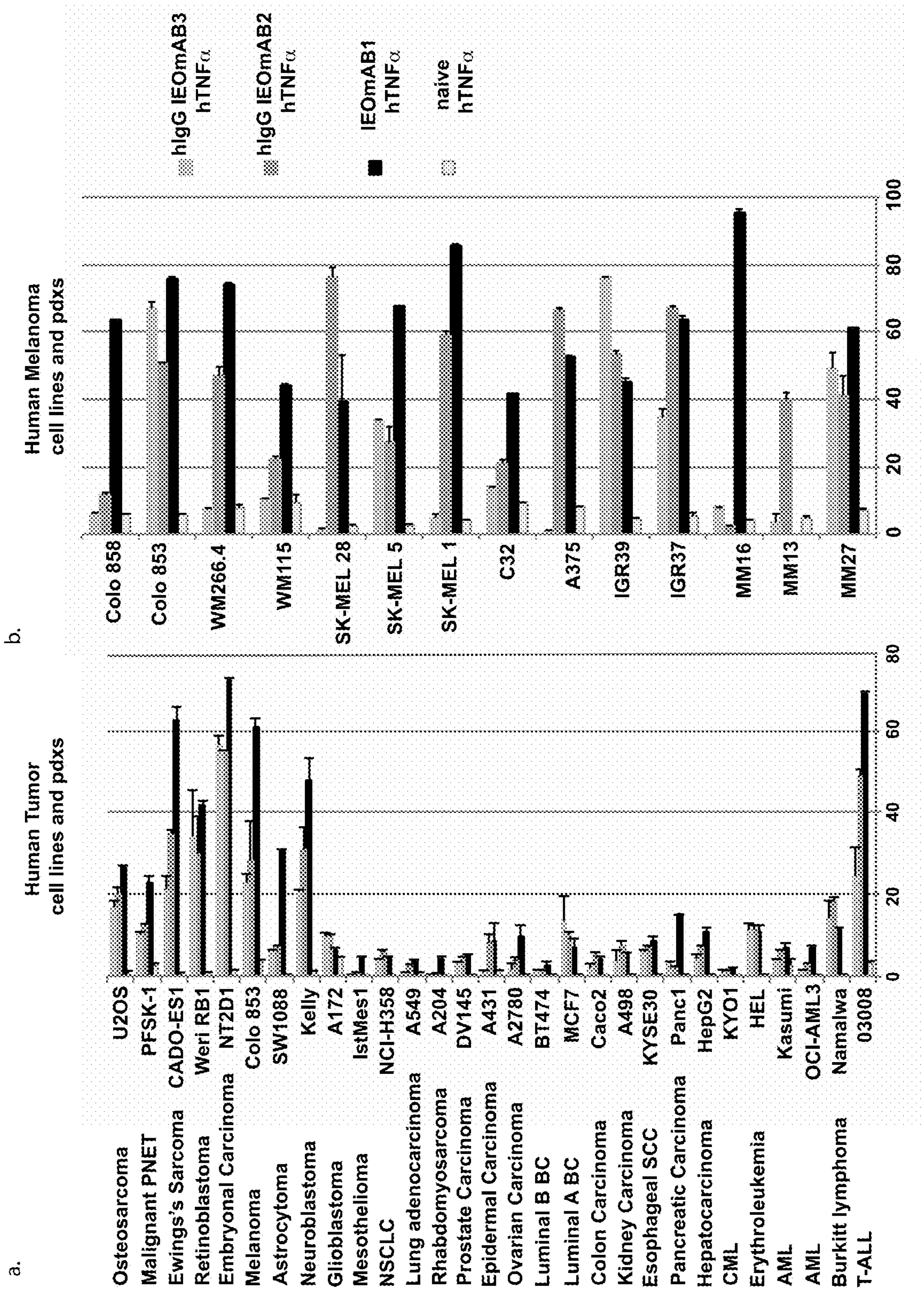

FIG. 8 hT-ALL binding immune-cytokine proteins cross-react with neuro-ectoderm derived tumors and label human melanoma cells a. Flow Cytometric analyses of 29 human tumor cell lines representing diverse neoplasia and tissue origin. b. Flow cytometric analysis of hT-ALL immuno-cytokine binding to 14 human melanoma cell line and PDX (MM27, MM13, MM14) cells. Data shown is the mean value obtained for two independent flow cytometry labeling and error bars display the +/−s.d.

Figure 9:
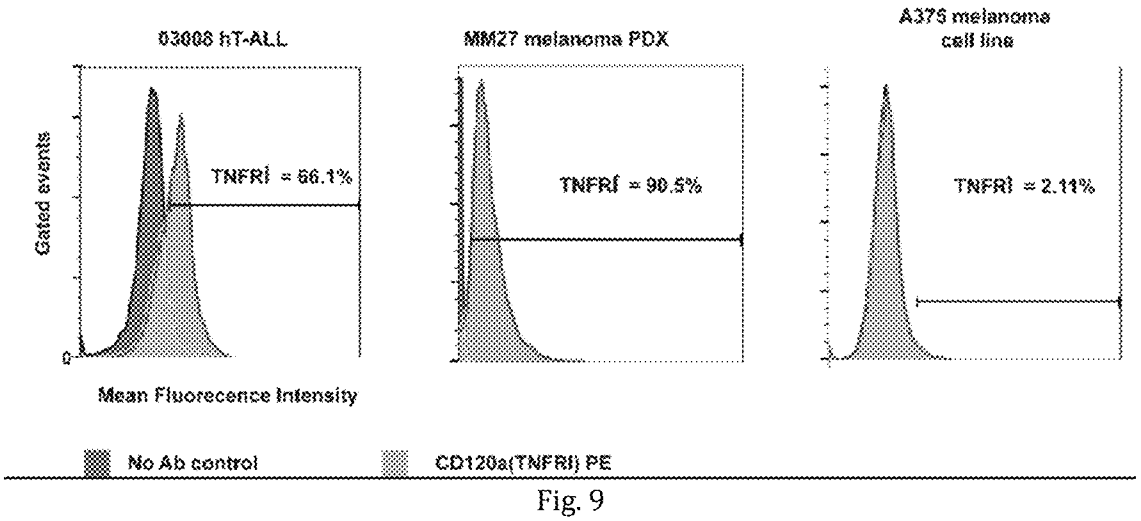

FIG. 9 Human melanomas are TNF-resistant regardless of their TNFRI Positivity Flow Cytometric acquisition of hT-ALL (03008) or human melanoma cells (MM27 PDX or A375 cell line) labeled with anti mouse TNFRI (CD120a)-PE antibody. Histogram plot displays signal for unstained cells (Red) and TNER1 antibody (Blue).

Figure 10:
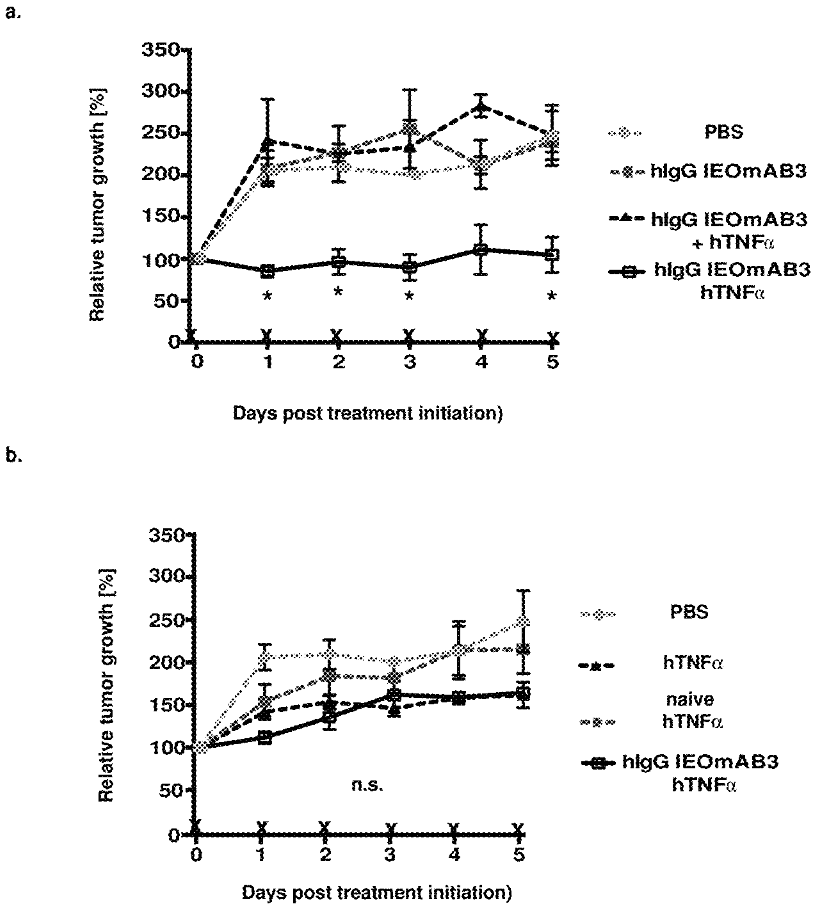
Figure 11:
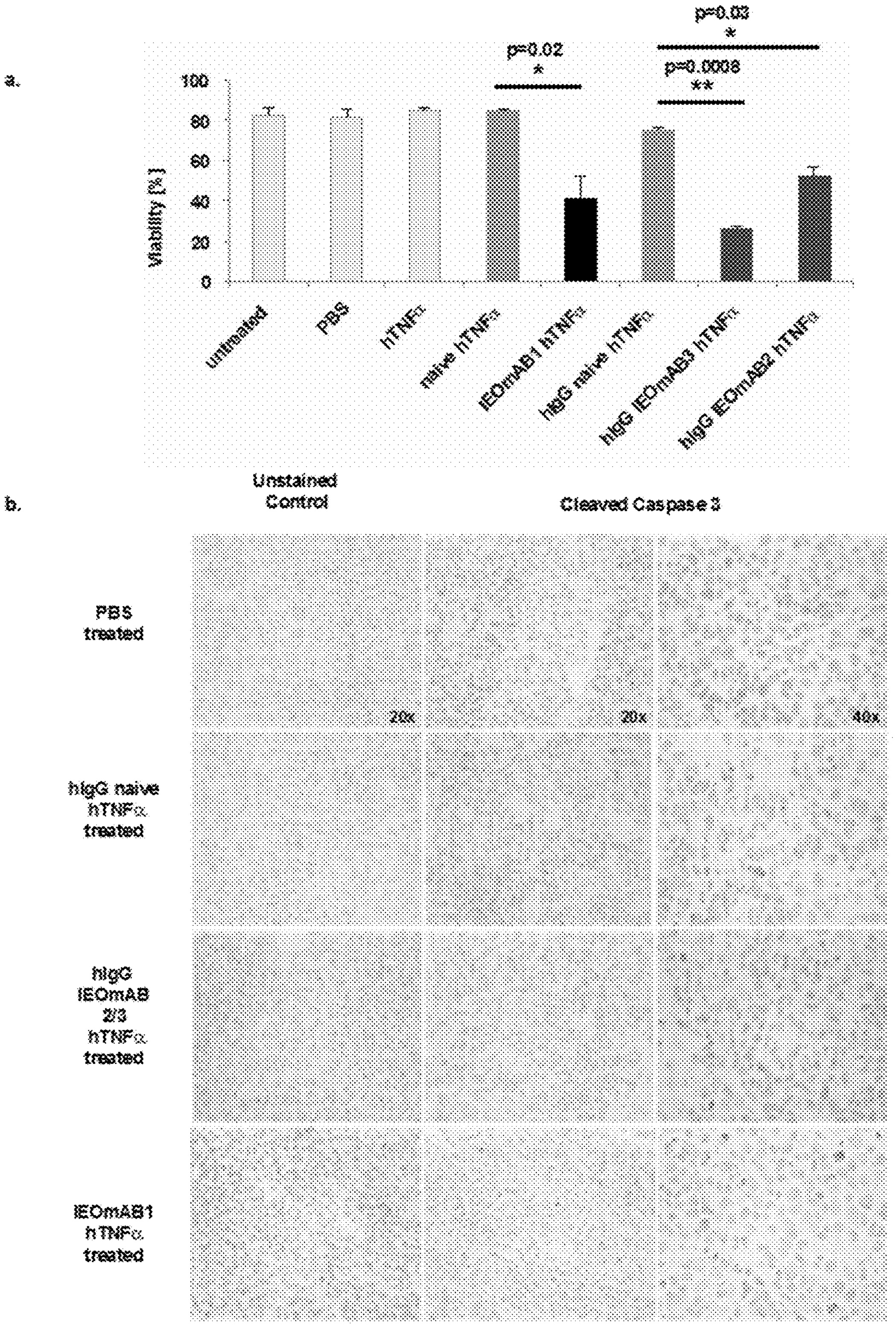

FIG. 10 Anti-tumor effects of immune-cytokine proteins is dependent upon cell binding of intact fusion protein a. Daily intratumoral injection of indicated immune-cytokine proteins at equimolar concentration or equivolumetric quantities of PBS into NSG mice bearing subcutaneous ≈30 mm$^2$ MM27 PDX tumors. Tumors were injected with intact immuno-cytokine (hIgG-IEOmAB3-hTNFα), unfused immuno-cytokine (hIgG-IEOmAB3+hTNFα), antibody alone (hIgG-IEOmAB3) or PBS alone. b. Daily intratumoral injection of indicated immune-cytokine proteins at equimolar concentration or equivolumetric quantities of PBS into NSG mice bearing subcutaneous ≈30 mm$^2$ MM13 PDX tumors, to which the indicated immune-cytokine proteins do not bind. Tumor area was measured by calipers daily and normalized versus area at time of first injection, trend lines represent mean of treated group with error bars indicating +/−s.d. (a n=5 mice/group, c n=4 mice/group), p-values calculated by two-tailed Mann-Whitney tests, *p<0.05 . . . X's along x-axis indicate injection schedule FIG. 11 Intratumoral administration of immune-cytokine proteins induced apoptosis-independent cell death. MM27 tumors injected intratumorally with a single, equimolar bolus of the indicated immune-cytokine protein, or PBS alone. Mice were sacrificed and tumors dissected 48 hours post-injection. a. Cell viability of tumor cell suspensions was determined by automated cell imaging as the count of Trypan blue-excluding cells. All counts were determined in triplicate and 3 tumors per condition were examined. Error bars indicate s.d. of the 6 counted data points, significance determined by 2-tailed student's T-test. b. Immunohistochemical staining of the same MM27-tumors 48 hrs. post-injection, staining for apoptosis via cleaved-Caspase 3 signal. 3 images per tumor were examined in a blinded manner, and representative images are shown.

Figure 12:
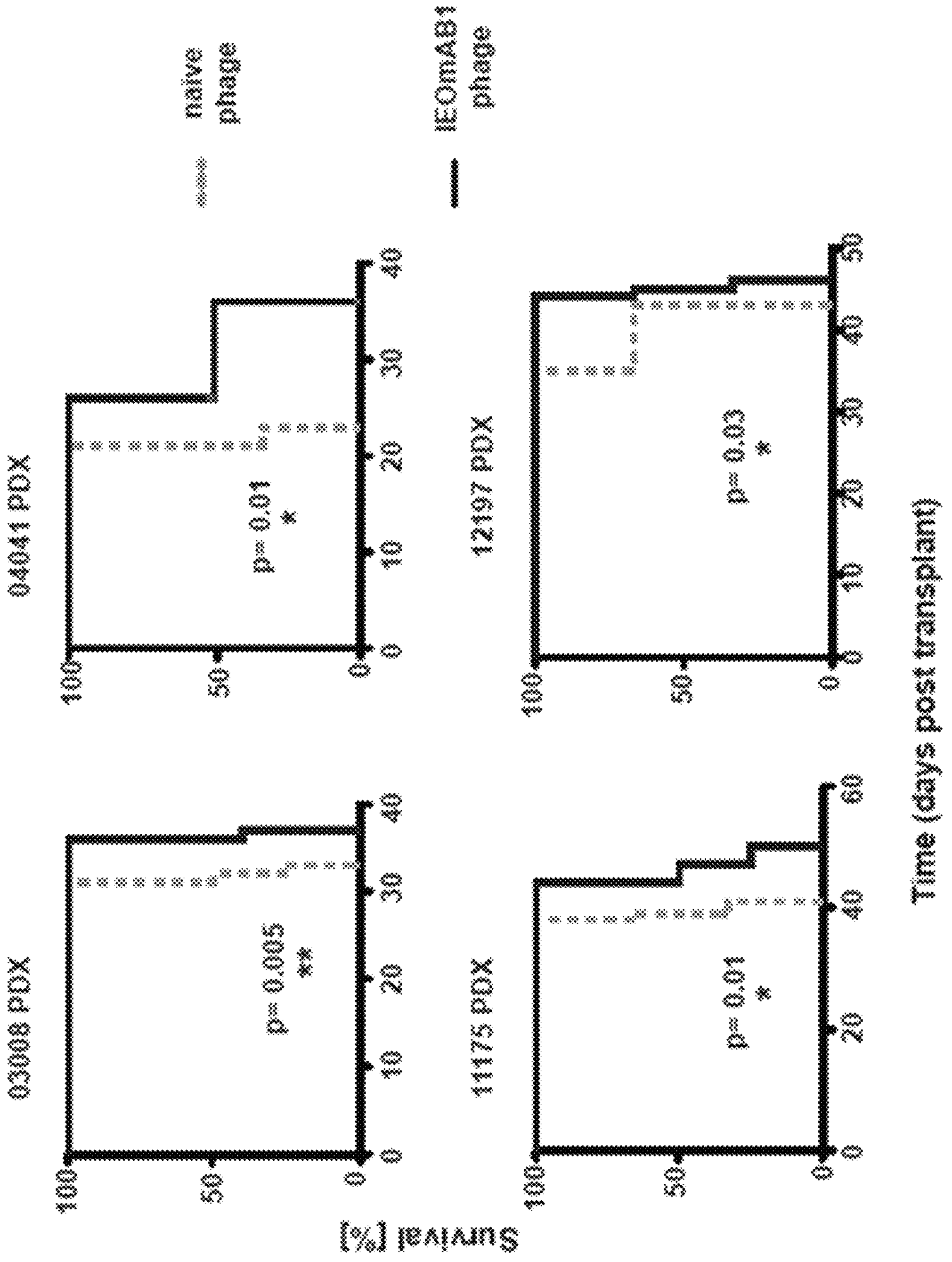

FIG. 12 In vivo efficacy of phage treatment versus hT-ALL PDXs. NSG mice xenografted with hT-ALL PDX specimens deriving from pre-treatment juvenile specimens (04041, 11175) and post-relapse specimens (03008, 12197) were treated with the indicated phage clones starting from 2 days post-transplant. Mice (n=4 per group/tumor) received 1011 of the indicated phage preparation intravenously 3 times per week for up to 3 weeks and time-to-sacrifice was determined. Significance of Kaplan Meier survival curves was calculated by two-tailed log-rank Mantel-Cox tests.

Figure 13:
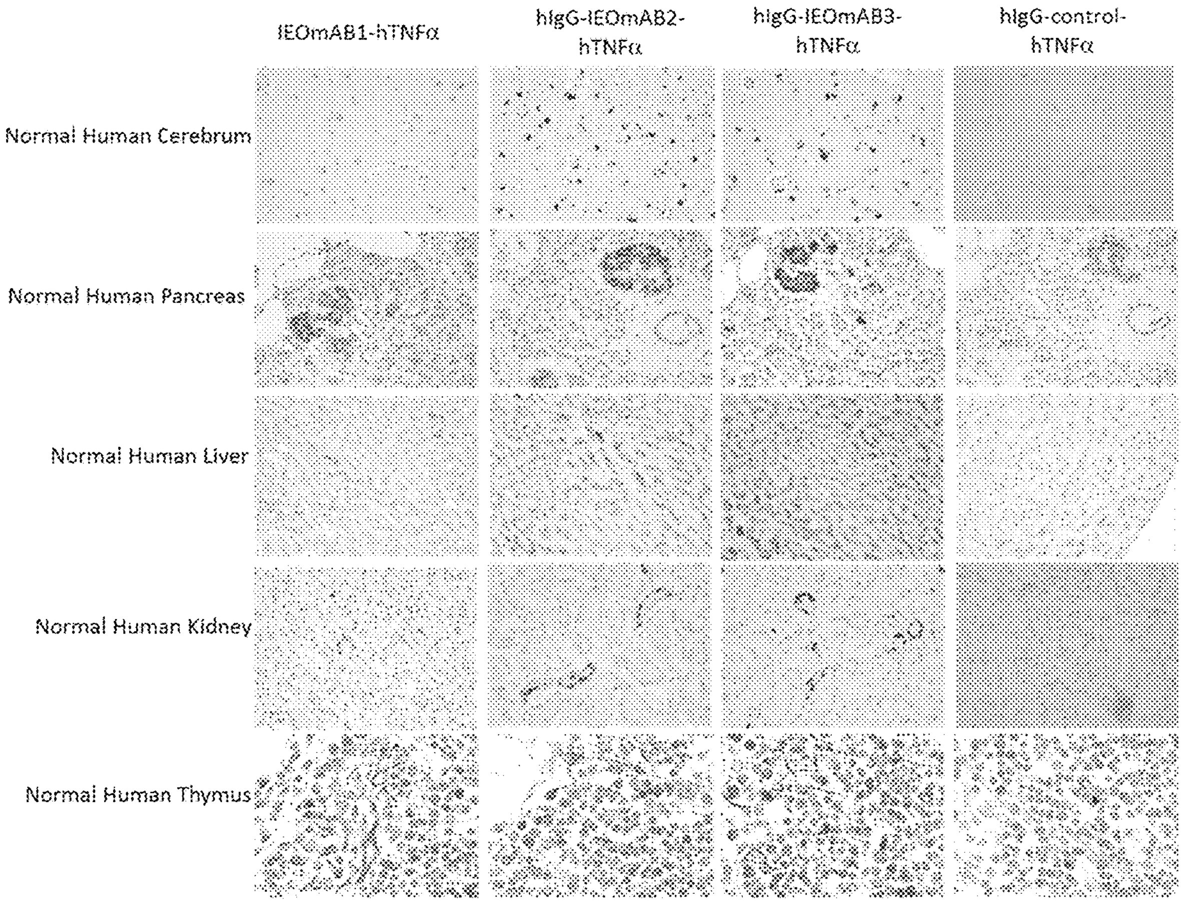

FIG. 13. Immunohistochemical validation of immunocytokine binding to healthy human tissues.

Five tissue slides containing a sequentially-sliced FDA approved paraffin-embedded healthy human tissue array (AMSBIO, 90 specimens, 3 patients per tissue) were used to detect tissue cross-reactivity for: IEOmAB1-hTNFα, hIgG-IEOmAB2-hTNFα, hIgG-IEOmAB3-hTNFα, hIgG-control-TNFα and antibody-free controls. Immunocytokine binding was revealed using a biotinylated anti-human TNFalpha antibody and slides were counterstained with Mayer's hematoxylin. Slides were scanned upon an automated immunohistochemical scanner and individual tissue specimens were captured by bright-field microscopy. Representative images from the same patient sample in each tissue are shown at 20× magnification, bright-field microscopy.

EXAMPLES

Materials and Methods

In Vivo Biopanning Procedure

The M13 bacteriophage based ETH2-Gold scFv display library[20] was used for all experiments. $10^{11}$ Ab-phage colony-forming units (CFUs) were injected into healthy 6-8-week-old female C57-CD45.1 animals [Envigo]. Ten minutes post-injection, mice were sacrificed, heart blood was harvested, and cell-bound phage was removed by centrifugation. Unbound phage ($1^{st}$ round in vivo depleted) was amplified via infection of mid-log phase TG1 *E. coli* and purified as previously described[40 41]. The depleted phage library produced was co-incubated for 45 minutes ex vivo at 4° C. with $4\times10^6$ CD45.1+WT murine PBMCs to deplete the library of phage binding to house-keeping proteins. Unbound phage were diluted into PBS and infused intravenously into C57-CD45.1 splenomegalic mice (Charles River) previously injected with CD45.2+ syngeneic murine T-ALL. Ten minutes post-injection, animals were sacrificed and mT-ALL infiltrated spleens harvested, smashed and mononuclear cells (MNCs) were purified on Histopaque gradient. Four million counted splenic MNCs were lysed and eluted phage was then used to infect mid-log phase TG1 ($2^{nd}$ round mT-ALL blast binding phage). A third and final round of in vivo biopanning was performed using $10^{11}$ CFUs from the $2^{nd}$ round phage with pre-depletion upon CD45.2+ PBMCs. All phage preparation-CFUs were determined in triplicate.

Competitive Flow Cytometry Binding Assay to Select scFv Candidates

Following phage infection, single TG1-scFV-myc-phage clones were picked and grown to mid-log phase in selective 2×TY media and scFv production was induced over night in the presence of IPTG. The resulting monoclonal cultures were pelleted and then subjected to TES lysis as previously described[41] to isolate periplasmic proteins. ScFv-MYC protein expression was evaluated via Western Blot using an anti-myc tag monoclonal antibody (Abcam). Periplasm from scFv-MYC expressing clones were then incubated overnight with 1 million fixed cells containing 50% murine T-ALL blasts (CD45.2+) and 50% normal MNCs from mouse spleen and bone marrow (CD45.1+). Cell pellets were washed and probed with anti CD45.1-FITC monoclonal antibody (BD Pharmingen) and anti myc-biotin antibody (Miltenyi) and re-probed with an anti-biotin-APC labeled secondary antibody (Miltenyi), before acquisition by flow cytometry.

Antibodies were judged to be candidates if they bound more than 20% of murine T-ALL blasts (FITC+) and exhibited at least 2.5-fold stronger signal on tumor than normal cells. Initial Candidates were confirmed by repeated flow cytometry binding to mT-ALL blasts using different periplasmic preparations from the same clone. Out of 800-screened clones, 83 met the criteria, of which the 25 best performing, non-redundant clones were selected. The TOP25 candidates were then produced in large scale and, secreted scFv protein was purified from ultra-filtrated supernatant by running it by AKTA over a 1 ml packed Protein A SEPHAROSE™ resin (GE Healthcare). Bound scFv proteins were washed with buffer containing 0.1% Triton-X114 to remove endotoxin. Proteins were eluted on column with 0.1M TEA and eluted into 1M Tris pH 7.4. Protein concentration and buffer exchange were performed on VivaSpin 2 columns, 3000 MWCO to 99.5% purity. The 10 best producing scFv-clones were then used for further tests.

In Vivo Phage Localization

Phage intended for in vivo use was precipitated as previously described[40], and were certified to be bacteria-free by limited dilution plating. C57/Bl-6J mice bearing full-blown syngeneic mT-ALL tumors with palpable splenomegaly, or their tumor-free littermates were injected with $1\times10^{11}$ CFUs of the indicated scFv-phage clones, a non-cell binding naïve scFv-phage, or PBS as indicated. Two days post-injection, mice were sacrificed and spleens were collected. Spleen cells (10000) were added to 1 ml of mid-log phase TG1 then subjected to limiting dilution plating. All titrations were performed in triplicate and the resulting CFUs were taken as a proxy of in vivo phage biolocalization.

Counted cells from single cell spleen-suspensions were similarly examined by flow cytometric analysis to count the number of T-ALL blasts ($hCD45^+$ or $CD4^+CD8^+$ cells).

In Vivo Phage Treatments

For in vivo phage therapy in a low-grade disease setting, 6-8 week old female NOD-scid-IL2rgamma null mice (The Jackson Laboratory) were injected with 1 million 03008 hT-ALL PDX blasts[22] that had been previously co-incubated at with either tumor binding (IEOmAB1) or non-binding (Naïve) phage. Forty-eight hours later, intravenous treatment every 3 days with $10^{11}$ of the same phage was commenced. Tumor progression was monitored weekly by hematological analysis (Becton Coulter AcT 5Diff Hematological Analyzer) and flow cytometry. In vivo experimentation using phage was done in accordance with the Italian Ministry Of Health approved animal project #29/2013.

Cell Culture

All cell lines were maintained in accordance with the indications of the American Type Cell Culture Collection or DSMZ. Cell line identity has been verified by an in-house tissue culture service.

Eukaryotic Antibody and Immunocytokine Cloning and Production

Human IgG-scFvs were generated by subcloning single scFv sequences into pINFUSE hIgG1-Fc2 vector (In VivoGen) via Gibson assembly[42]. Due to biochemical incompatibility between IEOmAB1 scFv and the hIgG1-Fc domain, IEOmAB1 was cloned into the same vector from which the hIgG1-Fc2 sequence had been excised by restriction digestion.

Immuno-cytokine (IC) constructs were generated by fusing the 17 kD secreted form of human TNFα and a $(S_4G)_3$ [SSSSGSSSSGSSSSG] (SEQ ID NO:28) flexible polylinker to the 3' end of the hIgG1-Fc2-scFv clones described above. Similar methods were used to directly fuse scFv clones with the human TNFα $(S_4G)_3$ (SEQ ID NO:28) polylinker.

Human IgG- and- and IC vectors were transiently transfected into HEK-293T cells by polyethyleneimine method[43], and grown in serum free medium for 5 days. Medium containing the secreted proteins were passed through 0.22 μm filters, supplemented with protease inhibitors and affinity purified in batch overnight. ScFv-TNFα via Protein A SEPHAROSE™ while scFv-hIgG1, and scFv-hIgG-TNFα via Protein G SEPHAROSE™ (GE Healthsciences). Proteins were eluted as described above and concentrated upon 30,000 kD MWCO Vivaspin 20 centrifugal concentrators. Purified proteins were buffer exchanged into 50% glycerol supplemented with 10 mM Tris pH 7.0 and 150 mM NaCl for long term storage. Proteins were run on 12.5% SDS-PAGE and the presence of fusion proteins was verified by Western blot (rabbit anti-human TNFα [Abcam] or donkey anti human $Fab^2$-HRP [Jackson Immunological Research]). Protein concentration and purity was determined via Western blot or Commassie against a relevant standard curve.

In Vitro Toxicity of ICs

In vitro susceptibility to free human TNFα was established in a continuous co-culture system. or A375 human melanoma, MM27 human melanoma PDX ($5\times10^4$), #03008 human T-ALL PDX cells or CEM human T-ALL cells ($5\times10^6$) or were incubated for 4 days in the presence of IC proteins or human TNFα protein (Peprotech) in 2-fold serial dilutions from 190 nM to 0.005 nM concentration. Cells were trypsinized, counted, their viability determined by Trypan blue exclusion via Automated Cell Counters (Bio-Rad).

To determine binding-dependency of immune-cytokine proteins, #03008 or CEM cells ($5\times10^6$) were co-incubated on ice for 30 minutes with equimolar concentrations of hIgG-scFv conjugates, IC and cytokine proteins. Cells were then pelleted by centrifugation, washed twice with ice-cold PBS and then resuspended in growth medium supplemented with amphotericin B (2.5 μg/ml) and gentamicin (50 μg/ml). Cell growth and viability was determined as described above.

In Vivo Treatment with Immuno-Cytokines

For intravenous treatments of T lymphoblastic leukemia, IC proteins were injected at equimolar therapeutic doses (=0.25 mg/kg/mouse for immunocytokines). IC protein was diluted such that each mouse received a precisely similar amount of IC protein and storage buffer (see above) diluted into 300 μl of PBS/mouse/injection. Mice received injections 2-3 times per week via tail vein and were then monitored daily for adverse reactions. A small amount of peripheral blood was periodically drawn to monitor disease progression via hematological analyzer and flow cytometry. All mice received at least 10 total injections and were then monitored daily, until exhibiting signs of morbidity, when they were sacrificed.

For treatments of human melanoma xenografts, age and sex-matched Avertin-anesthetized NSG mice were injected intradermically with 250,000 MM27 or MM6 cells, as previously described[25]. For intratumoral injections, fully acclaimed tumors (≅30 $mm^2$) were injected with 50 μl per day of PBS containing equimolar concentrations of IC proteins (150-250 ng). Injection points were rotated daily and tumor progression assessed by digital calipers daily prior to injection. All mice received at least 5 intratumoral injections and animals were sacrificed when their tumors exceeded 120 $mm^2$, in accordance with institutional and international guidelines. For intravenous treatments, mice were xenografted with 250,000 MM26 cells and when animals had a palpable hyperkeratosis in the injection zone (7-10 days post-transplant), mice were treated as above with thrice weekly injections of 0.25 mg/kg/mouse. Animals that did not yield a measureable tumor within 14 days were excluded from the analysis. All experiments were performed at least in duplicate, and representative data is shown.

Immune Infiltration Analysis of Melanoma Xenografts

Age-matched male NSG animals bearing ≅50 $mm^2$ MM27 melanoma xenografts were injected with a single equimolar dose of IC diluted in 100 μl of PBS (150-250 ng). Forty-eight hours post-injection animals were sacrificed and tumors excised. A third of the tumor mass was fixed in 4% PFA overnight before embedding in OCT compound (Tissue Tek) while the remainder was minced and digested in the presence of collagenase A (0.5 mg/ml) [Roche][25]. Tumor homogenates were then successively filtered through cell strainers and washed twice in PBS+1 mM EDTA pelleted and red blood cells were lysed with ACK buffer. The resulting cell suspension was counted and fixed with 1% PFA for 15 minutes at 4° C.

Immune infiltrates were quantified by cytometry using either the FACSAria or FACSCanto machines (Becton Dickinson). Total immune infiltrate was assayed by CD11b-APC (BD Pharmingen) antibody. All experiments involving in vivo administration of immunocytokine proteins were done in accordance with the project #968/2017, approved by the Italian Ministry of Health.

Immunohistochemistry and Tissue Immunofluorescence

IC binding to tumor tissue was determined against whole organ tissue fixed overnight at 4° C. in 4% paraformaldehyde and exchanged overnight in 30% sucrose. #03008 hT-ALL infiltrated mouse spleen pre- or post-therapy were embedded in OCT medium and cut into 5-micron slices on frosted microscope slides. Slices were fixed with 30% ethanol and endogenous peroxidases were neutralized by 10-minute incubation with 0.3% hydrogen peroxide. Slides were probed with 1 ng of the indicated immunocytokine protein in 100 μl PBS+2% BSA overnight in a 4° C. humidified chamber. Sections were washed 3 times and probed with a biotinylated rabbit anti human TNFα antibody (R&D Biosystem) for 4 hours at room temperature. Sections were again washed extensively and developed for 1 hr. using the ABC kit (Vector Labs) according to the manufacturers protocol. Antibody binding was revealed by DAB staining and sections were counter-stained by hematoxylin-eosin.

Detection of apoptotic cells within immunocytokine treated melanoma xenografts was performed as indicated above. Rabbit anti cleaved caspase 3 antibody (Cell Signaling Technologies) was used to visualize activation of apoptosis, followed by goat anti rabbit goat-HRP and visualized by DAB positivity. At least 5 distant slices were examined per tumor. All images were acquired on a Nikon color Digital Sight DS-5mc light microscope.

OCT-frozen sections (5 μm, micrometer) were fixed in 4% paraformaldehyde and pre-blocked with PBS supplemented with 1% BSA and normal donkey serum. Primary antibodies were incubated overnight in a 4 degree humidified chamber. Sections were probed with human anti-TNFα (Miltenyi), rabbit anti-mouse cd11b (BD Biosciences), phalloidin FITC and DAPI. Sections were washed and probed with donkey anti rabbit Cy3. Images were acquired upon an Olympus BX61 upright fluorescence microscope using 40× or 60× oil-immersion objectives. Images were analyzed using ImageJ software.

Five tissue slides containing a sequentially sliced FDA approved paraffin-embedded healthy human tissue array (AMSBIO, 90 specimens, 3 patients per tissue) were used to detect full human immunocytokine proteins (IEOmAB1-hTNFα, hIgG-IEOmAB2-hTNFα, hIgG-IEOmAB3-hTNFα) with respective controls hIgG-control-TNFα and antibody-free) For IHC analysis paraffin was removed with xylene and the sections were rehydrated in graded alcohol. Antigen retrieval was carried out using preheated target retrieval solution for 45 minutes. Tissue sections were blocked with FBS serum in PBS for 60 min and incubated overnight with primary immunocytokine protein fused to human IgG1 and human TNFα. The antibody binding was detected with an anti-human TNFα-biotinylated (R&D System) amplified with ABC Kit (Vector lab) followed by a diaminobenzidine chromogen reaction (Peroxidase substrate kit, DAB, SK-4100; Vector Lab). All sections were counterstained with Mayer's hematoxylin and visualized using a bright-field microscope and imaged upon an automated immunohistochemistry scanner. Tissue binding by immunocytokine proteins was graded by an independent pathologist without prior knowledge of the antibody identities or presumed tissue interaction profiles. Stainings were judged as either negative for tissue binding, aspecific/background binding or positive for specific binding.

QPCR Analyses

Snap frozen cell pellets obtained from unfractionated IC-treated MM27 tumors were thawed and mRNAs were extracted using RNeasy columns (Qiagen) and converted to cDNAs using reverse transcriptase following standard protocols. cDNAs were amplified in triplicate by SYBR green (Life Technologies) incorporation method using mouse gene specific primers upon the 7500 Fast Real Time QPCR (Applied Biosystems). mRNA quantifications from $-\Delta\Delta Ct$ values and their significance were calculated with standard methods and data was obtained from at least 2 different QPCR runs. CT values were normalized versus GAPDH expression levels, and relative fold change values were calculated against the negative control (PBS-injected) MM27 tumor sample.

Statistical Analyses

Kaplan-Meier survival curve analyses and tumor growth curve analyses were performed with the GraphPad Prism software package. Statistical significance of survival outcome was judged by the two-tailed log-rank non-parametric test[44], while tumor growth curves were judged by the two-tailed Mann-Whitney test[45].

Results

In Vivo Phage Panning Against Growing Mouse T-ALL Allows Isolation of scFvs with In Vivo Tumor-Binding and Anti-Leukemic Activities.

To identify antibodies against human T-ALLs (hT-ALL), inventors designed a streamlined workflow (FIG. 1) for the panning of Myc-tagged single-chain variable fragments (Myc-scFv) (ETH2-Gold phage-library from Philogen[20]). Critical steps of our workflow were: i) pre-depletion of phage-antibodies binding to normal cells, to minimize the likelihood of isolating antibodies directed towards antigens present on healthy tissues; ii) screening in vivo upon growing tumors to enrich for antibodies with in vivo binding activity; iii) the use of a syngeneic murine T-ALL disease model (mT-ALL), to operate in a more physiological, immune-competent context; iv) the prioritization of selected antibodies based upon preferential ex vivo binding to mT-ALL as compared to WT-PBMCs and conservation of binding to human T-ALL cells; v) the funneling of selected antibodies based on their in vivo anti-leukemic activities when injected as phage-antibody particles. It is known, in fact, that phage particles and/or their inherent LPS contamination can function as immunodominant agonists[21]. Finally, inventors analyzed in vivo anti-leukemic activities of those candidate antibodies that showed cross-reactivity with hT-ALLs, using patient derived xenografts (PDXs) from relapsed and chemo-resistant samples.

As a syngeneic model of T-ALL, inventors used a leukemia obtained in C57BL/6 mice following exposure to the mutagen N-ethyl-N-nitrosourea. Blasts express the CD4 and CD8 T-cell antigens, accumulate in the spleen and can be propagated indefinitely in vivo (mT-ALL; not shown). As depicted in FIG. 1, inventors first depleted the ETH2-Gold library of phage binding antigens expressed on normal cells by injecting it intravenously into healthy C57BL/6 mice ($10^{11}$ particles) and recovering unbound phages from the cell-free plasma, which were subsequently amplified in bacteria (in vivo depleted library). To minimize carryover of irrelevant phage clones, in vivo depleted phage were re-depleted ex vivo with fresh WT splenic mononuclear cells before injecting unbound phage into leukemic mice. Murine T-ALL bound phages were recovered from infiltrated spleens, and again amplified in bacteria (mT-ALL enriched library). A second round of in vivo panning was performed using mT-ALL enriched phage as above to further select for tumor-binders. 800 individual Myc-scFv clones were selected from the $2^{nd}$ round enriched library and produced in bacteria to test for binding to mT-ALL or healthy cells by flow cytometry (ex vivo binding). By these analyses, 25 Myc-scFv showed reproducible, preferential ex vivo mT-ALL binding with ≥2.5-fold mT-ALL: healthy-cells binding (3 independent preparations) and/or consistent mean fluorescence values. It means that, as shown e.g. in FIG. 2, candidate antibodies preferably bind at least 20% of tumor cells and, when co-incubated with a mix of 50% mT-ALL blasts and 50% normal mouse blood cells, they preferably bind at least 2.5 fold better to tumor cells either in terms of percent positivity (indicating an antigen predominantly expressed in tumors) or fluorescence signal intensity (indicating an antigen over-expressed by the tumor cells) as judged by flow cytometry. The results preferably have to be consistent with at least 3 separate flow cytometry staining. When tested against normal mouse tissues, the antibodies of the invention do not significantly cross-react with healthy cells under the conditions tested. Therefore, ALL tumor antibodies bind also normal cells to a certain extent. However, their antigen is predominantly or preferentially expressed upon the surface of tumor cells or they bind to healthy tissues that are not essential for survival.

DNA sequence-analyses to eliminate repetitive clones and prioritization of scFvs with the highest production yields reduced numbers of selected clones to 10 non-redundant molecular species (not shown). Cross-reactivity with human T-ALLs for these 10 antibodies produced as Myc-scFv in bacteria or hIgG-scFv fusions in transiently transfected HEK293T cells was assessed by flow cytometry against four hT-ALL cell lines (Jurkat, DND41, T-ALL1 and CEM) and 5 patient derived xenografts (PDXs)[22], respectively. Strikingly, 9 of the 10 best antibodies showed >20% reactivity with at least two independent T-ALL specimens (FIG. 2*a-b*), suggesting high cross-species antigen conservation.

In vivo anti-leukemic activity was evaluated for the nine phage clones (IEOmAB1, N3H1, IEOmAB3, IEOmAB5, T2D3, T2E7, T2G5, T1E9, T2E9). Intact phage-particles were injected into mice with end-stage mT-ALL (Phage-Myc-scFv; $10^{11}$ particles/mouse) and infiltrated spleens were evaluated after 48 hours for weight and blast infiltration (FIG. 1: in vivo anti-leukemia effect). Strikingly, IEOmAB1 and, to a lesser extent, the IEOmAB3 Phage-Myc-scFv showed significant anti-leukemic effects, while the other tested phages did not (FIG. 2*c-d* for representative results of the IEOmAB1, IEOmAB3 and T2D3 phages). Inventors noticed, however, no apparent correlation between ex vivo binding and biological activity, since clones with high binding exerted no anti-leukemic effect (60-70%: T2D3, 30-40%: IEOmAB3, and 20-30%: IEOmAB1). Notably, three clones representative of high, intermediate or low ex vivo binding to mT-ALL (primary murine TALL blasts taken freshly from mouse spleens bearing the tumor) (T2D3>IEOmAB3>IEOmAB1) showed remarkably different in vivo binding properties: IEOmAB1>IEOmAB3, with T2D3 showing low binding (FIG. 2*e*; see legend for methods of in vivo binding analyses), suggesting that in vivo antigen accessibility and anti-leukemic activity are best predicted by in vivo biolocalization. In conclusion, in vivo panning of a phage-antibody library against growing tumors allows selection of phage-antibodies with in vivo tumor-binding and anti-tumor activity.

Fusion of the IEOmAB1 scFv with Human TNFα Mediates Successful Immunotherapy of hT-ALLs.

Inventors then tested the anti-leukemic activity of our best candidate clone (IEOmAB1) against human T-ALL (hT-ALL), using PDXs from relapsed and chemo-resistant samples[22]. Flow cytometry analyses of the reactivity of IEOmAB1-Myc-scFv with 5 hT-ALL PDXs, using anti-Myc antibodies, showed specific binding to all samples, though to a variable extent (FIG. 2*b*). In vivo treatment of hT-ALL PDXs with purified IEOmAB1-Myc-scFv's, however, had no effect on leukemia growth and mouse survival most likely due to its lack of effector function. Since the IEOmAB1-Myc-scFv was active against mT-ALL when injected as phage-particles (FIG. 2*c-d*), inventors tested whether the IEOmAB1 phage-particles were active also against hT-ALLs. Strikingly, treatment of the chemoresistant hT-ALL PDX #03008 with the IEOmAB1-Phage-Myc-ScFv markedly reduced levels of circulating hCD45+ cells (FIG. 2*f*; evaluation at +30 days) and extended survival (FIG. 2*g*), compared to mice treated with naïve phage particles, suggesting that the in vivo anti-leukemic effect of IEOmAB1-Myc-scFv's are unmasked when expressed as phage particles.

Figure 3A:
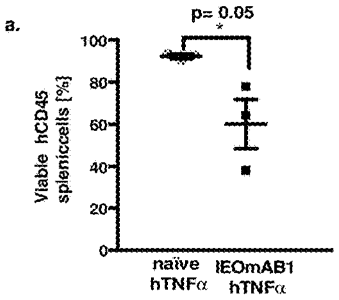
Figure 3B:
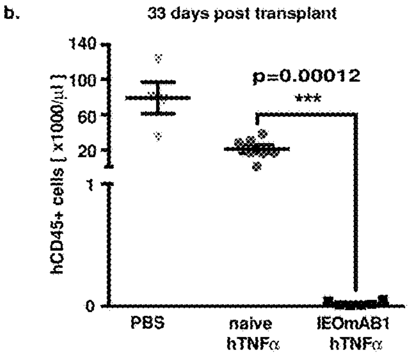
Figure 3C:
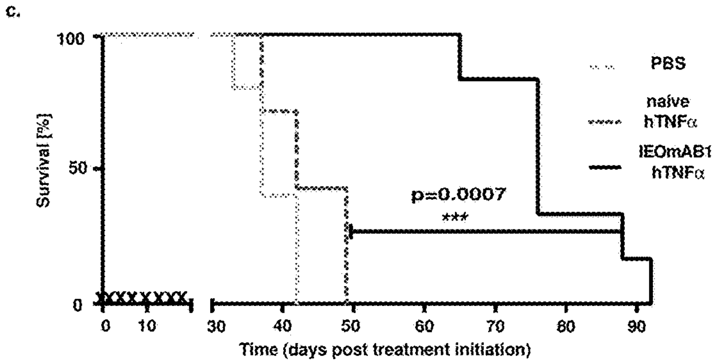
Figure 3D:
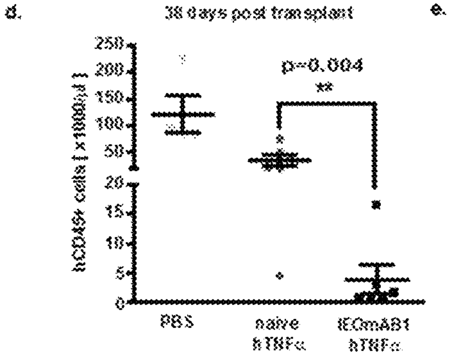
Figure 3E:
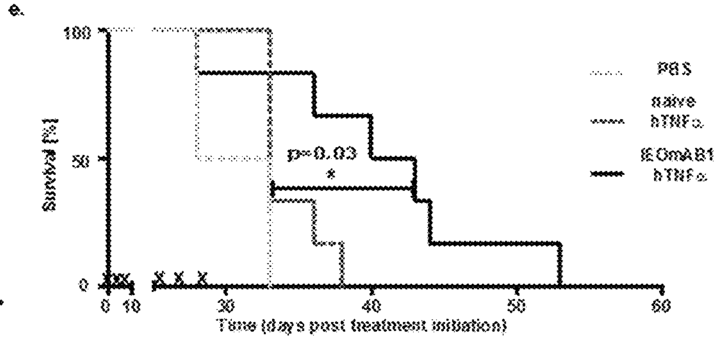
Figure 3F:
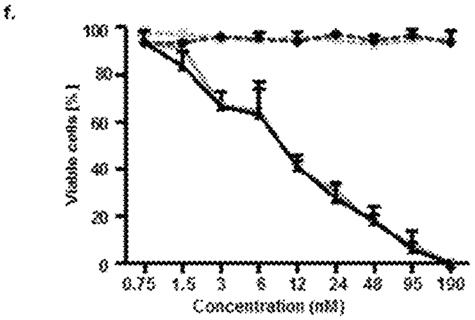
Figure 3G:
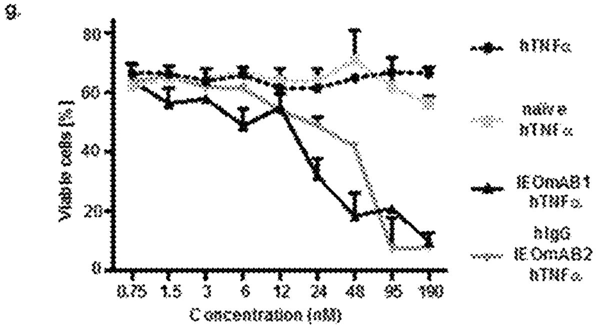
Figure 4:
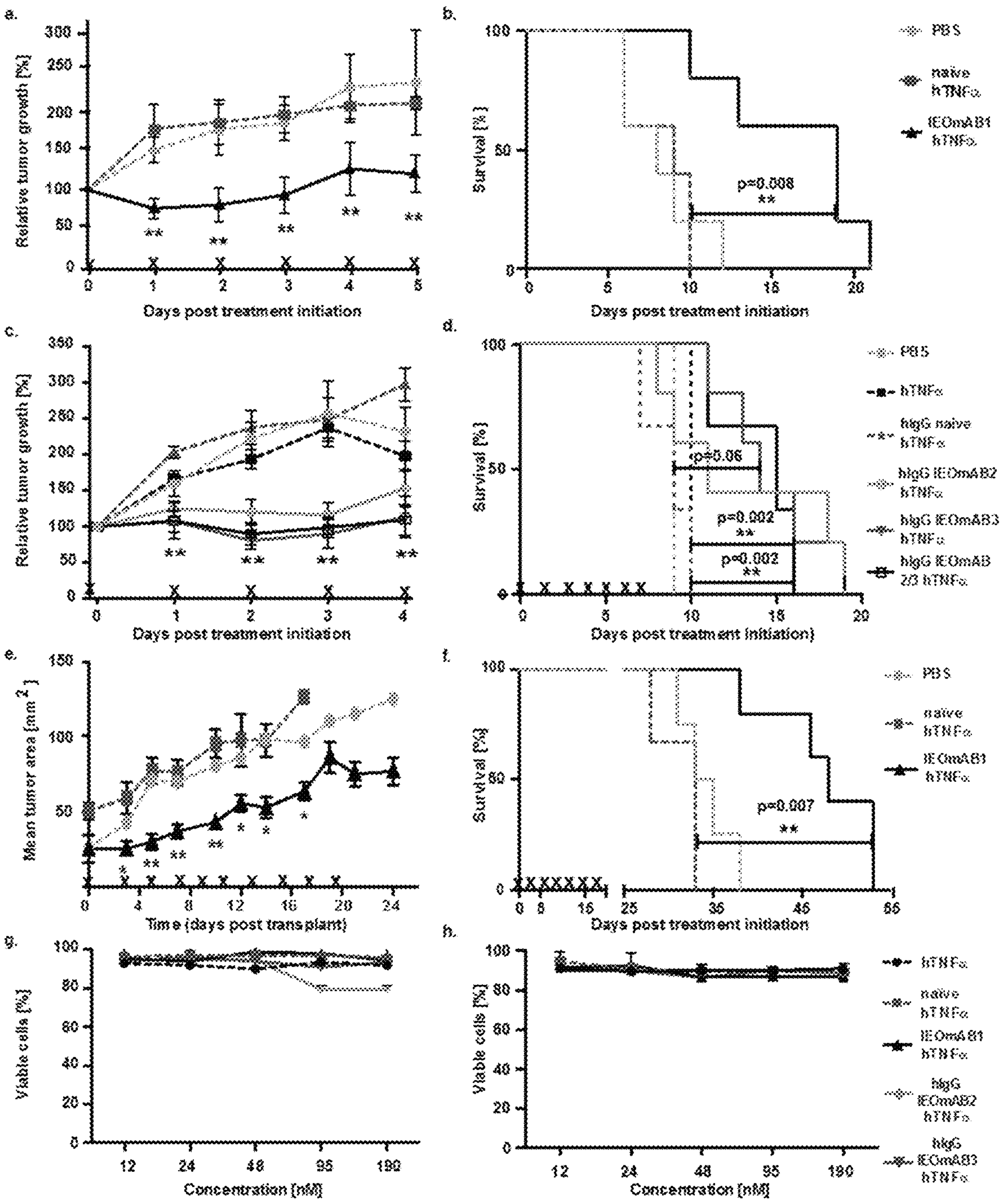

Thus, to mimic the putative inflammatory state created by intact phage particles[21], inventors fused the IEOmAB1-scFv with human TNFα, a major pro-inflammatory cytokine with potent anti-tumoral activity[23], and analyzed the effects of the immune-cytokine on hT-ALL in vivo. One single dose of IEOmAB1-scFv-hTNFα or control-scFv-hTNFα was injected intravenously into end-stage, splenomegalic #03008 PDX bearing mice, which were sacrificed 48 hrs. later. Spleen-infiltrating hT-ALL cells were quantified using human-specific anti-CD45+ antibodies. As shown in FIG. 3*a*, IEOmAB1-scFv-hTNFα significantly decreased numbers of hCD45-positive cells, compared to control-scFv-hTNFα. To investigate whether IEOmAB1-scFv-hTNFα provides a survival benefit, leukemic mice were treated continuously for two weeks starting 48 hours after injection of the #03008 hT-ALL blasts. Tumor growth was monitored by flow cytometry analyses of circulating hT-ALL blasts. One month post-transplant, when the first control mouse died, mice treated with IEOmAB1-scFv-hTNFα showed normal WBC counts with no or minimal blast invasion (<1%), while mice treated with control-scFv-hTNFα or PBS manifested leukemic hyperleukocytosis (FIG. 3*b*). Consistently, mice treated with IEOmAB1-scFv-hTNFα showed a median survival of 78.8 days, as compared to 42.3 and 46.2 days for PBS and control-scFv-hTNFα, respectively (p=0.007; FIG. 3*c*). Notably, in mice with recurrent disease after cessation of IEOmAB1-scFv-hTNFα treatment, the splenic hT-ALL blasts retained binding to the immune-cytokine, as shown by immunohistochemistry (FIG. 6*a*) and flow cytometry (FIG. 6*b*), indicating that the targeted antigen was not counter-selected during treatment. Finally, inventors investigated the efficacy of IEOmAB1-scFv-hTNFα against full-blown hT-ALL, treating #03008 PDXs at 12 days after leukemia injection, when blasts were readily detectable in the peripheral blood (3,000-12,000 $hCD45^+$/ml). Strikingly, by ~40 days post-transplant, IEOmAB1-scFv-hTNFα treated animals showed significantly lower levels of circulating $hCD45^+$-WBCs, compared to mice receiving control-scFv-hTNFα or PBS (p=0.004; FIG. 3*d*), and significantly longer survival time (p=0.03; FIG. 3*e*). Thus, the tumor-specific immune-cytokine IEOmAB1-scFv-hTNFα is able to significantly delay growth of relapsed and chemo-resistant hT-ALLs.

Anti-Leukemic Effect of the scFv-TNFα Fusion Depends on its Stable Binding to hT-ALL Cells.

Figure 2A:
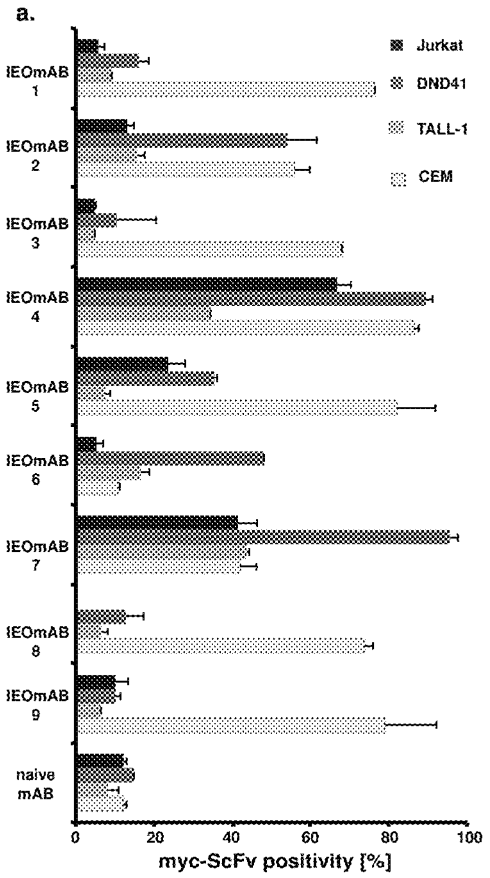
Figure 2B:
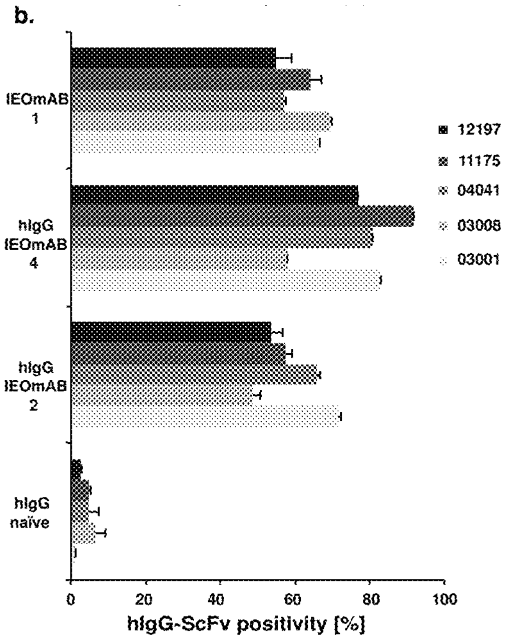
Figure 2C:
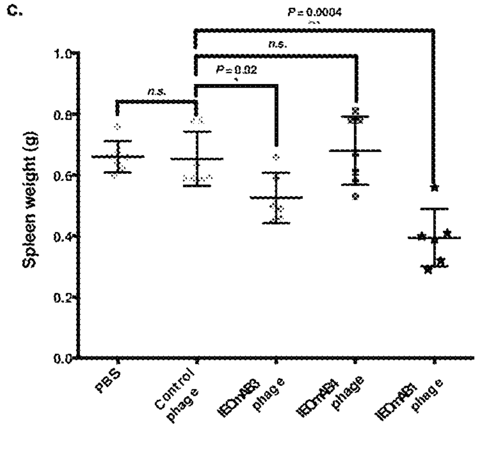
Figure 2D:
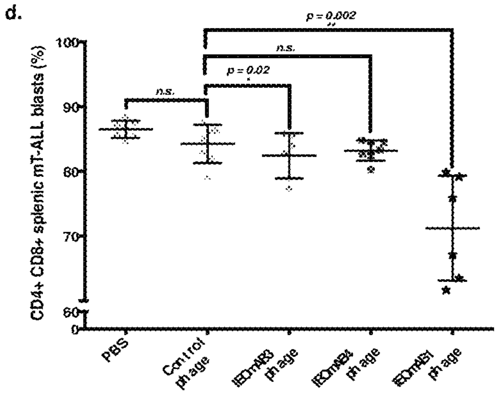
Figure 2E:
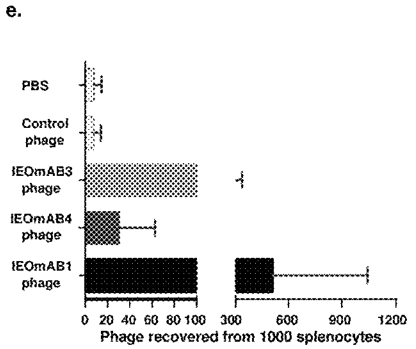
Figure 2F:
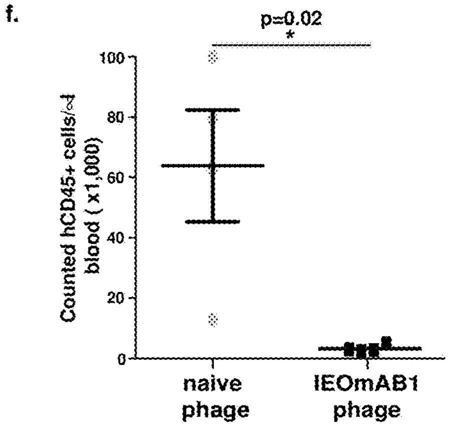
Figure 2G:
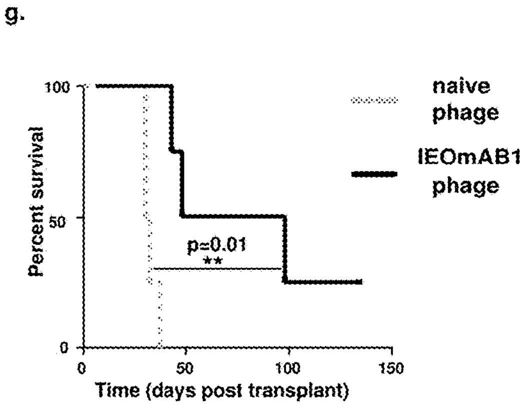
Figure 3H:
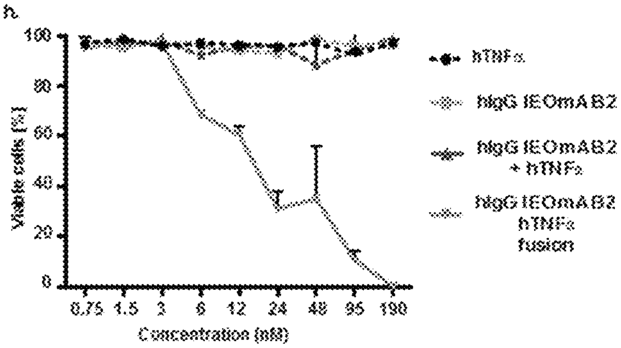

Inventors then analyzed mechanisms underlying the in vivo anti-tumor effects of the IEOmAB1 immuno-cytokine, using cells from the #03008 hT-ALL PDX and CEM, an hT-ALL cell line bound by the IEOmAB1-Myc-scFv (FIG. 2*a-b*). Treatment of #03008 and CEM cells with soluble TNFα or purified IEOmAB1-scFv-hTNFα immune-cytokine induced cytotoxicity, thus demonstrating that these cells are TNFα-sensitive and that TNFα retains its activity in the context of the immune-cytokine (Fig.S2). To investigate whether toxicity of IEOmAB1-scFv-hTNFα depends on binding of the immune-cytokine to T-ALL cells, cells were co-incubated on ice for 30 minutes with equimolar concentrations of soluble or scFv-conjugated hTNFα, washed and re-suspended in growth medium. Under these experimental conditions, TNFα plus the control-scFv-hTNFα failed to kill the TNFα-sensitive CEM (FIG. 3*f*) or #03008 hT-ALL cells (FIG. 3*g*) at any concentration tested, while treatment with IEOmAB1-scFv-hTNFα induced dose-dependent cytotoxicity. To support the conclusion that the antibody mediated interaction with cells is required for the cytotoxic effect of the cytokine-fusions, inventors also produced a second immuno-cytokine, hIgG-IEOmAB2-scFv-hTNFα able to bind CEM and 03008 hT-ALLs (FIG. 2*a-b*). hIgG-IEOmAB2-scFv-hTNFα mediated dose-dependent in vitro cytotoxicity (FIG. 3*f-g*) similar to that observed with IEOmAB1-scFv-hTNFα. However, when administered as unfused hIgG-IEOmAB2-scFv plus hTNFα, there was no effect, indicating that intact immuno-cytokine is required to mediate binding-dependent cell death (FIG. 3*h*). Thus, only the immune-cytokine is able to kill hT-ALL cells in vitro, likely due to its unique property to allow stable interaction of TNFα with T-ALL cells.

T-ALL selected immune-cytokines exert in vivo anti-tumor activity against human metastatic melanoma. Inventors next investigated cross-reactivity of our lead scFv with other tumor types using the IEOmAB1 immuno-cytokine and two other selected scFv (IEOmAB3 and IEOmAB2) reconstructed as fully human immune-cytokines (IEOmAB3- and IEOmAB2-hIgG-scFv-TNFα; see Methods). The three immune-cytokines were produced in HEK-293T human cells, purified and tested for binding against 29 human tumor cell-lines of different origin. They bound very poorly to epithelial tumors or other types of leukemia, while showing a strong cross-reactivity with tumors of embryonic/neuro-ectodermal origin (brain tumors, Ewing's sarcomas, melanomas and malignant embryonal carcinoma)[24] (FIG. 8*a*). Inventors then focused on melanomas, and analyzed in more detail cross-reactivity against a panel of human metastatic melanomas (11 cell lines and 3 PDXs). Remarkably, all 3 immuno-cytokines bound well across the samples, though with slightly different binding patterns (IEOmAB1: 13/14; IEOmAB2: 12/14; IEOmAB3: 5/14) (FIG. 8*b*).

Inventors then evaluated the anti-tumor activity of the three immune-cytokines upon intra-tumoral or systemic administration to melanoma-bearing mice. As a model system, inventors used the MM27 PDX[25], which showed strong binding to all three immune-cytokines (FIG. 8*b*). MM27 cells were intra-dermically transplanted onto the backs of NSG mice and allowed to reach ≈30 $mm^2$ before commencing treatment. For the intra-tumoral administration-protocol, tumor lesions were injected daily with equimolar doses of immune-cytokines for up to 1 week (≈0.1 mg/kg/mouse/day). Remarkably, all three immune-cytokines delayed tumor growth (FIGS. 4*a* and 4*c*) and prolonged significantly the time-to-sacrifice of treated mice, compared to control immune-cytokines (FIGS. 4*b* and 4*d*). Systemically treated mice were injected intravenously three times per week with 0.25 mg/kg of the IEOmAB1-scFv-TNFα cytokine and sacrificed when tumors reached the maximal dimension allowed (≈120 mm2). Mice receiving IEOmAB1-scFv-TNFα showed visible necrosis and ulceration (not shown), a significant delay in melanoma growth (FIG. 4*e*) and a significant extension of time-to-sacrifice compared to PBS or control-scFv-TNFα (FIG. 4*f*). Thus, the immune-cytokines-selected against T-ALLs also exert anti-tumor activity against human metastatic melanoma.

Melanoma Cells are TNFα-Resistant, Yet their Sensitivity to scFv-TNFα Depends Upon Tumor Binding of the Immune-Cytokine.

Inventors then analyzed the mechanisms underlying the anti-melanoma effects of the tested immune-cytokines. Surprisingly, in vitro treatment of A375 or MM27 melanoma cells with soluble hTNFα or scFv-fused-hTNFα failed to induce cytotoxicity in vitro, as shown by the Trypan blue exclusion test (FIG. 4*g-h*) and quantitation of cleaved caspase-3 (not shown), demonstrating that melanoma cells are hTNFα-resistant. Consistently, the same cells expressed undetectable or negligible levels of hTNFα-receptor (TNFR1) compared to the hTNFα-sensitive hT-ALLs (FIG. 9). To ensure that their in vivo activities were indeed exerted by the intact fusion-protein, MM27 tumors were injected intra-tumorally with the intact immune-cytokine (IEOmAB3-hIgG-scFv-TNFα), with the IEOmAB3 antibody (IEOmAB3-hIgG-scFv) together with soluble TNFα, or with TNFα alone. As expected, the intact immune-cytokine retarded tumor growth, while administration of soluble hTNFα or the IEOmAB3-hIgG-scFv antibody combined with soluble hTNFα did not (FIG. 10*a*). Finally, to confirm that the in vivo anti-tumor effect of the immune-cytokine was binding-dependent, inventors used the IEOmAB3 immuno-cytokine to treat MM13 PDX[25], a human melanoma that is not bound by the IEOmAB3-hIgG-scFv-TNFα antibody (FIG. 8*b*). MM13 lesions treated intra-tumorally with IEOmAB3-hIgG-scFv-TNFα or TNFα alone, did not show any therapeutic benefit as compared to control immune-cytokine or PBS treated animals (FIG. 10*b*). Thus, melanoma cells are hTNFα-resistant both in vitro and in vivo and resistant to the scFv-TNFα immune-cytokines in vitro. In vivo sensitivity to immune-cytokines depends on their integrity as antibody-hTNFα fusion-proteins and binding to tumor cells, suggesting that the immune-cytokine must be sufficiently retained within melanomas to induce an anti-tumor response.

Immuno-Cytokines Modulate Host Inflammation within Melanoma Tumors.

Figure 5A:
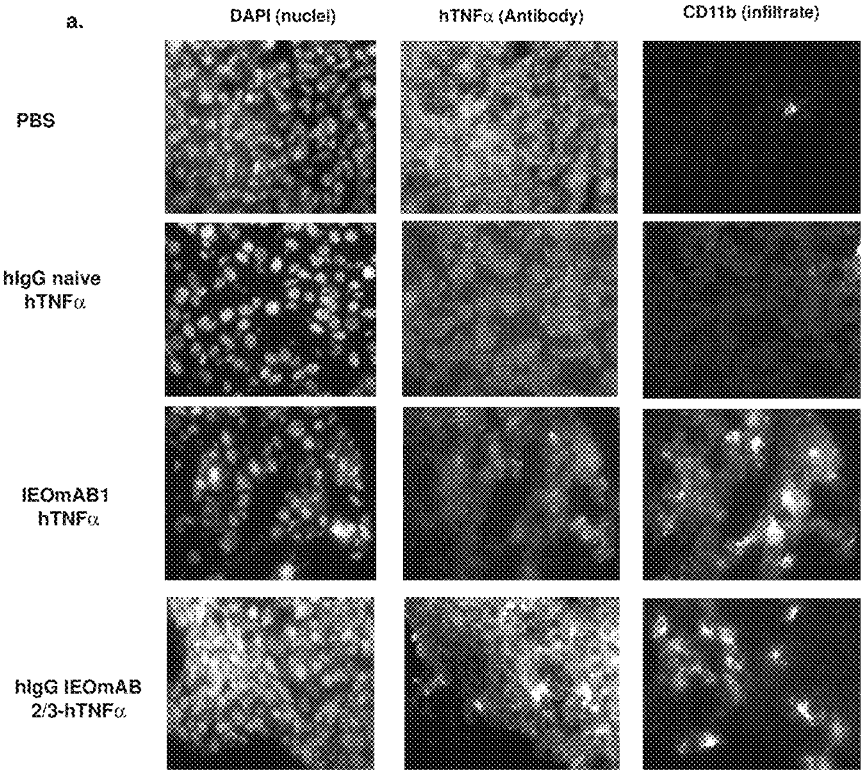
Figure 5B:
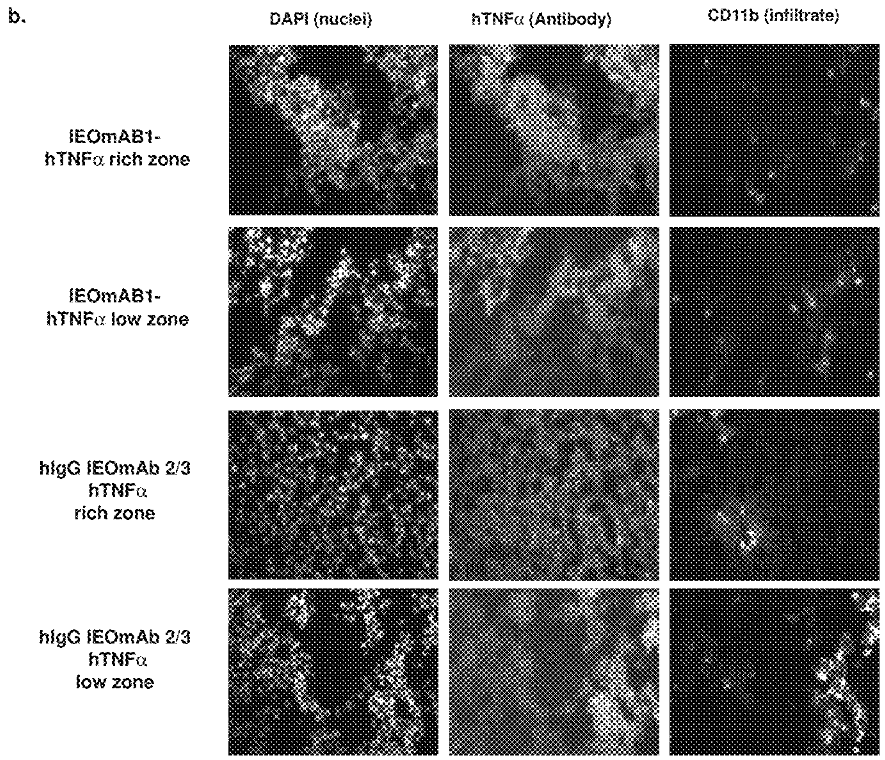
Figure 5C:
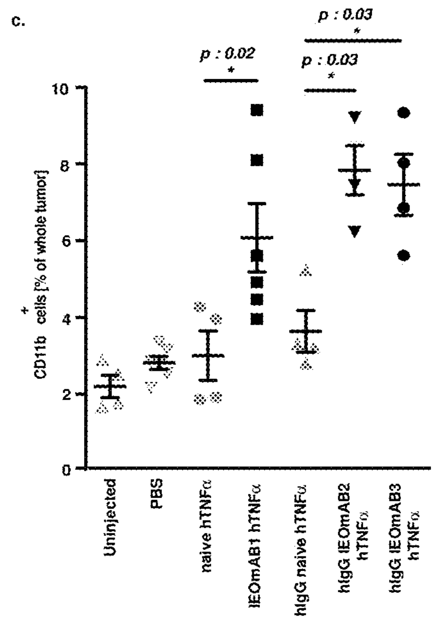
Figure 5D:
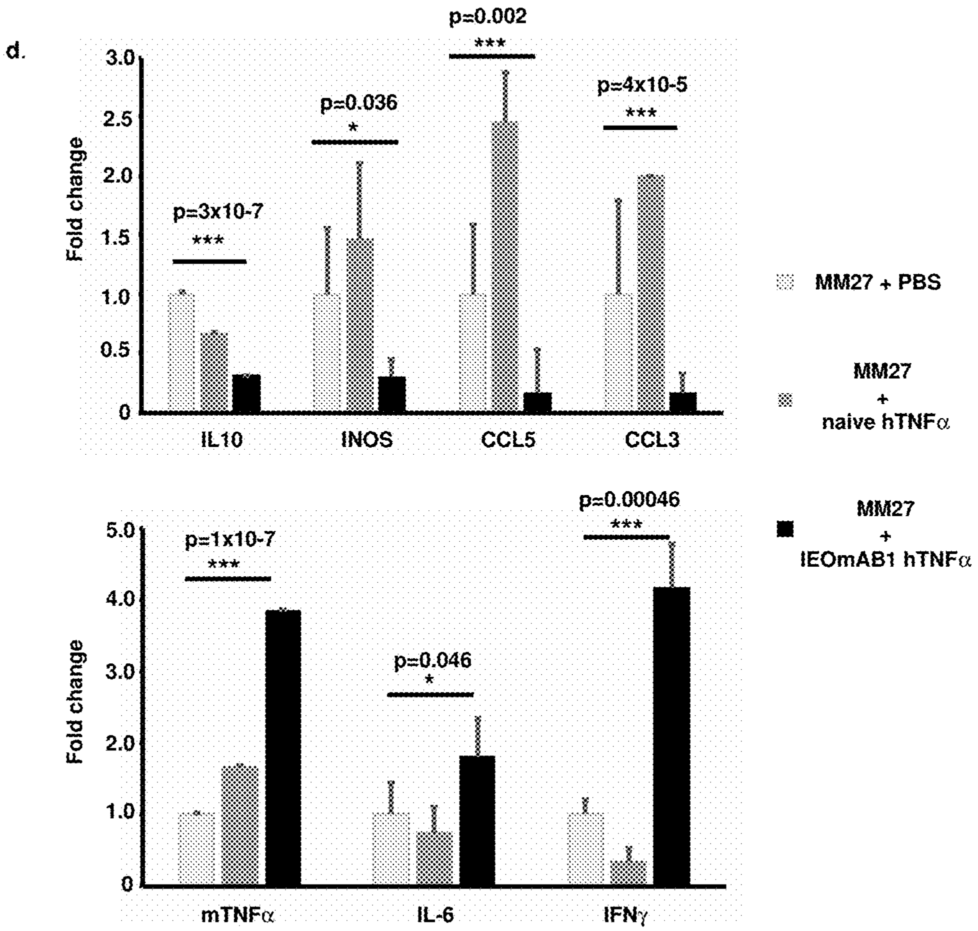

Inventors next investigated putative mechanisms of in vivo toxicity of the three immune-cytokines. Large (50-70 $mm^2$) MM27 xenograft tumors were injected with equimolar doses of each of the three immune-cytokines (IEOmAB1-scFv-TNFα; IEOmAB2- or IEOmAB3-hIgG-scFv-TNFα) and 24 hours later mice were sacrificed, tumors excised and evaluated for cell viability. All three immune-cytokines markedly reduced cell viability revealed by Trypan Blue analyses of cell suspensions compared to controls (e.g. PBS, soluble hTNFα, control-hIgG-scFv-TNFα, and control-scFv-hTNFα) (FIG. 11*a*). However, when examined histologically, tumors treated with the three tumor-binding immune-cytokines did not display detectable levels of cleaved caspase-3 (FIG. 11*b*), indicating that in vivo immune-cytokine-toxicity is not mediated by a direct effect of TNFα, consistent with previous in vitro observations (FIG. 4*g-h*). To test whether the pro-inflammatory effects of targeted hTNFα mediate the in vivo toxicity of the three tumor-binding immune-cytokines, inventors evaluated the myeloid tumor-infiltrate (B, T and NK cells being absent in NSG mice). Disaggregated tumor cells were analyzed by flow-cytometry and immunohistochemistry for expression of the pan-myeloid marker CD11b, as well as for a number of other myeloid sub-population lineage-markers, including neutrophils (Gr1-high and CD11b-low), macrophages (CD11b-high and F4/80+), dendritic cells (CD11b+ and CD11c+), monocytes (CD11b+, Ly6C+ and Gr1low) and myeloid derived suppressor cells (CD11b+, Gr1-high and CD206+). Both analyses (FIG. 5*a-b*, representative results) showed a significantly increased infiltration of CD11b+ cells after treatment with all three immune-cytokines (IEOmAB2- or IEOmAB3-hIgG-scFv-hTNFα and IEOmAB1-scFv-hTNFα) compared to controls (e.g. PBS, soluble hTNFα, control-hIgG-scFv-TNFα, and control-hTNFα). Myeloid sub-population investigation showed a parallel increase of all myeloid sub-populations upon all three treatments (with the exception of consistently unchanged myeloid suppressor cell levels). Inventors then analyzed the relative distribution of the immune-cytokine and CD11b+ cells in sections of IEOmAB1-Myc-scFv-hTNFα treated tumors, by simultaneous immunofluorescence analyses of immune-cytokine localization (using anti-hTNFα antibodies) and CD11b+ cell-distribution). Both the IEOmAB1-scFv-hTNFα immune-cytokine and the combined IEOmAB2-+IEOmAB3-hIgG-scFv-TNFα immuno-cytokines were visualized in large cytoplasmic vacuoles inside tumor cells, suggesting active endocytosis of the bound antigens. However, recruitment of $CD11b^+$ cells was not limited to tumor areas with detectable immuno-cytokine protein (FIG. 5*c*), suggesting that the membrane-anchored immune-cytokine triggered a self-perpetuating inflammatory response that eventually extended to the entire tumor. TNFα is a central player in the regulation of numbers and function of tumor-associated CD11b+ cells, including tumor-associated macrophages (TAMs). It induces further TNFα-production by CD11b+ cells and consequent recruitment and activation of macrophages. In particular, TNFα shifts the different TAM activation states from the pro-tumor M2 to the anti-tumor M1 phenotypes[26]. Inventors investigated expression of several TAM1/TAM2-specific cytokine RNAs produced by the local microenvironment in tumor cell extracts, using PCR assays specific for mouse sequences. Strikingly, in the IEOmAB1-scFv-hTNFα treated samples, inventors found activation of several pro-inflammatory genes (IL6, IFNγ, mTNFα), and down-regulation of several immune-suppressive genes (IL10, CCL3, CCL5, and INOS) (FIG. 5*d*), consistent with TNFα-induced M1 polarization of tumor-infiltrating macrophages.

TABLE 1

Summary of the binding of Immuncytokine proteins to healthy human tissue arrays

| | IEOmAB1-scFv-hTNFα | hIgG-IEOmAB2-scFv-hTNFα | hIgG-IEOmAB3-scFv-hTNFα | hIgG-Control-scFv-hTNFα |
|---|---|---|---|---|
| Cerebellum | Negative | Negative | Negative | Negative |
| Bone marrow | Negative | Negative | Negative | Negative |
| Skin | Background | Negative | Negative | Negative |
| Spleen | Negative | Negative | Negative | Negative |
| Small intestine | Negative | Negative | Background | Negative |
| Esophagus | Negative | Negative | Negative | Negative |
| Heart | Negative | Background | Background | Negative |
| Colon | Negative | Negative | Negative | Negative |
| Cerebrum | Background | Background | Background | Negative |
| Kidney | Background | Background | Background | Negative |
| Liver | Background | Background | Background | Background |
| Lung | Background | Background | Background | Negative |
| Pancreas | Background | Background | Background | Background |
| Skeletal muscle | Negative | Background | Negative | Negative |
| Stomach | Negative | Negative | Negative | Negative |
| Thyroid | Negative | Background | Background | Negative |
| Thymus | Positive | Positive | Positive | Negative |
| Placenta | Negative | Negative | Negative | Negative |
| Prostata | Negative | Background | Background | Negative |
| Salivary gland | Background | Background | Background | Negative |
| Peripheric nerve | Negative | Negative | Negative | Negative |
| Tonsille | Negative | Negative | Negative | Negative |
| Testis | Background | Background | Negative | Negative |
| Cervix | Negative | Negative | Negative | Negative |
| Adrenal | Negative | Negative | Negative | Negative |
| Uterus | Background | Background | Background | Negative |
| Pituitary | Negative | Negative | Negative | Negative |
| Mesothelial cell | Negative | Negative | Negative | Negative |
| Ovary | Background | Background | Background | Negative |

Staining and scoring of immunohistochemical signal for immunocytokine probed healthy human tissue arrays was performed by an independent pathologist, without prior knowledge of the antibodies being used or the predicted tissue binding patterns. Each score is representative for each of the three human patient-derived specimens for each of the listed tissues. Binding was judged as positive, negative or background (non-specific) and scoring was validated by an independent pathologist technician not involved in the experiment. Immunocytokine-dependent signal was obtained in comparison to a hematoxylin-stained, immunocytokine-free tissue array. The only tissue found to have specific binding for IEOmAB1-scFv-hTNFα, IEOmAB2-scFv-hTNFα, IEOmAB3-scFv-hTNFα was the thymus. All other healthy human tissues gave non-specific binding or no detectable signal. The results would suggest that the 3 candidate antibodies are unlikely to have serious off-tumor binding to essential organs, thus rendering their tumor binding more specific and diminishing the likelihood of systemic collateral effects related to undesirable antibody binding.

DISCUSSION

The use of tumor-targeting antibody therapies has proven a game-changer in cancer treatment. Whether functioning as stand-alone passive immunotherapies or providing the specificity for active immunotherapy approaches, tumor-specific antibodies are the lynchpin. Classical immunotherapy approach begins with the identification of an appropriate antigen, generation of monoclonal antibodies against it, evaluation of their anti-tumor effector function, and format optimization for clinical setting. Development can take years as many obstacles hinder the obtainment of the final product. Indeed, the discovery and validation of antibodies versus true tumor-associated antigens is a rate-limiting step in this process that hampers the application of immunotherapies to the majority of neoplasia (reviewed in Sanchez-Martin[12]).

Inventors have sought to adapt and streamline a robust platform for the discovery and pre-clinical validation of tumor-targeting antibodies in an unbiased, high-throughput manner. To maximize the capacity to select bona fide human antibodies, inventors used phage-antibody (scFv) synthetic library ETH2-Gold[20] in an in vivo setting. In doing so, inventors maximized the possibility of selecting human antibodies targeting accessible antigens in the most relevant setting of a living, immune-competent animal. The in vivo setting provides the physiological selective pressure (immune editing) that shapes the genotype and phenotype of a viable tumor, which may be lost when relying upon cultured cells[13,27,28]. To instead minimize toxicity in the form of off-tumor binding, inventors have depleted the phage library both in- and ex-vivo versus healthy tissues. Screening steps were then implemented to assay tumor specificity ex vivo (flow cytometry) as well as determine tumor specificity in vivo (phage accumulation assays).

While the single steps of the screening workflow for anti-tumor therapeutic antibody-phages may be not novel, their combination as devised here has never been previously reported. Being unbiased towards the targeted tumor antigen it allows for the discovery of novel binders. Clearly, the possibility of cross-reactivity with normal tissues still remains, albeit, even conventional target-based immunotherapies against the best-characterized antigens have high attrition rates due to unforeseen off-tumor effects[29,30].

Anticipating the selection stages into immune-competent model organisms and then screening phage-antibody candidates for their tumor-binding properties in vitro and in vivo can minimize the risk of off-target effects. One could argue that the reliance of such screening platforms upon recombinant antibody fragments (such as scFvs) could create immunogenic moieties limiting their effectiveness[31]. However, CAR-T cell therapies containing tumor-targeting scFvs have been found in treated patients many years post-therapy, indicating that the scFv moiety is not necessarily immunogenic[32]. In addition, the use of chimeric antibodies, which is the current gold standard, is itself subject to such immunogenicity concerns[33,34]. Furthermore, it should be noted that the ETH2-Gold scFv is fully human, limiting potential immunogenicity inherent to murine-derived scFvs[20]. By combining in vivo panning and thorough healthy tissue depletion with simple screening steps to interrogate in vivo specificity, these concerns are largely ameliorated.

The workflow proposed reverses the order of classical antibody generation steps exploiting phage bio-localization to rapidly determine which scFv molecules have the greatest tumor-specificity and the best chance at eliciting an acute or prolonged anti-tumor effect via its inherent, in vivo immunodominant aspects. This step can be performed without time-consuming purification methods or complex biochemistry. In a few days a phage-antibody clone can be produced, injected and evaluated. This allows for the funneling of candidate antibodies towards those with the highest chance of eliciting a specific anti-tumor immune response.

This rapid, yet rigorous screening approach allowed for the identification of several non-redundant scFv molecules targeting murine T-ALL. The production of those from bacterial cultures allowed testing their cross-reactivity versus a large number of human specimens and cell-lines. Inventors found that the majority (9/10) of candidate scFvs preselected for binding preferentially to tumor cells rather than to normal WT cells strongly labeled hT-ALL cells suggesting an important inter-species antigen conservation. Binding to hT-ALL samples and in vivo phage activity guided and streamlined the selection and identification of the lead candidate antibody (IEOmAB1) that was subsequently engineered as a TNFα-fused immuno-cytokine endowed with potent anti-leukemic and melanoma activity in vivo. As inventors wanted to determine the in vivo efficacy of our antibody candidates against growing human PDX tumors, inventors utilized the NSG immune-compromised mouse system. NSG mice lack both complement and natural killer cells, therefore antibody dependent cytotoxicity is ablated. Consequently, inventors chose to genetically conjugate present antibodies to proteinaceous immunotoxins to better mimic the tumoricidal effects observed in phage treatments. Interestingly, fusion of tumor-targeting antibodies to TNFα has already shown great promise in a clinical setting,[35-37], however their application has been limited to direct tumor administration. This is the first description of systemically injected TNFα-antibody fusions able to elicit an anti-tumor effect in vivo as single agents.

Importantly, IEOmAB1-scFv manifested durable, reproducible and significant delay in disease progression in 4 independent hT-ALL PDXs, when administered as phage. Inventors then treated the most aggressive of these cases, 03008, and found that TNFα-fused IEOmAB1-scFv significantly delayed the on-set of leukemia when given at an early stage (FIG. 3*a*) as well as after the leukemia was already detectable (FIG. 3*e*). In both settings, IEOmAB1-scFv-hTNFα significantly extended the lifespan of treated animals as compared to controls.

Clinical trials of recombinant TNFα as a cancer treatment were often associated with serious general toxicities[38,39], interfering with its clinical use. Importantly, IEOmAB1-scFv-hTNFα did not show notable toxicities, despite repeated intravenous boluses. Therefore, the dose administered was insufficient to trigger general toxicity, but sufficient to suppress tumor growth in mice. This likely occurs by the antibody-dependent anchoring of TNFα upon the plasma membrane increasing the local concentration above the threshold necessary to trigger either direct or indirect anti-tumor effects. Therefore, scFv-TNFα dependent cell death must be mediated by an antibody: antigen interaction whose affinity exceeds that of free TNFα for its receptor. Interestingly, inventors found 3 antibodies [hIgG IEOmAB3 hTNFα, hIgG IEOmAB2 hTNFα and IEOmAB1 hTNFα] that consistently labeled human tumor cells of neuro-ectodermal origin suggesting perhaps cross-reactivity with an exposed cancer/embryonic antigen (FIG. 8*a*). This observation suggests that the in vivo and ex vivo competitive depletion steps are crucial to bias selection towards uncommon antigens increasing the likelihood of retrieval of antibodies endowed with higher specificity. Being able to evaluate cross-reactivity at such an early stage contributed to the prioritization of candidate scFvs with the broadest potential clinical applicability. In fact, when tested against healthy human tissue specimens in an FDA-approved tissue array, none of the three antibodies exhibited specific, significant binding to any vital organs. The only tissue to which the antibodies bound were to healthy human thymus. The binding to healthy human thymus tissues is not per sé counter-indicative, as the thymus is largely atrophied by adolescence. Therefore in adult tumors there should be no impediments to therapeutic use. In childhood tumors, it might be more problematic, however thymectomy in childhood cancer is performed in cases of myasthenia gravis and thymomas, without life-threatening consequences[46]. Furthermore, therapeutic antibody targeting of T cell lymphomas via the CD4 protein (Zanolimumab) have been shown to be generally well tolerated despite a similar reactivity with human thymus resident cells[47]. In closing, inventors strongly believe this workflow can be tailored and applied to virtually any tumor model and will lead to the identification of novel immunotherapies through the in vivo selection of specificity and evaluation of tumoricidal efficacy. As such, the platform described herein provides a rational, high-throughput, rapid workflow to discover and pre-clinically validate treatment options for the benefit of patients.

Sequences

Included in the present invention are also nucleic acid or aa. sequences derived from the sequences shown below, e.g. functional fragments, mutants, derivatives, analogues, and sequences having a % of identity of at least 70% with the below sequences.

```
scFv DP47-DPL16 [prototype sequence,
indicative of general scFv structure]
                                   (SEQ ID NO: 1)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKXX

XXDYWGQGTLVTVSSGGGGSGGGGSGGGGSSELTQDPAVSVALGQTVRIT
```

-continued

CQGDSLRSYYASWYQQKPGQAPVLVIYGKNNRPSGIPYRFSGSSSGNTAS

LTITGAQAEDEADYYCNSSXXXXXXXVVFGGGTKLTVLG underlined: library VH domain
bold: CDR3 heavy chain sequence
cursive: linker region
in block and not underlined: library VL domain
grey: CDR3 light chain sequence
XXXX: CDR3 sequences or mutations from the library backbone In the below sequences, the sequences in bold correspond (from left to right) to DP47 Human heavy chain CDR1, DP47 Human Heavy Chain CDR2, DP47 Human Heavy Chain CDR3, DPL16 Human Lambda Light Chain CDR1, DPL16 Human Lambda Light Chain CDR2, DPL16 Human Lambda Light Chain CDR3.

IEOmAB1 amino acid sequence
(SEQ ID NO: 2)
EVQLLESGGGLAQPGGSLRLSCAASGFTFSSYAMSWVRQAPGKGLEWVSAISGSGGSTYY

ADSVKGRFTISRDNSKNTLYLQMNSLRAEDTAVYYCAKSVTRFDYWGQGTLVTVSSGGG

GSGGGGSGGGGSSELTQDPAVSVALGQTVRITCQGDSLRSYYASWYQQKPGQAPVLVIYG

KNNRPSGIPYRFSGSSSGNTASLTITGAQAEDEADYYCNSSRGLARPVVVGGGTKLTVLG

IEOmAB1 DNA sequence
(SEQ ID NO: 3)
GAGGTGCAGCTGTTGGAGTCTGGGGGAGGCTTGGCACAGCCTGGGGGGTCCCTGAGAC

TCTCCTGTGCAGCCTCTGGATTCACCTTTAGCAGCTATGCCATGAGCTGGGTCCGCCAG

GCTCCAGGGAAGGGGCTGGAGTGGGTCTCAGCTATTAGTGGTAGTGGTGGTAGCACAT

ACTACGCAGACTCCGTGAAGGGCCGGTTCACCATCTCCAGAGACAATTCCAAGAACAC

GCTGTATCTGCAAATGAACAGCCTGAGAGCCGAAGACACGGCCGTATATTACTGTGCG

AAATCTGTTACTCGTTTTGACTACTGGGGCCAGGGAACCCTGGTCACCGTCTCGAGTGG

TGGAGGCGGTTCAGGCGGAGGTGGCTCTGGCGGTGGCGGATCGTCTGAGCTGACTCAG

GACCCTGCTGTGTCTGTGGCCTTGGGACAGACAGTCAGGATCACATGCCAAGGAGACA

GTCTCAGAAGCTATTATGCAAGCTGGTACCAGCAGAAGCCAGGACAGGCCCCTGTACT

TGTCATCTATGGTAAAAACAACCGGCCCTCAGGGATCCCATACCGATTCTCTGGCTCCA

GCTCAGGAAACACAGCTTCCTTGACCATCACTGGGGCTCAGGCGGAAGATGAGGCTGA

CTATTACTGTAACTCCTCTAGGGGGCTGGCGCGGCCCGTGGTAGTCGGCGGAGGGACC

AAGCTGACCGTCCTAGGC

IEOmAB2 amino acid sequence
(SEQ ID NO: 4)
EVQLLESGGGLVQPGGSLRLSCAASGFTFSSYAMSWVRQAPGKGLEWVSAISGSGGSTYY

ADSVKGRFTISRDNSKNTLYLQMNSLRAEDTAVYYCAKTASILDYWGQGTLVTVSSGGGG

SGGGGSGGGGSSELTQDPAVSVALGQTVRITCQGDSLRSYYASWYQQKPGQAPVLVIYGK

NNRPSGIPYRFSGSSSGNTASLTITGAQAEDEADYYCNSSPWHRTSVVFGGGTKLTVLG

IEOmAB2 DNA sequence
(SEQ ID NO: 5)
GAGGTGCAGCTGTTGGAGTCTGGGGGAGGCTTGGTACAGCCTGGGGGGTCCCTGAGAC

TCTCCTGTGCAGCCTCTGGATTCACCTTTAGCAGCTATGCCATGAGCTGGGTCCGCCAG

GCTCCAGGGAAGGGGCTGGAGTGGGTCTCAGCTATTAGTGGTAGTGGTGGTAGCACAT

ACTACGCAGACTCCGTGAAGGGCCGGTTCACCATCTCCAGAGACAATTCCAAGAACAC

GCTGTATCTGCAAATGAACAGCCTGAGAGCCGAAGACACGGCCGTATATTACTGTGCG

AAAACGGCTTCTATTCTTGACTACTGGGGCCAGGGAACCCTGGTCACCGTCTCGAGTGG

TGGAGGCGGTTCAGGCGGAGGTGGCTCTGGCGGTGGCGGATCGTCTGAGCTGACTCAG

GACCCTGCTGTGTCTGTGGCCTTGGGACAGACAGTCAGGATCACATGCCAAGGAGACA

GTCTCAGAAGCTATTATGCAAGCTGGTACCAGCAGAAGCCAGGACAGGCCCCTGTACT

-continued

TGTCATCTATGGTAAAAACAACCGGCCCTCAGGGATCCCATACCGATTCTCTGGCTCCA

GCTCAGGAAACACAGCTTCCTTGACCATCACTGGGGCTCAGGCGGAAGATGAGGCTGA

CTATTACTGTAACTCCTCTCCCTGGCATCGTACTAGTGTGGTATTCGGCGGAGGGACCA

AGCTGACCGTCCTAGGC

IEOmAB3 amino acid sequence (SEQ ID NO: 6)

EVQLLESGGGLVQPGGSLRLSCAASGFTFSSYAMSWVRQAPGKGLEWVSAISGSGGSTYY

ADSVKGRFTISRDNSKNTLYLQMNSLRAEDTAVYYCAKVMGRNAFDYWGQGTLVTASSG

GGGSGGGGSGGGGSSELTQDPAVSVALGQTVRITCQGDSLRSYYASWYQQKPGQAPVLVI

YGKNNRPSGIPYRFSGSSSGNTASLTITGAQAEDEADYYCNSSPPTPDTVVFGGGTKLTVL

G

IEOmAB3 DNA sequence (SEQ ID NO: 7)

GAGGTGCAGCTGTTGGAGTCTGGGGGAGGCTTGGTACAGCCTGGGGGGTCCCTGAGAC

TCTCCTGTGCAGCCTCTGGATTCACCTTTAGCAGCTATGCCATGAGCTGGGTCCGCCAG

GCTCCAGGGAAGGGGCTGGAGTGGGTCTCAGCTATTAGTGGTAGTGGTGGTAGCACAT

ACTACGCAGACTCCGTGAAGGGCCGGTTCACCATCTCCAGAGACAATTCCAAGAACAC

GCTGTATCTGCAAATGAACAGCCTGAGAGCCGAAGACACGGCCGTATATTACTGTGCG

AAAGTGATGGGTCGGAATGCTTTTGACTACTGGGGCCAGGGAACCCTGGTCACCGCCTC

GAGTGGTGGAGGCGGTTCAGGCGGAGGTGGCTCTGGCGGTGGCGGATCGTCTGAGCTG

ACTCAGGACCCTGCTGTGTCTGTGGCCTTGGGACAGACAGTCAGGATCACATGCCAAG

GAGACAGTCTCAGAAGCTATTATGCAAGCTGGTACCAGCAGAAGCCAGGACAGGCCCC

TGTACTTGTCATCTATGGTAAAAACAACCGGCCCTCAGGGATCCCATACCGATTCTCTG

GCTCCAGCTCAGGAAACACAGCTTCCTTGACCATCACTGGGGCTCAGGCGGAAGATGA

GGCTGACTATTACTGTAACTCCTCTCCGCCCACTCCTGATACGGTGGTATTCGGCGGAG

GGACCAAGCTGACCGTCCTAGGC hTNFα DNA sequence (SEQ ID NO: 8)

ATGGTCAGATCATCTTCTCGAACCCCGAGTGACAAGCCTGTAGCCCATGTTGTAGCAAA

CCCTCAAGCTGAGGGGCAGCTCCAGTGGCTGAACCGCCGGGCCAATGCCCTCCTGGCC

AATGGCGTGGAGCTGAGAGATAACCAGCTGGTGGTGCCATCAGAGGGCCTGTACCTCA

TCTACTCCCAGGTCCTCTTCAAGGGCCAAGGCTGCCCCTCCACCCATGTGCTCCTCACCC

ACACCATCAGCCGCATCGCCGTCTCCTACCAGACCAAGGTCAACCTCCTCTCTGCCATC

AAGAGCCCCTGCCAGAGGGAGACCCCAGAGGGGGCTGAGGCCAAGCCCTGGTATGAG

CCCATCTATCTGGGAGGGGTCTTCCAGCTGGAGAAGGGTGACCGACTCAGCGCTGAGA

TCAATCGGCCCGACTATCTCGACTTTGCCGAGTCTGGGCAGGTCTACTTTGGGATCATT

GCCCTGTGA hTNFα amino acid sequence (SEQ ID NO: 29)

MVRSSSRTPSDKPVAHVVANPQAEGQLQWLNRRANALLANGVELRDNQLVVPSEGLYLIY

SQVLFKGQGCPSTHVLLTHTISRIAVSYQTKVNLLSAIKSPCQRETPEGAEAKPWYEPIYLGG

VFQLEKGDRLSAEINRPDYLDFAESGQVYFGIIAL* hIgG1-Fc tag DNA sequence (SEQ ID NO: 9)

ATATCGGCCATGGTTAGATCTGACAAAACTCACACATGCCCACCGTGCCCAGCACCTGA

ACTCCTGGGGGGACCGTCAGTCTTCCTCTTCCCCCCAAAACCCAAGGACACCCTCATGA

-continued

TCTCCCGGACCCCTGAGGTCACATGCGTGGTGGTGGACGTGAGCCACGAAGACCCTGA

GGTCAAGTTCAACTGGTACGTGGACGGCGTGGAGGTGCATAATGCCAAGACAAAGCCG

CGGGAGGAGCAGTACAACAGCACGTACCGTGTGGTCAGCGTCCTCACCGTCCTGCACC

AGGACTGGCTGAATGGCAAGGAGTACAAGTGCAAGGTCTCCAACAAAGCCCTCCCAGC

CCCCATCGAGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGACCTGCCTGGT

CAAAGGCTTCTATCCCAGCGACATCGCCGTGGAGTGGGAGAGCAATGGGCAGCCGGAG

AACAACTACAAGACCACGCCTCCCGTGCTGGACTCCGACGGCTCCTTCTTCCTCTACAG

CAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGTAA

ATGAGTGCTAGCTGG hIgG1-Fc tag amino acid sequence (SEQ ID NO: 30)

ISAMVRSDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK*

IEOmAB1-scFv-hTNFα DNA sequence (SEQ ID NO 31)

GAGGTGCAGCTGTTGGAGTCTGGGGGAGGCTTGGCACAGCCTGGGGGGTCCCTGAGAC

TCTCCTGTGCAGCCTCTGGATTCACCTTTAGCAGCTATGCCATGAGCTGGGTCCGCCAGG

CTCCAGGGAAGGGGCTGGAGTGGGTCTCAGCTATTAGTGGTAGTGGTGGTAGCACATAC

TACGCAGACTCCGTGAAGGGCCGGTTCACCATCTCCAGAGACAATTCCAAGAACACGCT

GTATCTGCAAATGAACAGCCTGAGAGCCGAAGACACGGCCGTATATTACTGTGCGAAATC

TGTTACTCGTTTTGACTACTGGGGCCAGGGAACCCTGGTCACCGTCTCGAGTGGTGGAG

GCGGTTCAGGCGGAGGTGGCTCTGGCGGTGGCGGATCGTCTGAGCTGACTCAGGACCCT

GCTGTGTCTGTGGCCTTGGGACAGACAGTCAGGATCACATGCCAAGGAGACAGTCTCAG

AAGCTATTATGCAAGCTGGTACCAGCAGAAGCCAGGACAGGCCCCTGTACTTGTCATCTA

TGGTAAAAACAACCGGCCCTCAGGGATCCCATACCGATTCTCTGGCTCCAGCTCAGGAA

ACACAGCTTCCTTGACCATCACTGGGGCTCAGGCGGAAGATGAGGCTGACTATTACTGT

AACTCCTCTAGGGGGCTGGCGCGGCCCGTGGTAGTCGGCGGAGGGACCAAGCTGACCG

TCCTAGGCTCTTCGTCATCGGGATCTTCGTCATCCGGATCTTCGTCATCCGGGATGGTCAG

ATCATCTTCTCGAACCCCGAGTGACAAGCCTGTAGCCCATGTTGTAGCAAACCCTCAAGC

TGAGGGGCAGCTCCAGTGGCTGAACCGCCGGGCCAATGCCCTCCTGGCCAATGGCGTGG

AGCTGAGAGATAACCAGCTGGTGGTGCCATCAGAGGGCCTGTACCTCATCTACTCCCAG

GTCCTCTTCAAGGGCCAAGGCTGCCCCTCCACCCATGTGCTCCTCACCCACACCATCAGC

CGCATCGCCGTCTCCTACCAGACCAAGGTCAACCTCCTCTCTGCCATCAAGAGCCCCTGC

CAGAGGGAGACCCCAGAGGGGGCTGAGGCCAAGCCCTGGTATGAGCCCATCTATCTGGG

AGGGGTCTTCCAGCTGGAGAAGGGTGACCGACTCAGCGCTGAGATCAATCGGCCCGACT

ATCTCGACTTTGCCGAGTCTGGGCAGGTCTACTTTGGGATCATTGCCCTGTGA

-continued

IEOmAB1-scFv-hTNFα amino acid sequence (SEQ ID NO 32)

EVQLLESGGGLAQPGGSLRLSCAASGFTFSSYAMSWVRQAPGKGLEWVSAISGSGGSTYYA

DSVKGRFTISRDNSKNTLYLQMNSLRAEDTAVYYCAKSVTRFDYWGQGTLVTVSSGGGGS

GGGGSGGGGSSELTQDPAVSVALGQTVRITCQGDSLRSYYASWYQQKPGQAPVLVIYGKNN

RPSGIPYRFSGSSSGNTASLTITGAQAEDEADYYCNSSRGLARPVVVGGGTKLTVLGSSSSGS

SSSGSSSSGMVRSSSRTPSDKPVAHVVANPQAEGQLQWLNRRANALLANGVELRDNQLVVP

SEGLYLIYSQVLFKGQGCPSTHVLLTHTISRIAVSYQTKVNLLSAIKSPCQRETPEGAEAKPW

YEPIYLGGVFQLEKGDRLSAEINRPDYLDFAESGQVYFGIIAL*

IEOmAB2-scFv-hIgG-hTNFα DNA sequence (SEQ ID NO: 33)

GAGGTGCAGCTGTTGGAGTCTGGGGGAGGCTTGGTACAGCCTGGGGGGTCCCTGAGAC

TCTCCTGTGCAGCCTCTGGATTCACCTTTAGCAGCTATGCCATGAGCTGGGTCCGCCAGG

CTCCAGGGAAGGGGCTGGAGTGGGTCTCAGCTATTAGTGGTAGTGGTGGTAGCACATAC

TACGCAGACTCCGTGAAGGGCCGGTTCACCATCTCCAGAGACAATTCCAAGAACACGCT

GTATCTGCAAATGAACAGCCTGAGAGCCGAAGACACGGCCGTATATTACTGTGCGAAAA

CGGCTTCTATTCTTGACTACTGGGGCCAGGGAACCCTGGTCACCGTCTCGAGTGGTGGA

GGCGGTTCAGGCGGAGGTGGCTCTGGCGGTGGCGGATCGTCTGAGCTGACTCAGGACC

CTGCTGTGTCTGTGGCCTTGGGACAGACAGTCAGGATCACATGCCAAGGAGACAGTCTC

AGAAGCTATTATGCAAGCTGGTACCAGCAGAAGCCAGGACAGGCCCCTGTACTTGTCAT

CTATGGTAAAAACAACCGGCCCTCAGGGATCCCATACCGATTCTCTGGCTCCAGCTCAGG

AAACACAGCTTCCTTGACCATCACTGGGGCTCAGGCGGAAGATGAGGCTGACTATTACT

GTAACTCCTCTCCCTGGCATCGTACTAGTGTGGTATTCGGCGGAGGGACCAAGCTGACCG

TCCTAGGCATATCGGCCATGGTTAGATCTGACAAAACTCACACATGCCCACCGTGCCCAG

CACCTGAACTCCTGGGGGGACCGTCAGTCTTCCTCTTCCCCCCAAAACCCAAGGACACC

CTCATGATCTCCCGGACCCCTGAGGTCACATGCGTGGTGGTGGACGTGAGCCACGAAGA

CCCTGAGGTCAAGTTCAACTGGTACGTGGACGGCGTGGAGGTGCATAATGCCAAGACAA

AGCCGCGGGAGGAGCAGTACAACAGCACGTACCGTGTGGTCAGCGTCCTCACCGTCCT

GCACCAGGACTGGCTGAATGGCAAGGAGTACAAGTGCAAGGTCTCCAACAAAGCCCTC

CCAGCCCCCATCGAGAAAACCATCTCCAAAGCCAAAGGGCAGCCCCGAGAACCACAGG

TGTACACCCTGCCCCCATCCCGGGATGAGCTGACCAAGAACCAGGTCAGCCTGACCTGC

CTGGTCAAAGGCTTCTATCCCAGCGACATCGCCGTGGAGTGGGAGAGCAATGGGCAGCC

GGAGAACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTCATGCTC

CGTGATGCATGAGGCTCTGCACAACCACTACACGCAGAAGAGCCTCTCCCTGTCTCCGG

GTAAATCTTCGTCATCGGGATCTTCGTCATCCGGATCTTCGTCATCCGGGATGGTCAGATC

ATCTTCTCGAACCCCGAGTGACAAGCCTGTAGCCCATGTTGTAGCAAACCCTCAAGCTG

AGGGGCAGCTCCAGTGGCTGAACCGCCGGGCCAATGCCCTCCTGGCCAATGGCGTGGA

GCTGAGAGATAACCAGCTGGTGGTGCCATCAGAGGGCCTGTACCTCATCTACTCCCAGG

TCCTCTTCAAGGGCCAAGGCTGCCCCTCCACCCATGTGCTCCTCACCCACACCATCAGCC

GCATCGCCGTCTCCTACCAGACCAAGGTCAACCTCCTCTCTGCCATCAAGAGCCCCTGCC

AGAGGGAGACCCCAGAGGGGGCTGAGGCCAAGCCCTGGTATGAGCCCATCTATCTGGG

-continued

AGGGGTCTTCCAGCTGGAGAAGGGTGACCGACTCAGCGCTGAGATCAATCGGCCCGACT

ATCTCGACTTTGCCGAGTCTGGGCAGGTCTACTTTGGGATCATTGCCCTGTGA

IEOmAB2-scFv-hIgG-hTNFα amino acid sequence (SEQ ID NO: 34)

EVQLLESGGGLVQPGGSLRLSCAASGFTFSSYAMSWVRQAPGKGLEWVSAISGSGGSTYYA

DSVKGRFTISRDNSKNTLYLQMNSLRAEDTAVYYCAKTASILDYWGQGTLVTVSSGGGGSG

GGGSGGGGSSELTQDPAVSVALGQTVRITCQGDSLRSYYASWYQQKPGQAPVLVIYGKNNR

PSGIPYRFSGSSSGNTASLTITGAQAEDEADYYCNSSPWHRTSVVFGGGTKLTVLGISAMVRS

DKTHTCPPCPAPELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKTTPPVLDSDGSFFL

YSKLTVDKSRWQQGNVFSCSVMHEALHNHYTQKSLSLSPGKSSSSGSSSSGSSSSGMVRSSS

RTPSDKPVAHVVANPQAEGQLQWLNRRANALLANGVELRDNQLVVPSEGLYLIYSQVLFK

GQGCPSTHVLLTHTISRIAVSYQTKVNLLSAIKSPCQRETPEGAEAKPWYEPIYLGGVFQLEK

GDRLSAEINRPDYLDFAESGQVYFGIIAL*

IEOmAB3-scFv-hIgG-hTNFα DNA sequence (SEQ ID NO: 35)

GAGGTGCAGCTGTTGGAGTCTGGGGGAGGCTTGGTACAGCCTGGGGGGTCCCTGAGAC

TCTCCTGTGCAGCCTCTGGATTCACCTTTAGCAGCTATGCCATGAGCTGGGTCCGCCAGG

CTCCAGGGAAGGGGCTGGAGTGGGTCTCAGCTATTAGTGGTAGTGGTGGTAGCACATAC

TACGCAGACTCCGTGAAGGGCCGGTTCACCATCTCCAGAGACAATTCCAAGAACACGCT

GTATCTGCAAATGAACAGCCTGAGAGCCGAAGACACGGCCGTATATTACTGTGCGAAAG

TGATGGGTCGGAATGCTTTTGACTACTGGGGCCAGGGAACCCTGGTCACCGCCTCGAGT

GGTGGAGGCGGTTCAGGCGGAGGTGGCTCTGGCGGTGGCGGATCGTCTGAGCTGACTC

AGGACCCTGCTGTGTCTGTGGCCTTGGGACAGACAGTCAGGATCACATGCCAAGGAGAC

AGTCTCAGAAGCTATTATGCAAGCTGGTACCAGCAGAAGCCAGGACAGGCCCCTGTACT

TGTCATCTATGGTAAAAACAACCGGCCCTCAGGGATCCCATACCGATTCTCTGGCTCCAG

CTCAGGAAACACAGCTTCCTTGACCATCACTGGGGCTCAGGCGGAAGATGAGGCTGACT

ATTACTGTAACTCCTCTCCGCCCACTCCTGATACGGTGGTATTCGGCGGAGGGACCAAGC

TGACCGTCCTAGGCATATCGGCCATGGTTAGATCTGACAAAACTCACACATGCCCACCGT

GCCCAGCACCTGAACTCCTGGGGGGACCGTCAGTCTTCCTCTTCCCCCCAAAACCCAAG

GACACCCTCATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGCATAATGCCA

AGACAAAGCCGCGGGAGGAGCAGTACAACAGCACGTACCGTGTGGTCAGCGTCCTCAC

CGTCCTGCACCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCCCCGAGAAC

CACAGGTGTACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGAGAGCAATGG

GCAGCCGGAGAACAACTACAAGACCACGCCTCCCGTGCTGGACTCCGACGGCTCCTTCT

TCCTCTACAGCAAGCTCACCGTGGACAAGAGCAGGTGGCAGCAGGGGAACGTCTTCTCA

TGCTCCGTGATGCATGAGGCTCTGCACAACCACTACACGCAGAAGAGCCTCTCCCTGTC

TCCGGGTAAATCTTCGTCATCGGGATCTTCGTCATCCGGATCTTCGTCATCCGGGATGGTC

AGATCATCTTCTCGAACCCCGAGTGACAAGCCTGTAGCCCATGTTGTAGCAAACCCTCAA

-continued

GCTGAGGGGCAGCTCCAGTGGCTGAACCGCCGGGCCAATGCCCTCCTGGCCAATGGCGT

GGAGCTGAGAGATAACCAGCTGGTGGTGCCATCAGAGGGCCTGTACCTCATCTACTCCC

AGGTCCTCTTCAAGGGCCAAGGCTGCCCCTCCACCCATGTGCTCCTCACCCACACCATC

AGCCGCATCGCCGTCTCCTACCAGACCAAGGTCAACCTCCTCTCTGCCATCAAGAGCCC

CTGCCAGAGGGAGACCCCAGAGGGGGCTGAGGCCAAGCCCTGGTATGAGCCCATCTATC

TGGGAGGGGTCTTCCAGCTGGAGAAGGGTGACCGACTCAGCGCTGAGATCAATCGGCC

CGACTATCTCGACTTTGCCGAGTCTGGGCAGGTCTACTTTGGGATCATTGCCCTGTGA

IEOmAB3-scFv-hIgG-hTNFα amino acid sequence (SEQ ID NO: 36)

EVQLLESGGGLVQPGGSLRLSCAASGFTFSSYAMSWVRQAPGKGLEWVSAISGSGGSTYYA

DSVKGRFTISRDNSKNTLYLQMNSLRAEDTAVYYCAKVMGRNAFDYWGQGTLVTASSGGG

GSGGGGSGGGGSSELTQDPAVSVALGQTVRITCQGDSLRSYYASWYQQKPGQAPVLVIYGK

NNRPSGIPYRFSGSSSGNTASLTITGAQAEDEADYYCNSSPPTPDTVVFGGGTKLTVLGISAM

VRSDKTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGKSSSSGSSSSGSSSSGM

VRSSSRTPSDKPVAHVVANPQAEGQLQWLNRRANALLANGVELRDNQLVVPSEGLYLIYSQ

VLFKGQGCPSTHVLLTHTISRIAVSYQTKVNLLSAIKSPCQRETPEGAEAKPWYEPIYLGGVF

QLEKGDRLSAEINRPDYLDFAESGQVYFGIIAL*

IEOmAB2-scFv-hIgG DNA sequence (SEQ ID NO: 37)

GAGGTGCAGCTGTTGGAGTCTGGGGGAGGCTTGGTACAGCCTGGGGGGTCCCTGAGACTCTCCTGTG

CAGCCTCTGGATTCACCTTTAGCAGCTATGCCATGAGCTGGGTCCGCCAGGCTCCAGGGAAGGGGCT

GGAGTGGGTCTCAGCTATTAGTGGTAGTGGTGGTAGCACATACTACGCAGACTCCGTGAAGGGCCGG

TTCACCATCTCCAGAGACAATTCCAAGAACACGCTGTATCTGCAAATGAACAGCCTGAGAGCCGAAG

ACACGGCCGTATATTACTGTGCGAAAACGGCTTCTATTCTTGACTACTGGGGCCAGGGAACCCTGGT

CACCGTCTCGAGTGGTGGAGGCGGTTCAGGCGGAGGTGGCTCTGGCGGTGGCGGATCGTCTGAGCTG

ACTCAGGACCCTGCTGTGTCTGTGGCCTTGGGACAGACAGTCAGGATCACATGCCAAGGAGACAGTC

TCAGAAGCTATTATGCAAGCTGGTACCAGCAGAAGCCAGGACAGGCCCCTGTACTTGTCATCTATGG

TAAAAACAACCGGCCCTCAGGGATCCCATACCGATTCTCTGGCTCCAGCTCAGGAAACACAGCTTCC

TTGACCATCACTGGGGCTCAGGCGGAAGATGAGGCTGACTATTACTGTAACTCCTCTCCCTGGCATC

GTACTAGTGTGGTATTCGGCGGAGGGACCAAGCTGACCGTCCTAGGCATATCGGCCATGGTTAGATC

TGACAAAACTCACACATGCCCACCGTGCCCAGCACCTGAACTCCTGGGGGGACCGTCAGTCTTCCTC

TTCCCCCCAAAACCCAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTGGAGGTGCATAATGC

CAAGACAAAGCCGCGGGAGGAGCAGTACAACAGCACGTACCGTGTGGTCAGCGTCCTCACCGTCCTG

CACCAGGACTGGCTGAATGGCAAGGAGTACAAGTGCAAGGTCTCCAACAAAGCCCTCCCAGCCCCCA

TCGAGAAAACCATCTCCAAAGCCAAAGGGCAGCCCCGAGAACCACAGGTGTACACCCTGCCCCCATC

CCGGGATGAGCTGACCAAGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGACCACGCCTCCCGTGCTGG

ACTCCGACGGCTCCTTCTTCCTCTACAGCAAGCTCACCGTGGACAAGAGCAGGTGGCAGCAGGGGAA

-continued

CGTCTTCTCATGCTCCGTGATGCATGAGGCTCTGCACAACCACTACACGCAGAAGAGCCTCTCCCTG

TCTCCGGGTAAATGA

IEOmAB2-scFv-hIgG amino acid sequence (SEQ ID NO: 38)

EVQLLESGGGLVQPGGSLRLSCAASGFTFSSYAMSWVRQAPGKGLEWVSAISGSGGSTYYADSVKGR

FTISRDNSKNTLYLQMNSLRAEDTAVYYCAKTASILDYWGQGTLVTVSSGGGGSGGGGSGGGGSSEL

TQDPAVSVALGQTVRITCQGDSLRSYYASWYQQKPGQAPVLVIYGKNNRPSGIPYRFSGSSSGNTAS

LTITGAQAEDEADYYCNSSPWHRTSVVFGGGTKLTVLGISAMVRSDKTHTCPPCPAPELLGGPSVFL

FPPKPKDTLMISRTPEVICVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCSVMHEALHNHYTQKSLSL

SPGK*

IEOmAB3-scFv-hIgG DNA sequence (SEQ ID NO: 39)

GAGGTGCAGCTGTTGGAGTCTGGGGGAGGCTTGGTACAGCCTGGGGGGTCCCTGAGAC

TCTCCTGTGCAGCCTCTGGATTCACCTTTAGCAGCTATGCCATGAGCTGGGTCCGCCAGG

CTCCAGGGAAGGGGCTGGAGTGGGTCTCAGCTATTAGTGGTAGTGGTGGTAGCACATAC

TACGCAGACTCCGTGAAGGGCCGGTTCACCATCTCCAGAGACAATTCCAAGAACACGCT

GTATCTGCAAATGAACAGCCTGAGAGCCGAAGACACGGCCGTATATTACTGTGCGAAAG

TGATGGGTCGGAATGCTTTTGACTACTGGGGCCAGGGAACCCTGGTCACCGCCTCGAGT

GGTGGAGGCGGTTCAGGCGGAGGTGGCTCTGGCGGTGGCGGATCGTCTGAGCTGACTC

AGGACCCTGCTGTGTCTGTGGCCTTGGGACAGACAGTCAGGATCACATGCCAAGGAGAC

AGTCTCAGAAGCTATTATGCAAGCTGGTACCAGCAGAAGCCAGGACAGGCCCCTGTACT

TGTCATCTATGGTAAAAACAACCGGCCCTCAGGGATCCCATACCGATTCTCTGGCTCCAG

CTCAGGAAACACAGCTTCCTTGACCATCACTGGGGCTCAGGCGGAAGATGAGGCTGACT

ATTACTGTAACTCCTCTCCGCCCACTCCTGATACGGTGGTATTCGGCGGAGGGACCAAGC

TGACCGTCCTAGGCATATCGGCCATGGTTAGATCTGACAAAACTCACACATGCCCACCGT

GCCCAGCACCTGAACTCCTGGGGGGACCGTCAGTCTTCCTCTTCCCCCCAAAACCCAAG

GACACCCTCATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGCATAATGCCA

AGACAAAGCCGCGGGAGGAGCAGTACAACAGCACGTACCGTGTGGTCAGCGTCCTCAC

CGTCCTGCACCAGGACTGGCTGAATGGCAAGGAGTACAAGTGCAAGGTCTCCAACAAA

GCCCTCCCAGCCCCCATCGAGAAAACCATCTCCAAAGCCAAAGGGCAGCCCCGAGAAC

CACAGGTGTACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGAGAGCAATGG

GCAGCCGGAGAACAACTACAAGACCACGCCTCCCGTGCTGGACTCCGACGGCTCCTTCT

TCCTCTACAGCAAGCTCACCGTGGACAAGAGCAGGTGGCAGCAGGGGAACGTCTTCTCA

TGCTCCGTGATGCATGAGGCTCTGCACAACCACTACACGCAGAAGAGCCTCTCCCTGTC

TCCGGGTAAATGA

IEOmAB3-scFv-hIgG amino acid sequence (SEQ ID NO: 10)

EVQLLESGGGLVQPGGSLRLSCAASGFTFSSYAMSWVRQAPGKGLEWVSAISGSGGSTYYA

DSVKGRFTISRDNSKNTLYLQMNSLRAEDTAVYYCAKVMGRNAFDYWGQGTLVTASGGG

GSGGGGSGGGGSSELTQDPAVSVALGQTVRITCQGDSLRSYYASWYQQKPGQAPVLVIYGK

-continued

NNRPSGIPYRFSGSSSGNTASLTITGAQAEDEADYYCNSSPPTPDTVVFGGGTKLTVLGISAM

VRSDKTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK*

Schematic Representation of Antibody Molecules According to the Invention:

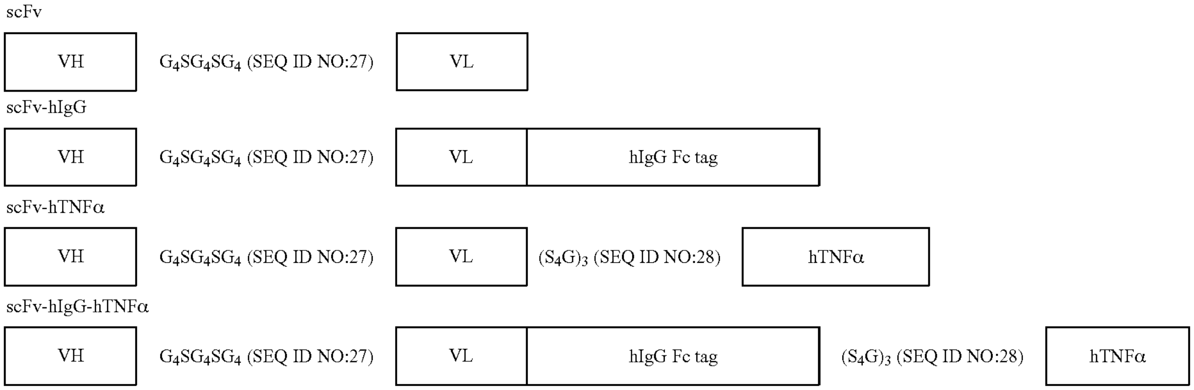

REFERENCES

1. Mellman, I., Coukos, G. & Dranoff, G. Cancer immunotherapy comes of age. *Nature* 480, 480-489 (2011).
2. Khalil, D. N., Smith, E. L., Brentjens, R. J. & Wolchok, J. D. The future of cancer treatment: immunomodulation, CARs and combination immunotherapy. *Nat Rev Clin Oncol* 13, 394 (2016).
3. Corraliza-Gorjon, I., Somovilla-Crespo, B., Santamaria, S., Garcia-Sanz, J. A. & Kremer, L. New Strategies Using Antibody Combinations to Increase Cancer Treatment Effectiveness. *Front Immunol* 8, 1804 (2017).
4. Weiner, L. M., Surana, R. & Wang, S. Monoclonal antibodies: versatile platforms for cancer immunotherapy. *Nat Rev Immunol* 10, 317-327 (2010).
5. Garnacho, C., Albelda, S. M., Muzykantov, V. R. & Muro, S. Differential intra-endothelial delivery of polymer nanocarriers targeted to distinct PECAM-1 epitopes. *J Control Release* 130, 226-233 (2008).
6. Mennonna, D., et al. T cell neoepitope discovery in colorectal cancer by high throughput profiling of somatic mutations in expressed genes. *Gut* 66, 454-463 (2017).
7. Chen, Y. T., et al. Identification of cancer/testis-antigen genes by massively parallel signature sequencing. *Proc Natl Acad Sci USA* 102, 7940-7945 (2005).
8. Bassani-Sternberg, M. & Coukos, G. Mass spectrometry-based antigen discovery for cancer immunotherapy. *Curr Opin Immunol* 41, 9-17 (2016).
9. Turtoi, A., et al. Novel comprehensive approach for accessible biomarker identification and absolute quantification from precious human tissues. *J Proteome Res* 10, 3160-3182 (2011).
10. Dhanik, A., et al. In-silico discovery of cancer-specific peptide-HLA complexes for targeted therapy. *BMC Bioinformatics* 17, 286 (2016).
11. Mardis, E. R. Neoantigen Discovery in Human Cancers. *Cancer J* 23, 97-101 (2017).
12. Sanchez-Martin, D., et al. Selection strategies for anticancer antibody discovery: searching off the beaten path. *Trends Biotechnol* 33, 292-301 (2015).
13. Uva, P., et al. Comparative Membranome expression analysis in primary tumors and derived cell lines. *PLoS One* 5, e11742 (2010).
14. Johannsen, M., et al. The tumour-targeting human L19-IL2 immunocytokine: preclinical safety studies, phase I clinical trial in patients with solid tumours and expansion into patients with advanced renal cell carcinoma. *Eur J Cancer* 46, 2926-2935 (2010).
15. Frenzel, A., Schirrmann, T. & Hust, M. Phage display-derived human antibodies in clinical development and therapy. *MAbs* 8, 1177-1194 (2016).
16. Hunger, S. P., et al. Improved survival for children and adolescents with acute lymphoblastic leukemia between 1990 and 2005: a report from the children's oncology group. *J Clin Oncol* 30, 1663-1669 (2012).
17. Litzow, M. R. & Ferrando, A. A. How I treat T-cell acute lymphoblastic leukemia in adults. *Blood* 126, 833-841 (2015).
18. Kunz, J. B., et al. Pediatric T-cell lymphoblastic leukemia evolves into relapse by clonal selection, acquisition of mutations and promoter hypomethylation. *Haematologica* 100, 1442-1450 (2015).
19. Nguyen, K., et al. Factors influencing survival after relapse from acute lymphoblastic leukemia: a Children's Oncology Group study. *Leukemia* 22, 2142-2150 (2008).
20. Silacci, M., et al. Design, construction, and characterization of a large synthetic human antibody phage display library. *Proteomics* 5, 2340-2350 (2005).
21. Eriksson, F., et al. Tumor-specific bacteriophages induce tumor destruction through activation of tumor-associated macrophages. *J Immunol* 182, 3105-3111 (2009).

22. Meyer, L. H., et al. Early relapse in ALL is identified by time to leukemia in NOD/SCID mice and is characterized by a gene signature involving survival pathways. *Cancer Cell* 19, 206-217 (2011).
23. Brenner, D., Blaser, H. & Mak, T. W. Regulation of tumour necrosis factor signalling: live or let die. *Nat Rev Immunol* 15, 362-374 (2015).
24. Sarnat, H. B. & Flores-Sarnat, L. Embryology of the neural crest: its inductive role in the neurocutaneous syndromes. *J Child Neurol* 20, 637-643 (2005).
25. Bossi, D., et al. In Vivo Genetic Screens of Patient-Derived Tumors Revealed Unexpected Frailty of the Transformed Phenotype. *Cancer Discov* 6, 650-663 (2016).
26. Kratochvill, F., et al. TNF Counterbalances the Emergence of M2 Tumor Macrophages. *Cell Rep* 12, 1902-1914 (2015).
27. DuPage, M., Mazumdar, C., Schmidt, L. M., Cheung, A. F. & Jacks, T. Expression of tumour-specific antigens underlies cancer immunoediting. *Nature* 482, 405-409 (2012).
28. Teng, G., et al. MicroRNA-155 is a negative regulator of activation-induced cytidine deaminase. *Immunity* 28, 621-629 (2008).
29. Morgan, R. A., et al. Cancer regression and neurological toxicity following anti-MAGE-A3 TCR gene therapy. *J Immunother* 36, 133-151 (2013).
30. Linette, G. P., et al. Cardiovascular toxicity and titin cross-reactivity of affinity-enhanced T cells in myeloma and melanoma. *Blood* 122, 863-871 (2013).
31. Pavlinkova, G., et al. Effects of humanization and gene shuffling on immunogenicity and antigen binding of anti-TAG-72 single-chain Fvs. *Int J Cancer* 94, 717-726 (2001).
32. Porter, D. L., et al. Chimeric antigen receptor T cells persist and induce sustained remissions in relapsed refractory chronic lymphocytic leukemia. *Sci Transl Med* 7, 303ra139 (2015).
33. Schmidt, E., Hennig, K., Mengede, C., Zillikens, D. & Kromminga, A. Immunogenicity of rituximab in patients with severe pemphigus. *Clin Immunol* 132, 334-341 (2009).
34. Harding, F. A., Stickler, M. M., Razo, J. & DuBridge, R. B. The immunogenicity of humanized and fully human antibodies: residual immunogenicity resides in the CDR regions. *MAbs* 2, 256-265 (2010).
35. Danielli, R., et al. Armed antibodies for cancer treatment: a promising tool in a changing era. *Cancer Immunol Immunother* 64, 113-121 (2015).
36. Danielli, R., et al. Intralesional administration of L19-IL2/L19-TNF in stage III or stage IVM1a melanoma patients: results of a phase II study. *Cancer Immunol Immunother* 64, 999-1009 (2015).
37. Bauer, S., et al. Sequential cancer immunotherapy: targeted activity of dimeric TNF and IL-8. *Cancer Immun* 9, 2 (2009).
38. Roberts, N. J., Zhou, S., Diaz, L. A., Jr. & Holdhoff, M. Systemic use of tumor necrosis factor alpha as an anticancer agent. *Oncotarget* 2, 739-751 (2011).
39. Chapman, P. B., et al. Clinical pharmacology of recombinant human tumor necrosis factor in patients with advanced cancer. *J Clin Oncol* 5, 1942-1951 (1987).
40. Monegal, A., et al. Immunological applications of single-domain llama recombinant antibodies isolated from a naive library. *Protein Eng Des Sel* 22, 273-280 (2009).
41. Massa, P. E., Paniccia, A., Monegal, A., de Marco, A. & Rescigno, M. *Salmonella* engineered to express CD20-targeting antibodies and a drug-converting enzyme can eradicate human lymphomas. *Blood* 122, 705-714 (2013).
42. Gibson, D. G., et al. Enzymatic assembly of DNA molecules up to several hundred kilobases. *Nat Methods* 6, 343-345 (2009).
43. Longo, P. A., Kavran, J. M., Kim, M. S. & Leahy, D. J. Transient mammalian cell transfection with polyethylenimine (PEI). *Methods Enzymol* 529, 227-240 (2013).
44. Rich, J. T., et al. A practical guide to understanding Kaplan-Meier curves. *Otolaryngol Head Neck Surg* 143, 331-336 (2010).
45. Heitjan, D. F., Manni, A. & Santen, R. J. Statistical analysis of in vivo tumor growth experiments. *Cancer Res* 53, 6042-6050 (1993).
46. Madenci A. L., et al. The role of thymectomy in the treatment of juvenile myasthenia gravis: a systematic review. *Pediatr Surg Int* 33, 683-694 (2017).
47. Rider D. A., et al. A Human CD4 Monoclonal Antibody for the Treatment of T-Cell Lymphoma Combines Inhibition of T-Cell Signaling by a Dual Mechanism with Potent Fc-Dependent Effector Activity. *Cancer Res* 67, 9945-9953 (2007).

The invention claimed is:

1. An isolated monoclonal antibody or a fragment thereof wherein each monoclonal antibody or fragment comprises a heavy chain variable region (VH) comprising SEQ ID NO: 22 and a light chain variable region (VL) comprising SEQ ID NO: 25, wherein both the monoclonal antibody and the fragment bind to tumor cells with at least 1.5-fold greater affinity than to normal cells.

2. The monoclonal antibody or the antigen-binding fragment thereof according to claim 1 wherein the VH and the VL of the monoclonal antibody or the antigen-binding fragment are linked by an amino acid linker consisting of a sequence of from 15 amino acids to 19 amino acids that are not subject to intracellular cleavage by proteases, wherein the linker comprises SEQ ID NO: 27 (GGGGSGGGGSGGGG).

3. The monoclonal antibody or the antigen-binding fragment thereof according to claim 2 wherein the monoclonal antibody or the antigen-binding fragment thereof further comprises an IgG-Fc tag.

4. The monoclonal antibody or the antigen-binding fragment thereof according to claim 3 wherein the IgG-Fc tag is a human IgG1-Fc tag.

5. The monoclonal antibody or the antigen-binding fragment thereof according to claim 3 wherein the human IgG1-Fc tag comprises a sequence having at least 90% identity to SEQ ID NO:30.

6. The monoclonal antibody or the antigen-binding fragment thereof according to claim 1 wherein the monoclonal antibody or the antigen-binding fragment thereof comprises a sequence having SEQ ID NO:4 or SEQ ID NO: 38.

7. The monoclonal antibody or the antigen-binding fragment thereof according to claim 1 wherein the monoclonal antibody or the antigen-binding fragment thereof is fused to at least one molecule selected from the group consisting of: pro-inflammatory cytokines, interferons (IFNs) and/or radionuclides or domains able to recruit radio/chemotherapy compounds, bacterial and fungal toxins, chemotherapeutic agents, enzymes, other domains mediating the attachment of the antibody to the plasma membrane or to vesicles wherein the plasma membrane or vesicles are derived from a cell or artificial source, fluorophores or markers.

8. The monoclonal antibody or the antigen-binding fragment thereof according to claim 1 wherein the monoclonal antibody or the antigen-binding fragment thereof binds to at least 20% of murine T-ALL blasts and/or to at least 50% of a human T-ALL cell line; and/or exhibiting at least 2.5-fold stronger signal on tumor than normal cells.

9. The monoclonal antibody or the antigen-binding fragment thereof according to claim 7 wherein the molecule is linked to the VH or the IgG-Fc tag of the monoclonal antibody or the antigen-binding fragment thereof by an amino acid linker consisting of a sequence of from 15 aa to 19 amino acids that is not subjected to intracellular cleavage by proteases.

10. The monoclonal antibody or the antigen-binding fragment thereof according to claim 9, wherein the linker comprises the sequence set forth in in SEQ ID NO: 28 (SSSSGSSSSGSSSSG).

11. The antigen-binding fragment of the monoclonal antibody according to claim 1, wherein the fragment is a single-chain variable fragment (scFv).

12. The monoclonal antibody or an antigen-binding fragment thereof according to claim 1 wherein the monoclonal antibody or the antigen-binding fragment thereof is fused to human TNF-α or functional fragments thereof.

13. A pharmaceutical composition comprising at least one monoclonal antibody or an antigen-binding fragment thereof according to claim 1 and at least one pharmaceutically acceptable excipient.

14. A nucleic acid molecule encoding the monoclonal antibody or the recombinant or synthetic antigen-binding fragment thereof according to claim 1.

15. An expression vector comprising the nucleic acid molecule of claim 14.

16. A host cell that produces the monoclonal antibody or the recombinant or synthetic antigen-binding fragment thereof according to claim 1.

17. A method for the treatment of melanoma, the method comprising administering to a patient in need thereof the monoclonal antibody or the recombinant or synthetic antigen-binding fragment thereof according to claim 1.

18. A method for the treatment of human T-cell acute lymphoblastic leukemia (hT-ALL), the method comprising administering to a patient in need thereof the monoclonal antibody or the recombinant or synthetic antigen-binding fragment thereof according to claim 1.

* * * * *